United States Patent
Shen et al.

(10) Patent No.: US 10,947,222 B2
(45) Date of Patent: Mar. 16, 2021

(54) INDOLE DERIVATIVES USEFUL AS INHIBITORS OF DIACYLGLYCERIDE O-ACYLTRANSFERASE 2

(71) Applicants: Merck Sharp & Dohme Corp., Rahway, NJ (US); Dong-Ming Shen, Edison, NJ (US); Thomas H. Graham, Quincy, MA (US); Jinlong Jiang, Scotch Plains, NJ (US); Fa-Xiang Ding, Staten Island, NY (US); Clare Tudge, Wayne, PA (US)

(72) Inventors: Dong-Ming Shen, Edison, NJ (US); Thomas H. Graham, Quincy, MA (US); Jinlong Jiang, Scotch Plains, NJ (US); Fa-Xiang Ding, Staten Island, NY (US); Clare Tudge, Wayne, PA (US)

(73) Assignee: Merck Sharp & Dohme Corp., Rahway, NJ (US)

(*) Notice: Subject to any disclaimer, the term of this patent is extended or adjusted under 35 U.S.C. 154(b) by 81 days.

(21) Appl. No.: 16/461,880

(22) PCT Filed: Nov. 13, 2017

(86) PCT No.: PCT/US2017/061226
§ 371 (c)(1),
(2) Date: May 17, 2019

(87) PCT Pub. No.: WO2018/093698
PCT Pub. Date: May 24, 2018

(65) Prior Publication Data
US 2019/0276443 A1    Sep. 12, 2019

Related U.S. Application Data

(60) Provisional application No. 62/424,106, filed on Nov. 18, 2016.

(51) Int. Cl.
| | | |
|---|---|---|
| C07D 401/12 | (2006.01) | |
| C07D 409/12 | (2006.01) | |
| A61P 1/16 | (2006.01) | |
| C07D 209/08 | (2006.01) | |
| C07D 409/14 | (2006.01) | |
| C07D 413/12 | (2006.01) | |
| A61K 31/506 | (2006.01) | |
| A61K 45/06 | (2006.01) | |
| C07D 413/14 | (2006.01) | |
| A61K 31/404 | (2006.01) | |
| A61K 31/4439 | (2006.01) | |
| C07D 209/10 | (2006.01) | |

(52) U.S. Cl.
CPC .......... *C07D 409/12* (2013.01); *A61K 31/404* (2013.01); *A61K 31/4439* (2013.01); *A61K 31/506* (2013.01); *A61K 45/06* (2013.01); *A61P 1/16* (2018.01); *C07D 209/08* (2013.01); *C07D 209/10* (2013.01); *C07D 401/12* (2013.01); *C07D 409/14* (2013.01); *C07D 413/12* (2013.01); *C07D 413/14* (2013.01)

(58) Field of Classification Search
CPC .. C07D 401/12; C07D 409/12; C07D 401/13; C07D 4013/12; A61K 31/5355; A61K 31/506; A61K 31/4439; A61K 31/4045; A61P 3/04; A61P 3/06; A61P 3/10
USPC ....... 544/331; 546/278.1; 548/467; 514/275, 514/339, 237.2, 419
See application file for complete search history.

(56) References Cited

U.S. PATENT DOCUMENTS

| | | |
|---|---|---|
| 2006/0189606 A1 | 8/2006 | Karp et al. |
| 2012/0015052 A1 | 1/2012 | Burgey et al. |
| 2013/0116283 A1 | 5/2013 | Schunk et al. |
| 2014/0057909 A1 | 2/2014 | Lee et al. |

FOREIGN PATENT DOCUMENTS

| | | |
|---|---|---|
| WO | 2006019831 A1 | 2/2006 |
| WO | 2006117314 | 11/2006 |
| WO | 2007084413 | 7/2007 |

(Continued)

OTHER PUBLICATIONS

International Search Report, PCT/US17/061226, dated Feb. 16, 2018, 10 pages.

*Primary Examiner* — Jeffrey H Murray
(74) *Attorney, Agent, or Firm* — Sarah L. Hooson; Catherine D. Fitch

(57) ABSTRACT

The present invention relates to a compound represented by formula I: and pharmaceutically acceptable salts thereof. The compounds of formula I are inhibitors of diacylglyceride O-acyltransferase 2 ("DGAT2") and may be useful in the treatment, prevention and suppression of diseases mediated by DGAT2. The compounds of the present invention may be useful in the treatment of hepatic steatosis, diabetes mellitus, obesity, hyperlipidemia, hypercholesterolemia, atherosclerosis, nonalcoholic steatohepatitis (NASH), cardiorenal diseases such as chronic kidney diseases and heart failure and related diseases and conditions.

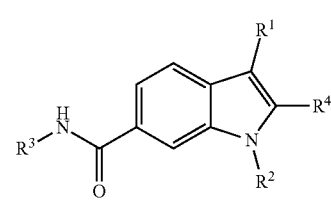

13 Claims, No Drawings

(56) References Cited

FOREIGN PATENT DOCUMENTS

| | | |
|---|---|---|
| WO | 2007084435 | 7/2007 |
| WO | 2008015125 | 2/2008 |
| WO | 2008088692 | 7/2008 |
| WO | 2009058298 | 5/2009 |
| WO | 2009058299 | 5/2009 |
| WO | 2010051188 | 5/2010 |
| WO | 2010107765 | 9/2010 |
| WO | 2010111058 | 9/2010 |
| WO | 2010111059 | 9/2010 |
| WO | 2010111060 | 9/2010 |
| WO | 2010118009 | 10/2010 |
| WO | 2014081994 A1 | 5/2014 |
| WO | 2016036633 | 3/2016 |
| WO | 2016036636 | 3/2016 |
| WO | 2016036638 | 3/2016 |
| WO | 2016187384 | 11/2016 |

INDOLE DERIVATIVES USEFUL AS INHIBITORS OF DIACYLGLYCERIDE O-ACYLTRANSFERASE 2

CROSS-REFERENCE TO RELATED APPLICATIONS

This application is a U.S. National Phase application under 35 U.S.C. § 371 of PCT/US2017/061226 filed on Nov. 13, 2017, which claims priority 62/424,106 filed on Nov. 18, 2016, the contents of which are hereby incorporated by reference in their entireties.

FIELD OF THE INVENTION

The present invention is directed to indole derivative compounds which inhibit diacylglyceride O-acyltransferase 2 ("DGAT2"), may be useful for preventing, treating or acting as a remedial agent for hepatic steatosis, type-2 diabetic mellitus, obesity, hyperlipidemia, hypercholesterolemia, atherosclerosis, nonalcoholic steatohepatitis (NASH), cardiorenal diseases such as chronic kidney diseases and heart failure, and related diseases and conditions, as well as methods of making such compounds and pharmaceutical compositions comprising such a compound and a pharmaceutical carrier.

BACKGROUND OF THE INVENTION

Triacylglycerols ("TGs") serve several functions in living organisms. One such function of TGs is in the storage of energy. TGs also play a role in the synthesis of membrane lipids. TG synthesis in cells may protect them from the potentially toxic effects of excess fatty acid ("FA"). In enterocytes and hepatocytes, TGs are synthesized for the assembly and secretion of lipoproteins which transport FA between tissues. TGs play a role in the skin's surface water barrier, and TGs in adipose tissue provide insulation for organisms.

The glycerol phosphate and the monoacylglycerol pathways are the major pathways for the biosynthesis of TG. However, the last step in the synthesis of TG involves the reaction of a fatty acyl-CoA and diacylglycerol ("DG") to form TG. The reaction is catalyzed by acyl-CoA:diacylglycerol acyltransferase ("DGAT") enzymes. There have been identified two DGAT enzymes, DGAT1 and DGAT2. Although DGAT1 and DGAT2 catalyze the same reaction, they differ significantly at the level of DNA and protein sequences.

DGAT2 is an integral membrane protein of the endoplasmic reticulum ("ER") and is expressed strongly in adipose tissue and the liver. DGAT2 appears to be the dominant DGAT enzyme controlling TG homeostasis in vivo. DGAT2 deficient mice survive for only a few hours after birth. On the other hand, DGAT1 deficient mice are viable.

In a study, DGAT2 knockdown in ob/ob mice with a DGAT2 gene-specific antisense oligonucleotide resulted in a dose dependent decrease in very low density lipoprotein ("VLDL") and a reduction in plasma TG, total cholesterol, and ApoB. Liu, et al., Biochim. Biophys Acta 2008, 1781, 97. In the same study, DGAT2 antisense oligonucleotide treatment of ob/ob mice showed a decrease in weight gain, adipose weight and hepatic TG content. Id. In another study, antisense treatment of ob/ob mice improved hepatic steatosis and hyperlipidemia. Yu, et al., Hepatology, 2005, 42, 362. In another study, diet-induced hepatic steatosis and insulin resistance was improved by knocking down DGAT2 in rats. Choi et al., J. Bio. Chem., 2007, 282, 22678.

In light of the above description, inhibitors of DGAT2 may be considered useful as agents for treating and/or preventing hepatic steatosis, diabetes mellitus, obesity, hyperlipidemia, hypercholesterolemia, atherosclerosis, non-alcoholic steatohepatitis (NASH), cardiorenal diseases such as chronic kidney diseases and heart failure and related diseases and conditions.

SUMMARY OF THE INVENTION

The present invention relates to compounds represented by Formula I:

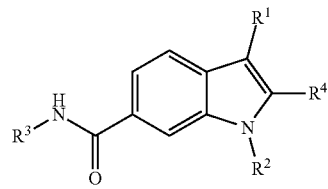

as well as pharmaceutically acceptable salts thereof, and pharmaceutical compositions comprising a compound of Formula I.

The present invention further relates to methods of inhibiting DGAT2, and methods of treating hepatic steatosis, diabetes mellitus, obesity, hyperlipidemia, hypercholesterolemia, atherosclerosis, nonalcoholic steatohepatitis (NASH), cardiorenal diseases such as chronic kidney diseases and heart failure and related diseases and conditions, comprising administering a compound of Formula I to a patient in need thereof.

DETAILED DESCRIPTION OF THE INVENTION

The present invention is directed to compounds having structural Formula I:

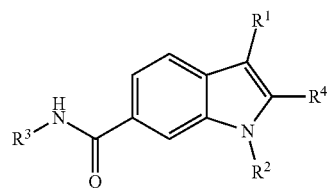

or a pharmaceutically acceptable salt thereof wherein:
$R^1$ is
(1) aryl unsubstituted or substituted by 1, 2, or 3 $R^5$, or
(2) 5- or 6-membered heteroaryl containing 1, 2 or 3 heteroatoms independently selected from N, O, and S, wherein the heteroaryl is unsubstituted or substituted by 1, 2, or 3 $R^5$, or
(3) 8- to 10-membered fused heteroaryl containing 1, 2 or 3 heteroatoms independently selected from N, O, or S, wherein the heteroaryl is unsubstituted or substituted by 1, 2, or 3 $R^5$;

$R^2$ is

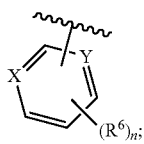

$R^3$ is
(1) —$(C_{1-6})$alkyl-O—$(C_{1-3})$alkyl,
(2) 4- to 7-membered monocyclic or 6- to 10-membered bicyclic heterocyclyl containing 1 or 2 heteroatoms independently selected from N, O, and S, wherein the heterocyclyl is unsubstituted or substituted by 1, 2, or 3 $R^7$,
(3) —$(C_{1-6})$alkyl-heterocyclyl containing 1 or 2 heteroatoms independently selected from N, O, and S, and wherein the heterocyclyl is a 5- to 7-membered ring, or
(4) —$(C_{1-6})$alkyl-pyridinyl, wherein the pyridinyl is unsubstituted or substituted with $(C_{1-3})$alkyl or halo$(C_{1-3})$alkyl, and wherein the alkyl is unsubstituted or substituted with a hydroxy;
$R^4$ is
(1) hydrogen,
(2) $(C_{1-3})$alkyl, or
(3) CN;
each $R^5$ is independently selected from
(1) halo,
(2) $(C_{1-3})$alkyl,
(3) halo$(C_{1-3})$alkyl,
(4) $(C_{3-6})$cycloalkyl,
(5) —C(O)NH$_2$,
(6) —C(O)O$(C_{1-3})$alkyl,
(7) $(C_{1-3})$alkoxy,
(8) halo$(C_{1-3})$alkoxy,
(9) hydroxy,
(10) phenyl,
(11) —NHC(O)CH$_3$,
(12) 5- or 6-membered heteroaryl containing 1, 2, or 3 heteroatoms independently selected from N, O, or S, wherein the heteroaryl is unsubstituted or substituted by 1 or 2 $(C_{1-3})$alkyl, or hydroxy,
(13) CN,
(14) hydroxy$(C_{1-3})$alkyl, or
(15) $(C_{1-3})$alkyl-heterocyclyl, wherein the heterocyclyl contains 1 or 2 heteroatoms independently selected from N, O, or S, and wherein the heterocyclyl is a 5- to 7-membered ring;
each $R^6$ is
(1) hydrogen, or
(2) halo;
each $R^7$ is
(1) oxo, or
(2) $(C_{1-3})$alkyl;
X is CH or N;
Y is CH or N; and
n is 1 or 2.

In one embodiment, $R^1$ is aryl unsubstituted or substituted by 1, 2, or 3 $R^5$. In one class of this embodiment, $R^3$ is —$(C_{1-6})$alkyl-O—$(C_{1-3})$alkyl. In one class of this embodiment, $R^3$ is a 5- to 7-membered heterocyclyl containing 1 or 2 heteroatoms independently selected from N, O, and S, wherein the heterocyclyl is unsubstituted or substituted by 1, 2, or 3 $R^7$. In one class of this embodiment, $R^3$ is —$(C_{1-6})$alkyl-heterocyclyl containing 1 or 2 heteroatoms independently selected from N, O, and S, and wherein the heterocyclyl is a 5- to 7-membered ring. In one embodiment, $R^3$ is —$(C_{1-6})$alkyl-pyridinyl, wherein the pyridinyl is unsubstituted or substituted with $(C_{1-3})$alkyl or halo$(C_{1-3})$alkyl, and wherein the alkyl is unsubstituted or substituted with a hydroxy.

In one embodiment, $R^1$ is 5- or 6-membered heteroaryl containing 1, 2, or 3 heteroatoms independently selected from N, O, and S, wherein the heteroaryl is unsubstituted or substituted by 1, 2, or 3 $R^5$. In one class of this embodiment, $R^3$ is —$(C_{1-6})$alkyl-O—$(C_{1-3})$alkyl. In one class of this embodiment, $R^3$ is a 5- to 7-membered heterocyclyl containing 1 or 2 heteroatoms independently selected from N, O, and S, wherein the heterocyclyl is unsubstituted or substituted by 1, 2, or 3 $R^7$. In one class of this embodiment, $R^3$ is —$(C_{1-6})$alkyl-heterocyclyl containing 1 or 2 heteroatoms independently selected from N, O, and S, and wherein the heterocyclyl is a 5- to 7-membered ring. In one embodiment, $R^3$ is —$(C_{1-6})$alkyl-pyridinyl, wherein the pyridinyl is unsubstituted or substituted with $(C_{1-3})$alkyl or halo$(C_{1-3})$alkyl, and wherein the alkyl is unsubstituted or substituted with a hydroxy.

In one embodiment, $R^1$ is 8- to 10-membered fused heteroaryl containing 1, 2 or 3 heteroatoms independently selected from N, O, or S, wherein the heteroaryl is unsubstituted or substituted by 1, 2, or 3 $R^5$. In one class of this embodiment, $R^3$ is —$(C_{1-6})$alkyl-O—$(C_{1-3})$alkyl. In one class of this embodiment, $R^3$ is a 5- to 7-membered heterocyclyl containing 1 or 2 heteroatoms independently selected from N, O, and S, wherein the heterocyclyl is unsubstituted or substituted by 1, 2, or 3 $R^7$. In one class of this embodiment, $R^3$ is —$(C_{1-6})$alkyl-heterocyclyl containing 1 or 2 heteroatoms independently selected from N, O, and S, and wherein the heterocyclyl is a 5- to 7-membered ring. In one embodiment, $R^3$ is —$(C_{1-6})$alkyl-pyridinyl, wherein the pyridinyl is unsubstituted or substituted with $(C_{1-3})$alkyl or halo$(C_{1-3})$alkyl, and wherein the alkyl is unsubstituted or substituted with a hydroxy.

In one embodiment, $R^1$ is

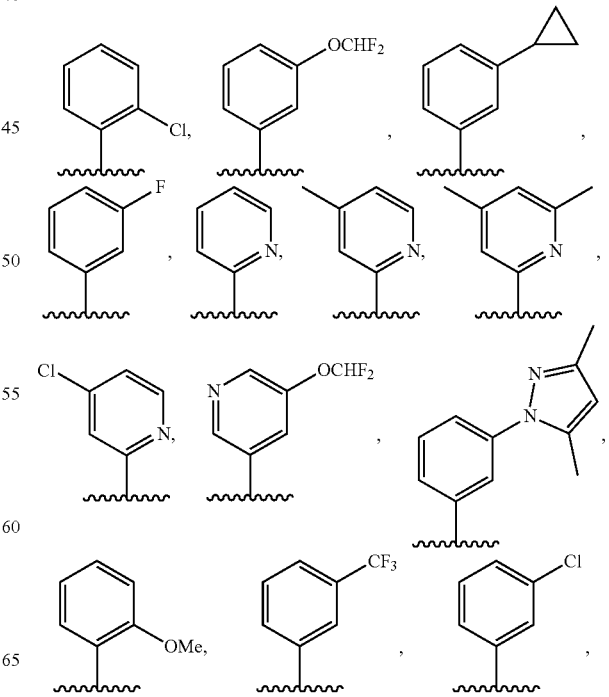

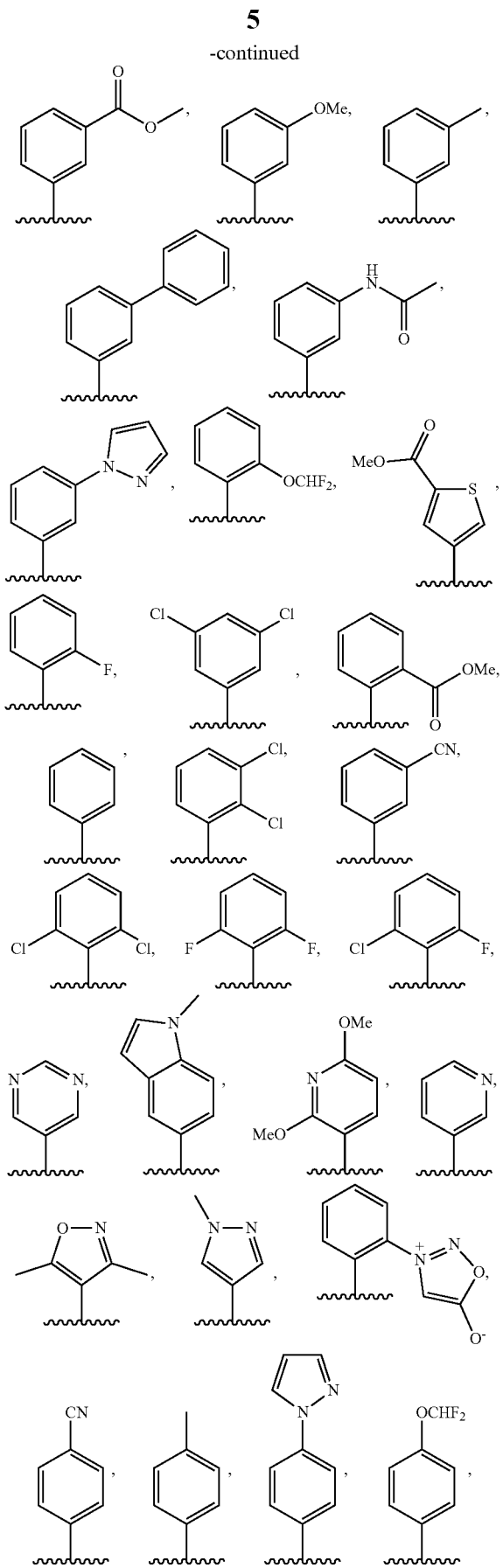

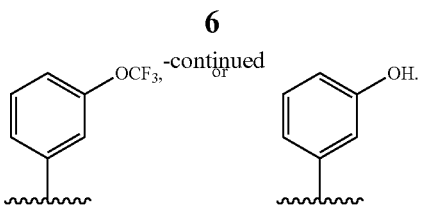

In one class of this embodiment, $R^3$ is —$(C_{1-6})$alkyl-O—$(C_{1-3})$alkyl. In one class of this embodiment, $R^3$ is a 5- to 7-membered heterocyclyl containing 1 or 2 heteroatoms independently selected from N, O, and S, wherein the heterocyclyl is unsubstituted or substituted by 1-3 $R^7$. In one class of this embodiment, $R^3$ is —$(C_{1-6})$alkyl-heterocyclyl containing 1 or 2 heteroatoms independently selected from N, O, and S, and wherein the heterocyclyl is a 5- to 7-membered ring. In one embodiment, $R^3$ is —$(C_{1-6})$alkyl-pyridinyl, wherein the pyridinyl is unsubstituted or substituted with $(C_{1-3})$alkyl or halo$(C_{1-3})$alkyl, and wherein the alkyl is unsubstituted or substituted with a hydroxy. In one class of this embodiment, $R^3$ is

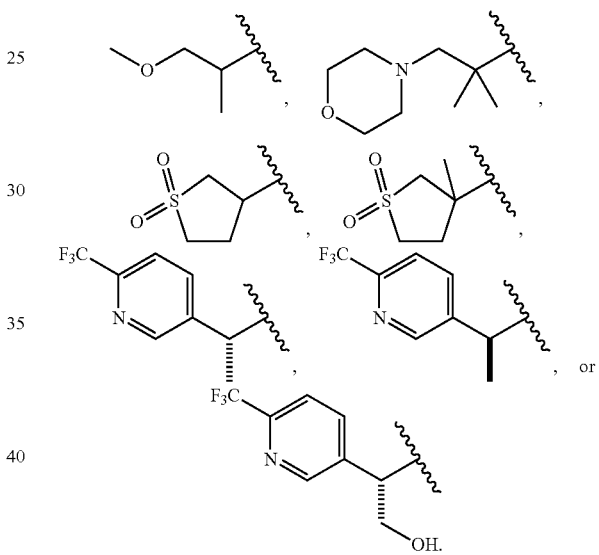

In one class of this embodiment, $R^3$ is

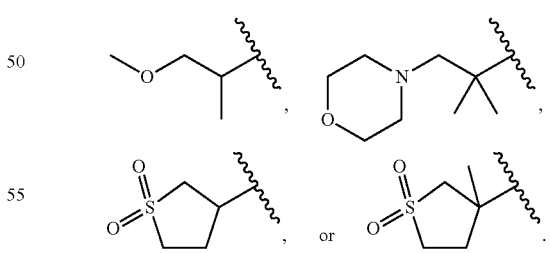

In one class of this embodiment, $R^3$ is

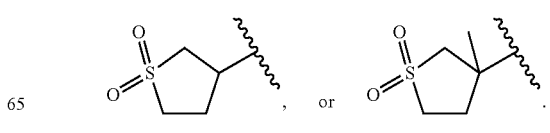

In one class of this embodiment, R³ is

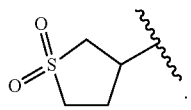

In on class of this embodiment, R³ is

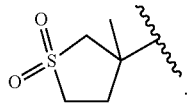

In one embodiment, R¹ is

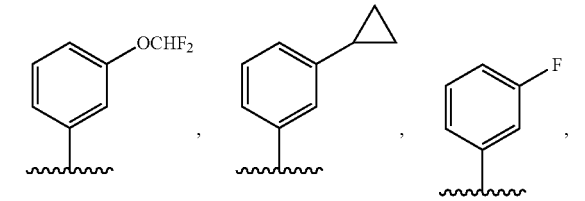

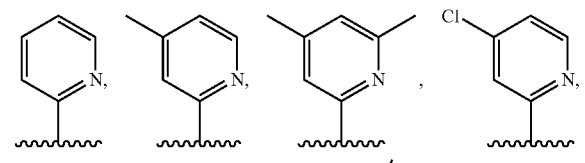

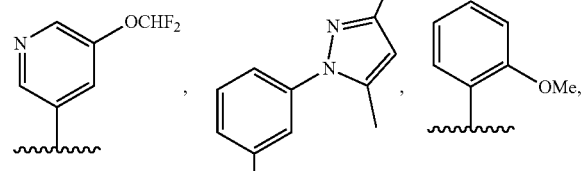

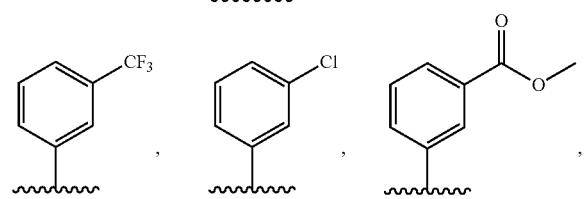

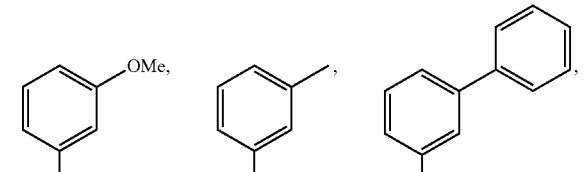

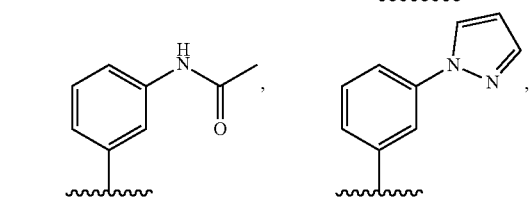

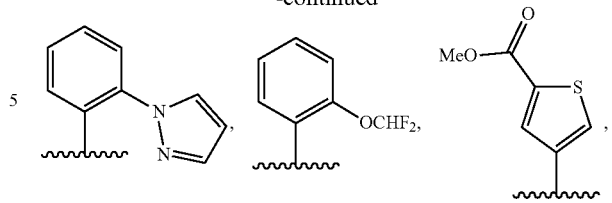

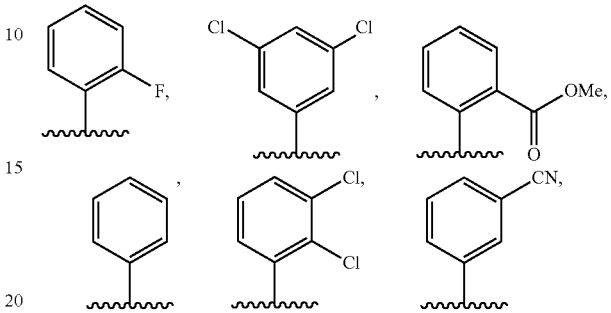

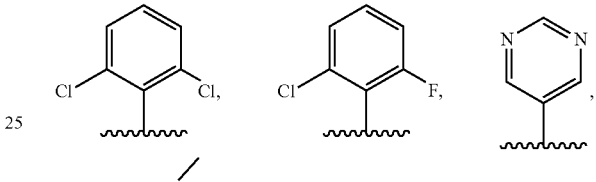

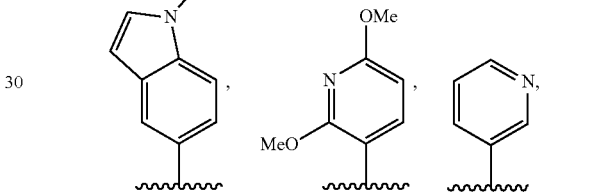

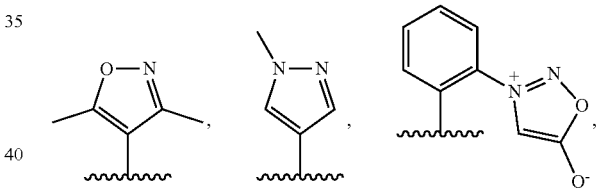

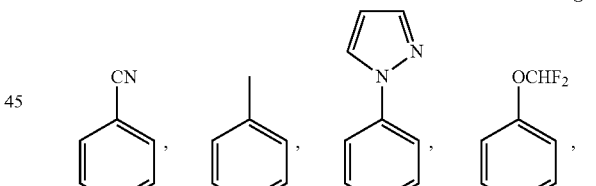

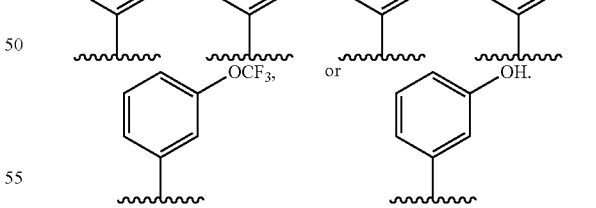

In one class of this embodiment, R³ is —($C_{1-6}$)alkyl-O—($C_{1-3}$)alkyl. In one class of this embodiment, R³ is a 5- to 7-membered heterocyclyl containing 1 or 2 heteroatoms independently selected from N, O, and S, wherein the heterocyclyl is unsubstituted or substituted by 1, 2, or 3 R⁷. In one class of this embodiment, R³ is —($C_{1-6}$)alkyl-heterocyclyl containing 1 or 2 heteroatoms independently selected from N, O, and S, and wherein the heterocyclyl is a 5- to 7-membered ring. In one embodiment, R³ is —($C_{1-6}$)alkyl-pyridinyl, wherein the pyridinyl is unsubstituted or substituted with (C$_{1-3}$)alkyl or halo(C$_{1-3}$)alkyl, and wherein the alkyl is unsubstituted or substituted with a hydroxy. In one class of this embodiment, R$^3$ is

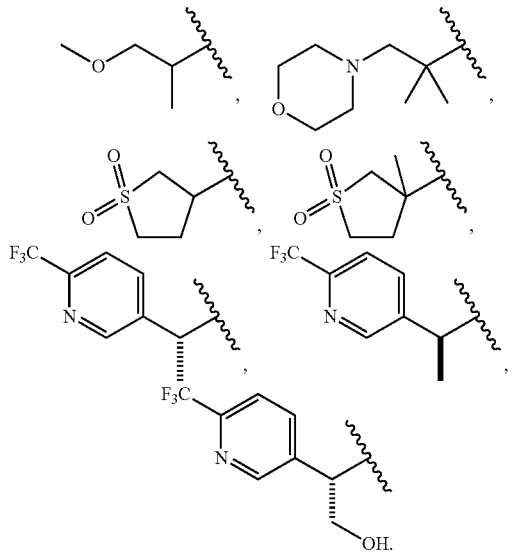

In one class of this embodiment, R$^3$ is

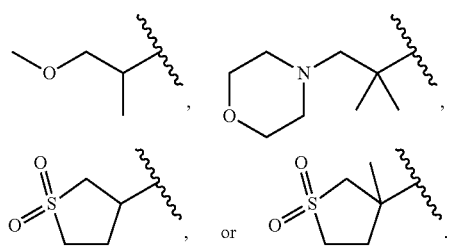

In one class of this embodiment, R$^3$ is

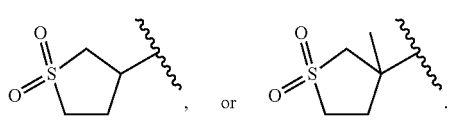

In one class of this embodiment, R$^3$ is

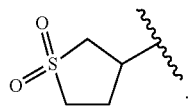 [SMILES: *C1CCS(=O)(=O)C1]

In one class of this embodiment, R$^3$ is

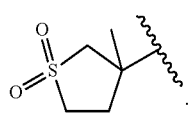

In one embodiment, R$^2$ is

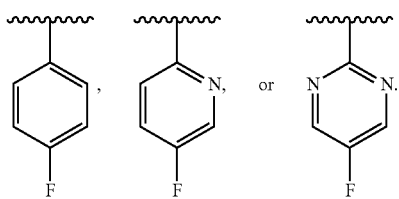

In one class of this embodiment, R$^2$ is

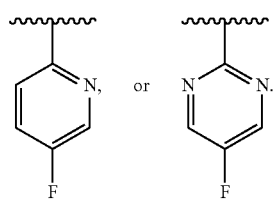 [SMILES: *c1ccc(F)cn1 ; *c1ncc(F)cn1]

In one class of this embodiment, R$^2$ is

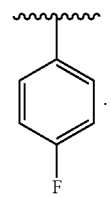 [SMILES: *c1ccc(F)cc1]

In one class of this embodiment, R$^2$ is

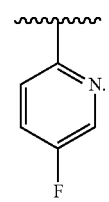 [SMILES: *c1ccc(F)cn1]

In one class of this embodiment, R$^2$ is

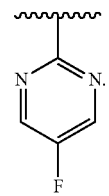 [SMILES: *c1ncc(F)cn1]

In one embodiment, $R^2$ is

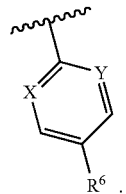

In one class of this embodiment, X is CH, and Y is CH. In one subclass of this class, $R^6$ is fluoro. In one class of this embodiment, X is CH and Y is N. In one subclass of this class, $R^6$ is fluoro. In one class of this embodiment, X is N, and Y is N. In one subclass of this class, $R^6$ is fluoro.

In one embodiment, $R^3$ is —$(C_{1-6})$alkyl-O—$(C_{1-3})$alkyl; a 5- to 7-membered heterocyclyl containing 1 or 2 heteroatoms independently selected from N, O, and S, wherein the heterocyclyl is unsubstituted or substituted by 1, 2, or 3 $R^7$; or —$(C_{1-6})$alkyl-heterocyclyl containing 1 or 2 heteroatoms independently selected from N, O and S, wherein the heterocyclyl is a 5- to 7-membered ring. In one class of this embodiment, $R^2$ is

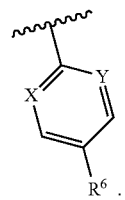

In one subclass of this class, $R^2$ is

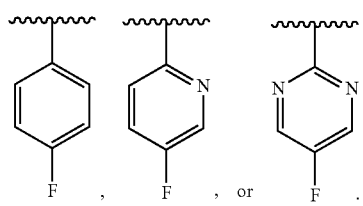

In one class of this embodiment, $R^3$ is

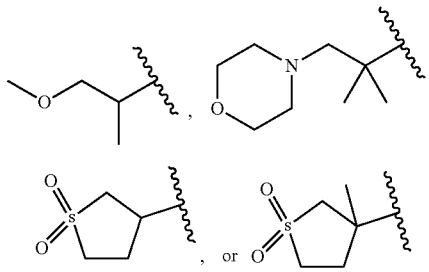

In one subclass of this class, $R^2$ is

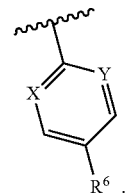

In one sub-subclass of this subclass, $R^2$ is

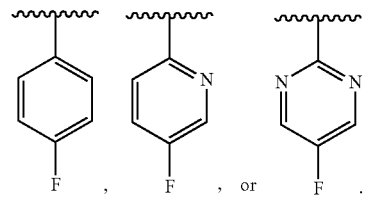

In one class of this embodiment, $R^3$ is

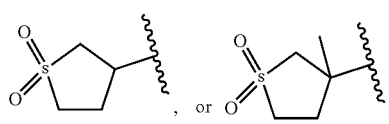

In one subclass of this class, $R^2$ is

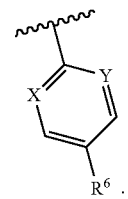

In one sub-subclass of this subclass, $R^2$ is

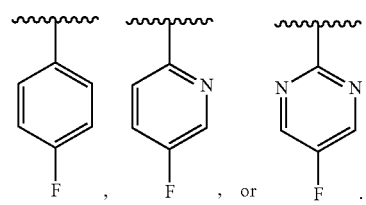

In one embodiment, $R^3$—$(C_{1-6})$alkyl-O—$(C_{1-3})$alkyl. In one class of this embodiment, $R^2$ is

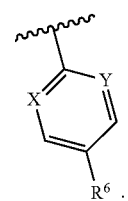

In one subclass of this class, $R^2$ is

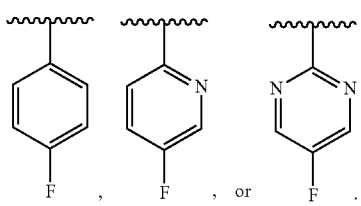, or .

In one embodiment, $R^3$ is a 5- to 7-membered heterocyclyl containing 1 or 2 heteroatoms independently selected from N, O, and S, wherein the heterocyclyl is unsubstituted or substituted by 1, 2, or 3 $R^7$. In one class of this embodiment, $R^2$ is

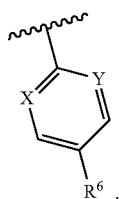.

In one subclass of this class, $R^2$ is

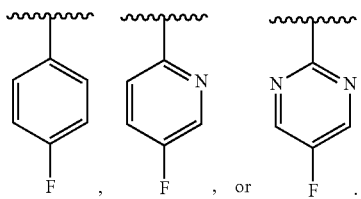, or .

In one embodiment, $R^3$ is —$(C_{1-6})$alkyl-heterocyclyl containing 1 or 2 heteroatoms independently selected from N, O, and S and wherein the heterocyclyl is a 5- to 7-membered ring. In one class of this embodiment, $R^2$ is

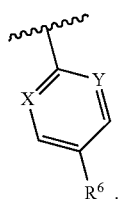.

In one subclass of this class, $R^2$ is

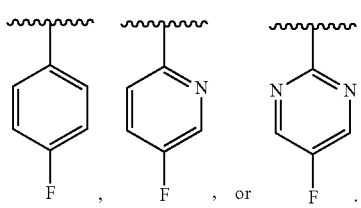, or .

In one embodiment, $R^3$ is —$(C_{1-6})$alkyl-pyridinyl, wherein the pyridinyl is unsubstituted or substituted with $(C_{1-3})$alkyl or halo$(C_{1-3})$alkyl, and wherein the alkyl is unsubstituted or substituted with a hydroxy. In one class of this embodiment, $R^2$ is

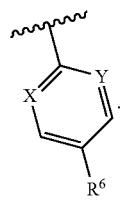.

In one subclass of this class, $R^2$ is

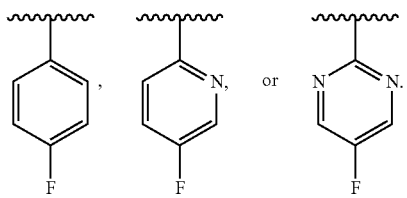, or .

In one embodiment, $R^3$ is

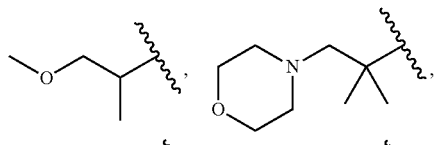

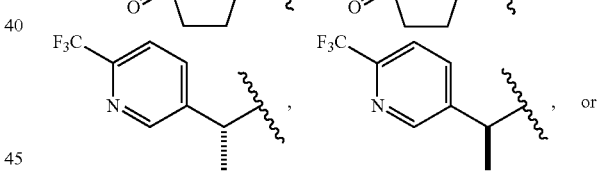

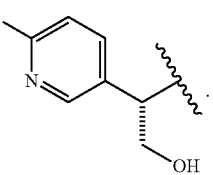.

In one class of this embodiment, $R^3$ is

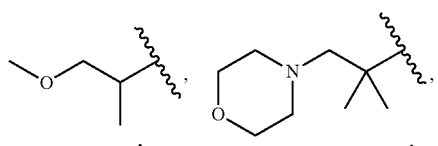

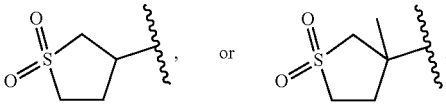

In one class of this embodiment, $R^3$ is

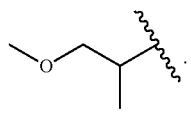 [SMILES: *C(C)COC]

In one class of this embodiment, $R^3$ is

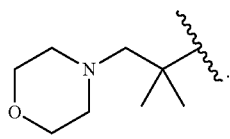 [SMILES: *C(C)(C)CN1CCOCC1]

In one class of this embodiment, $R^3$ is

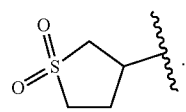

In one class of this embodiment, $R^4$ is

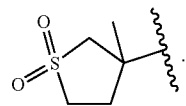

In one class of this embodiment, $R^3$ is

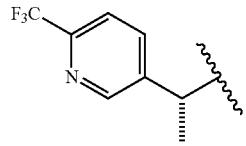

In one class of this embodiment, $R^3$ is

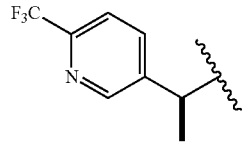

In one class of this embodiment, $R^3$ is

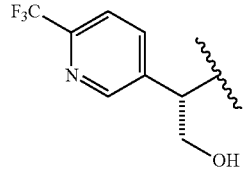

In one embodiment, $R^4$ is hydrogen. In one embodiment, $R^4$ is $(C_{1-3})$alkyl. In one embodiment, $R^4$ is CN. In one embodiment, $R^4$ is hydrogen, methyl, and CN. In one class of this embodiment, $R^4$ is methyl or CN.

In one embodiment, $R^6$ is hydrogen or halo.

In one class of this embodiment, $R^6$ is hydrogen, bromo, chloro, or fluoro. In one subclass of this class, $R^6$ is hydrogen. In one subclass of this class, $R^6$ is bromo, chloro, or fluoro. In one sub-subclass of this subclass, $R^6$ is chloro. In one sub-subclass of this subclass, $R^6$ is bromo. In one sub-subclass of this subclass, $R^6$ is fluoro.

In one embodiment, $R^2$ is

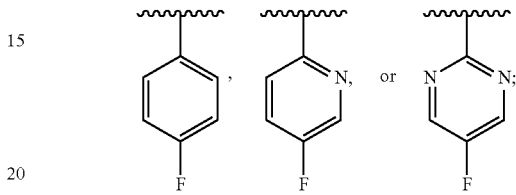

and $R^3$ is

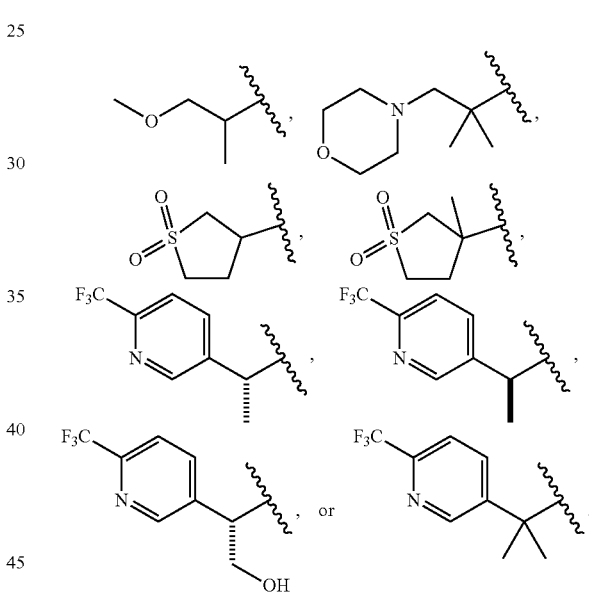

In one embodiment, the present invention is directed to compounds having structural Formula I-a:

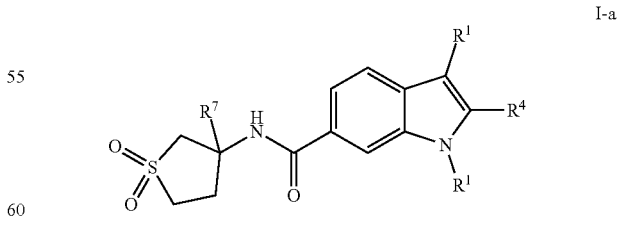

I-a or a pharmaceutically acceptable salt thereof, wherein $R^1$, $R^2$, and $R^4$ are as previously defined, and $R^7$ is hydrogen or $(C_{1-3})$alkyl.

In one embodiment, the present invention is directed to compounds having structural Formula I-b:

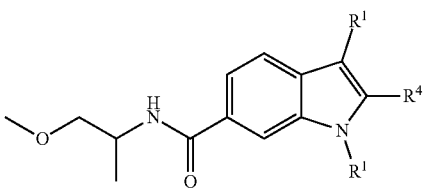

or a pharmaceutically acceptable salt thereof, wherein $R^1$, $R^2$, and $R^4$ are as previously defined.

In one embodiment, the present invention is directed to compounds having structural Formula I-c:

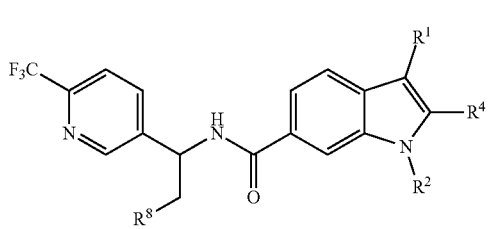

or a pharmaceutically acceptable salt thereof, wherein $R^1$, $R^2$, and $R^4$ are as previously defined, and $R^8$ is hydrogen or hydroxy.

In one embodiment, the present invention is directed to compounds having structural Formula I-d:

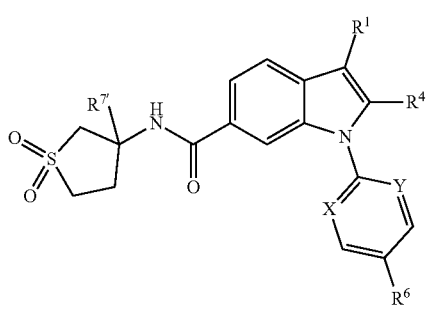

or a pharmaceutically acceptable salt thereof, wherein $R^1$, $R^4$, and $R^6$ are as previously defined and $R^{7'}$ is hydrogen or $(C_{1-3})$alkyl. In one class of this embodiment, X is CH and Y is CH. In one class of this embodiment, X is CH and Y is N. In one class of this embodiment, X is N and Y is N.

Pharmaceutically acceptable salts of the disclosed compounds including compounds of the structural Formulas, embodiments and classes thereof described herein are included within the present invention. Reference to the compounds of structural Formulas I to I-d includes the compounds of other generic structural Formulas and embodiments that fall within the scope of Formulas I to I-d.

"Alkyl" means branched- and straight-chain saturated aliphatic hydrocarbon groups having the specified number of carbon atoms when noted. If no number is specified, 1-6 carbon atoms are intended for linear and 3-7 carbon atoms for branched alkyl groups. Examples of alkyl groups include methyl, ethyl, propyl, isopropyl, butyl, sec- and tert-butyl, pentyl, hexyl, octyl, nonyl, and the like.

"Alkoxy" refers to an alkyl group linked to oxygen. Examples of alkoxy groups include methoxy, ethoxy, propoxy and the like.

"Aryl" means phenyl or naphthyl.

"Fused Phenyl" means a phenyl ring fused with heterocyclyl or cycloalkyl. Examples include 1,2,3,4-tetrahydronaphthalene, 1,2,3,4-tetrahydroquinoline, and indoline.

"Halogen" (halo) includes fluorine, chlorine, bromine and iodine.

"Cycloalkyl" means a saturated cyclic hydrocarbon radical having the number of carbon atoms designated. If no number of atoms is specified, 3-10 carbon atoms are intended. Cycloalkyl may also be fused, forming 1-3 carbocyclic rings. Examples of cycloalkyl include cyclopropyl, cyclobutyl, cyclopentyl, cyclohexyl, cycloheptyl, tetrahydronaphthyl, decahydronaphthyl, indanyl and the like.

Alkyl and cycloalkyl are each intended to include such carbon moieties containing isotopic forms of hydrogen (H) such as proton ($^1$H), for example but not limited to —$CH_3$, and/or deuterium ($^2$H, also denoted herein as D), for example but not limited to —$CD_3$.

"Haloalkyl" and derivatives such as "halo($C_{1-6}$)alkyl" include mono-substituted as well as multiple halo substituted alkyl groups, up to perhalo substituted alkyl. For example, trifluoromethyl is included.

"Haloalkoxy," "haloalkyl-O" and derivatives such as "halo($C_{1-6}$)alkoxy" are used interchangeably and refer to halo substituted alkyl groups linked through the oxygen atom. Haloalkoxy include mono-substituted as well as multiple halo substituted alkoxy groups, up to perhalo substituted alkoxy. For example trifluoromethoxy, chloromethoxy, and bromomethoxy are included.

"Heterocyclyl," "heterocycle" or "heterocyclic" refers to nonaromatic monocyclic ring structures in which one or more atoms in the ring, the heteroatom(s), is an element other than carbon. Heteroatoms are typically O, S or N atoms. Examples of heterocyclyl groups include: piperidine, piperazine, morpholine, pyrrolidine, tetrahydrofuran, azetidine, oxirane, or aziridine, and the like.

"Bicyclic heterocyclyl," "bicyclic heterocycle" or "bicyclic heterocyclic" refers to a heterocyclic ring fused to another ring system. The fusion may be bridged or unbridged.

"Heteroaryl" unless otherwise indicated, means a monocyclic-aromatic ring or ring system, wherein the ring or ring system is made up of a specified number of atoms when noted, and which contains at least one heteroatom selected from O, S and N or a specified number and selection of heteroatoms when noted. Examples include, but are not limited to, pyrrolyl, isoxazolyl, isothiazolyl, pyrazolyl, pyridyl, oxazolyl, oxadiazolyl, 1,3,4-oxadiazolyl-2(3H)-one, thiadiazolyl, thiazolyl, imidazolyl, triazolyl, tetrazolyl, furanyl, triazinyl, thienyl, pyridinyl, pyrimidinyl, pyridazinyl, pyrazinyl, and the like.

"Fused heteroaryl" means a heteroaryl fused to an aryl, cycloalkyl, heterocyclyl, or another heteroaryl. Fused heteroaryl ring can be a 7-, 8-, 9-, 10, or 11-membered ring or combinations thereof. One such combination is from a 7- to 10 membered ring system. Examples include indole, 4,5,6,7-tetrahydro-1H-indole, 1H-benzo[d][1,2,3]triazole, benzo[d]isoxazole, and [1,2,4]triazolo[1,5-a]pyridine.

"Oxo" means an oxygen linked to an atom by a double bond. An example of an oxo group is a doubly bonded oxygen in a ketone, sulfoxide, sulfone and sulfate.

"Hydroxyalkyl" means an alkyl group having one or more hydrogen atoms replaced by hydroxyl groups.

When any variable (e.g., $R^5$ etc.) occurs more than one time in any constituent or in Formulas I to I-d or other generic Formulae herein, its definition on each occurrence is independent of its definition at every other occurrence. Combinations of substituents and/or variables are permissible only if such combinations result in stable compounds. In choosing compounds of the present invention, one of ordinary skill in the art will recognize that the various substituents, i.e. $R^5$ etc., are to be chosen in conformity with well-known principles of chemical structure connectivity and stability. Unless expressly stated to the contrary, substitution by a named substituent is permitted on any atom in a ring (e.g., aryl, a heteroaryl ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Unless expressly depicted or described otherwise, variables depicted in a structural formula with a "floating" bond, such as $R^6$, are permitted on any available carbon atom in the ring to which the variable is attached.

Compounds of structural Formulas I to I-d may contain one or more asymmetric centers and can thus occur as racemates and racemic mixtures, single enantiomers, diastereoisomeric mixtures and individual diastereoisomers. Centers of asymmetry that are present in the compounds of Formulas I to I-d can all independently of one another have S configuration or R configuration. The compounds of this invention include all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The present invention is meant to comprehend all such stereo-isomeric forms of the compounds of structural Formulas I to I-d.

Compounds of structural Formulas I to I-d may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration. Alternatively, any stereoisomer or isomers of a compound of Formulas I to I-d may be obtained by stereospecific synthesis using optically pure starting materials or reagents of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

For compounds of Formulas I to I-d described herein which contain olefinic double bonds, unless specified otherwise, they are meant to include both E and Z geometric isomers.

Some of the compounds described herein may exist as tautomers which have different points of attachment of hydrogen accompanied by one or more double bond shifts. For example, a ketone and its enol form are keto-enol tautomers. The individual tautomers as well as mixtures thereof are encompassed with compounds of Formulas I to I-d of the present invention.

In the compounds of structural Formulas I to I-d, the atoms may exhibit their natural isotopic abundances, or one or more of the atoms may be artificially enriched in a particular isotope having the same atomic number, but an atomic mass or mass number different from the atomic mass or mass number predominately found in nature. The present invention as described and claimed herein is meant to include all suitable isotopic variations of the compounds of structural Formulas I to I-d and embodiments thereof. For example, different isotopic forms of hydrogen (H) include protium ($^1H$) and deuterium ($^2H$, also denoted herein as D). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples.

Isotopically-enriched compounds within structural Formulas I to I-d, can be prepared without undue experimentation by conventional techniques well known to those skilled in the art or by processes analogous to those described in the Schemes and Examples herein using appropriate isotopically-enriched reagents and/or intermediates.

It will be understood that the compounds of structural Formulas I to I-d may be prepared as pharmaceutically acceptable salts or as salts that are not pharmaceutically acceptable when they are used as precursors to the free compounds or their pharmaceutically acceptable salts or in other synthetic manipulations. The compounds of the present invention, including the compounds of the Examples, may also include all salts of the compounds of Formulas I to I-d which, owing to low physiological compatibility, are not directly suitable for use in pharmaceuticals but which can be used, for example, as intermediates for chemical reactions or for the preparation of physiologically acceptable salts.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, benzenesulfonate, benzoate, bicarbonate, bisulfate, bitartrate, borate, bromide, butyrate, camphorate, camphorsulfonate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, methanesulfonate, mucate, napsylate, nitrate, N-methylglucamine ammonium salt, oleate, oxalate, pamoate (embonate), palmitate, pantothenate, phosphate/diphosphate, polygalacturonate, propionate, salicylate, stearate, sulfate, subacetate, succinate, tannate, tartrate, teoclate, thiocyanate, tosylate, triethiodide, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. In one embodiment, the salt of acidic compounds is as follows, the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. If the compounds of Formulas I to I-d simultaneously contain acidic and basic groups in the molecule the invention also includes, in addition to the salt forms mentioned, inner salts or betaines (zwitterions). Salts can be obtained from the compounds of Formulas I to I-d by customary methods which are known to the person skilled in the art, for example by combination with an organic or inorganic acid or base in a solvent or dispersant, or by anion exchange or cation exchange from other salts. Furthermore, compounds of the present invention may exist in amorphous form and/or one or more crystalline forms, and as such all amorphous and crystalline forms and mixtures thereof of the compounds of Formulas I to I-d, including the Examples, are intended to be included within the scope of the present invention. In addition, some of the compounds of the instant invention may form solvates with water (i.e., a hydrate) or common organic solvents such as but not limited to ethyl acetate. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid (—COOH) group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO⁻ depending on the pH of the fluid or tissue where conversion takes place) or hydroxy form particularly in vivo and as such are encompassed within the scope of this invention. Included are those esters and acyl groups known in the art for modifying the solubility or hydrolysis characteristics for use as sustained-release or prodrug formulations. Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed.

Accordingly, the present invention includes compounds within the generic structural formulas, embodiments and specific compounds described in the Examples as well as salts, all possible stereoisomers and tautomers, physical forms (e.g., amorphous and crystalline forms), solvate and hydrate forms thereof and any combination of these forms, as well as the salts, pro-drug forms thereof, and salts of pro-drug forms thereof, where such forms are possible unless specified otherwise, The present invention also relates to processes for the preparation of the compounds of Formulas I to I-d which are described in the following and by which the compounds of the invention are obtainable.

The terms "therapeutically effective (or efficacious) amount" and similar descriptions such as "an amount efficacious for treatment" are intended to mean that amount of a pharmaceutical drug that will alleviate the symptoms of the disorder, condition or disease being treated (i.e., disorder, condition or disease associated with DGAT2 activity) in an animal or human. The terms "prophylactically effective (or efficacious) amount" and similar descriptions such as "an amount efficacious for prevention" are intended to mean that amount of a pharmaceutical drug that will prevent or reduce the symptoms or occurrence of the disorder, condition or disease being treated (i.e., disorder, condition or disease associated with DGAT2 activity) in an animal or human. The dosage regimen utilizing a compound of the instant invention is selected in accordance with a variety of factors including type, species, age, weight, sex and medical condition of the patient; the severity of the condition to be treated; the potency of the compound chosen to be administered; the route of administration; and the renal and hepatic function of the patient. A consideration of these factors is well within the purview of the ordinarily skilled clinician for the purpose of determining the therapeutically effective or prophylactically effective dosage amount needed to prevent, counter, or arrest the progress of the condition. It is understood that a specific daily dosage amount can simultaneously be both a therapeutically effective amount, e.g., for treatment of hepatic steatosis, diabetes mellitus, obesity, hyperlipidemia, hypercholesterolemia, and a prophylactically effective amount, e.g., for prevention of atherosclerosis.

Disorders, conditions and diseases which can be treated or prevented by inhibiting DGAT2 by using the compounds of Formulas I to I-d are, for example, diseases such as hyperlipidemia, type I diabetes, type II diabetes mellitus, coronary heart disease, ischemic stroke, restenosis, peripheral vascular disease, intermittent claudication, myocardial infarction, dyslipidemia, post-prandial lipemia, obesity, osteoporosis, hypertension, congestive heart failure, left ventricular hypertrophy, peripheral arterial disease, diabetic retinopathy, diabetic nephropathy, glomerulosclerosis, chronic renal failure, diabetic neuropathy, metabolic syndrome, syndrome X, coronary heart disease, angina pectoris, thrombosis, atherosclerosis, myocardial infarction, transient ischemic attacks, stroke, hyperglycemia, hyperinsulinemia, hypertriglyceridemia, hypertriglyceridemia, insulin resistance, impaired glucose tolerance, erectile dysfunction, skin and connective tissue disorders, hyper-apo B lipoproteinemia, non-alcoholic steatohepatitis (NASH), non-alcoholic fatty liver disease, cardiorenal diseases such as chronic kidney diseases and heart failure, and related diseases and conditions.

The compounds of Formulas I to I-d and their pharmaceutically acceptable salts can be administered to animals, preferably to mammals, and in particular to humans, as pharmaceuticals by themselves, in mixtures with one another or in the form of pharmaceutical preparations. The term "patient" includes animals, preferably mammals and especially humans, who use the instant active agents for the prevention or treatment of a medical condition. Administering of the drug to the patient includes both self-administration and administration to the patient by another person.

The patient may be in need of, or desire, treatment for an existing disease or medical condition, or may be in need of or desire prophylactic treatment to prevent or reduce the risk of occurrence of said disease or medical condition. As used herein, a patient "in need" of treatment of an existing condition or of prophylactic treatment encompasses both a determination of need by a medical professional as well as the desire of a patient for such treatment.

Furthermore, a subject of the present invention are pharmaceutical preparations (or pharmaceutical compositions) which comprise as active component a therapeutically effective dose of at least one compound of Formulas I to I-d and/or a pharmaceutically acceptable salt thereof and a customary pharmaceutically acceptable carrier, i.e., one or more pharmaceutically acceptable carrier substances and/or additives.

Thus, a subject of the invention are, for example, said compound and its pharmaceutically acceptable salts for use as a pharmaceutical, pharmaceutical preparations which comprise as active component a therapeutically effective dose of said compound and/or a pharmaceutically acceptable salt thereof and a customary pharmaceutically acceptable carrier, and the uses of said compound and/or a pharmaceutically acceptable salt thereof in the therapy or prophylaxis of the above mentioned syndromes as well as their use for preparing medicaments for these purposes. The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of Formulas I to I-d and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the active compounds and carriers, the pharmaceutical preparations can also contain customary additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the active compound of Formulas I to I-d and/or of a pharmaceutically acceptable salt thereof to be administered depends on the individual case and is, as is customary, to be adapted to the individual circumstances to achieve an optimum effect. Thus, it depends on the nature and the severity of the disorder, condition or disease to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of Formulas I to I-d.

One or more additional pharmacologically active agents may be administered in combination with a compound of Formulas I to I-d. An additional active agent (or agents) is intended to mean a pharmaceutically active agent (or agents) that is active in the body, including pro-drugs that convert to pharmaceutically active form after administration, which are different from the compound of Formulas I to I-d, and also includes free-acid, free-base and pharmaceutically acceptable salts of said additional active agents. Generally, any suitable additional active agent or agents, including but not limited to anti-hypertensive agents, anti-atherosclerotic agents such as a lipid modifying compound, anti-diabetic agents and/or anti-obesity agents may be used in any combination with the compound of Formulas I to I-d in a single dosage formulation (a fixed dose drug combination), or may be administered to the patient in one or more separate dosage formulations which allows for concurrent or sequential administration of the active agents (co-administration of the separate active agents).

Examples of additional active agents which may be employed include but are not limited to angiotensin converting enzyme inhibitors (e.g., alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists (e.g., losartan i.e., COZAAR®, valsartan, candesartan, olmesartan, telmesartan and any of these drugs used in combination with hydrochlorothiazide such as HYZAAR®); neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives, peptidyl amino diols and peptidyl beta-aminoacyl aminodiol carbamates, and small molecule renin inhibitors (including diol sulfonamides and sulfinyls), N-morpholino derivatives, N-heterocyclic alcohols and pyrolimidazolones; also, pepstatin derivatives and fluoro- and chloro-derivatives of statone-containing peptides, enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, phosphodiesterase-5 inhibitors (e.g. sildenafil, tadalfil and vardenafil), vasodilators, calcium channel blockers (e.g., amlodipine, nifedipine, veraparmil, diltiazem, gallopamil, niludipine, nimodipins, nicardipine), potassium channel activators (e.g., nicorandil, pinacidil, cromakalim, minoxidil, aprilkalim, loprazolam), diuretics (e.g., hydrochlorothiazide), sympatholitics, beta-adrenergic blocking drugs (e.g., propranolol, atenolol, bisoprolol, carvedilol, metoprolol, or metoprolol tartate), alpha adrenergic blocking drugs (e.g., doxazosin, prazosin, terazosin or alpha methyldopa) central alpha adrenergic agonists, peripheral vasodilators (e.g. hydralazine); lipid lowering agents e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), fluvastatin (particularly the sodium salt sold in LESCOL®), cerivastatin, and pitavastatin; a cholesterol absorption inhibitor such as ezetimibe (ZETIA®) and ezetimibe in combination with any other lipid lowering agents such as the HMG-CoA reductase inhibitors noted above and particularly with simvastatin (VYTORIN®) or with atorvastatin calcium; niacin in immediate-release or controlled release forms and/or with an HMG-CoA reductase inhibitor; niacin receptor agonists such as acipimox and acifran, as well as niacin receptor partial agonists; metabolic altering agents including insulin and insulin mimetics (e.g., insulin degludec, insulin glargine, insulin lispro), dipeptidyl peptidase-IV (DPP-4) inhibitors (e.g., sitagliptin, alogliptin, omarigliptin, linagliptin, vildagliptin); insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); insulin or insulin analogs (e.g., insulin detemir, insulin glulisine, insulin degludec, insulin glargine, insulin lispro and inhalable formulations of each); leptin and leptin derivatives and agonists; amylin and amylin analogs (e.g., pramlintide); sulfonylurea and non-sulfonylurea insulin secretagogues (e.g., tolbutamide, glyburide, glipizide, glimepiride, mitiglinide, meglitinides, nateglinide and repaglinide); α-glucosidase inhibitors (e.g., acarbose, voglibose and miglitol); glucagon receptor antagonists (e.g., MK-3577, MK-0893, LY-2409021 and KT6-971); incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); bile acid sequestering agents (e.g., colestilan, colestimide, colesevalam hydrochloride, colestipol, cholestyramine, and dialkylaminoalkyl derivatives of a cross-linked dextran), acyl CoA:cholesterol acyltransferase inhibitors, (e.g., avasimibe); antiobesity compounds; agents intended for use in inflammatory conditions, such as aspirin, non-steroidal anti-inflammatory drugs or NSAIDs, glucocorticoids, and selective cyclooxygenase-2 or COX-2 inhibitors; glucokinase activators (GKAs) (e.g., AZD6370); inhibitors of 11β-hydroxysteroid dehydrogenase type 1, (e.g., such as those disclosed in U.S. Pat. No. 6,730,690, and LY-2523199); CETP inhibitors (e.g., anacetrapib, torcetrapib, and evacetrapib); inhibitors of fructose 1,6-bisphosphatase, (e.g., such as those disclosed in U.S. Pat. Nos. 6,054,587; 6,110,903; 6,284,748; 6,399,782; and 6,489,476); inhibitors of acetyl CoA carboxylase-1 or 2 (ACC1 or ACC2); AMP-activated Protein Kinase (AMPK) activators; other agonists of the G-protein-coupled receptors: (i) GPR-109, (ii) GPR-119 (e.g., MBX2982 and PSN821), and (iii) GPR-40 (e.g., TAK875); SSTR3 antagonists (e.g., such as those disclosed in WO 2009/001836); neuromedin U receptor agonists (e.g., such as those disclosed in WO 2009/042053, including, but not limited to, neuromedin S (NMS)); SCD modulators; GPR-105 antagonists (e.g., such as those disclosed in WO 2009/000087); SGLT inhibitors (e.g., ASP1941, SGLT-3, empagliflozin, dapagliflozin, canagliflozin, BI-10773, ertugliflozin, remogliflozin, TS-071, tofogliflozin, ipragliflozin, and LX-4211); inhibitors of acyl coenzyme A:diacylglycerol acyltransferase 1 and 2 (DGAT-1 and DGAT-2); inhibitors of fatty acid synthase; inhibitors of acyl coenzyme A:monoacylglycerol acyltransferase 1 and 2 (MGAT-1 and MGAT-2); agonists of the TGR5 receptor (also known as GPBARl, BG37, GPCR19, GPR131, and M-BAR); ileal bile acid transporter inhibitors; PACAP, PACAP mimetics, and PACAP receptor 3 agonists; PPAR agonists; protein tyrosine phosphatase-1B (PTP-1B) inhibitors; IL-1b antibodies, (e.g., XOMA052 and canakinumab); and bromocriptine mesylate and rapid-release formulations thereof; or with other drugs beneficial for the prevention or the treatment of the above-mentioned diseases including nitroprusside and diazoxide the free-acid, free-base, and pharmaceutically acceptable salt forms of the above active agents where chemically possible.

The following examples are provided so that the invention might be more fully understood. Unless otherwise indicated, the starting materials are commercially available. They should not be construed as limiting the invention in any way.

Several methods for preparing the compounds of this invention are described in the following Schemes and Examples. Starting materials and intermediates are purchased, made from known procedures, or as otherwise illustrated. For stereoisomers, enantiomer A refers to the faster/earlier eluting enantiomer and enantiomer B refers to the slower/later eluting enantiomer at the point of separation and this nomenclature is maintained through the remainder of a synthetic sequence for a given enantiomeric series regardless of the possibility that subsequent intermediates and final compounds may have the same or opposite orders of elution. Some frequently applied routes to the compounds of Formulas I to I-d are also described by the Schemes as follows. In some cases the order of carrying out the steps of reaction schemes may be varied to facilitate the reaction or to avoid unwanted reaction products. The "R" groups in the Schemes correspond to the variables defined in Formulas I to I-d at the same positions on the structures.

1. General Synthetic Schemes:

Scheme A

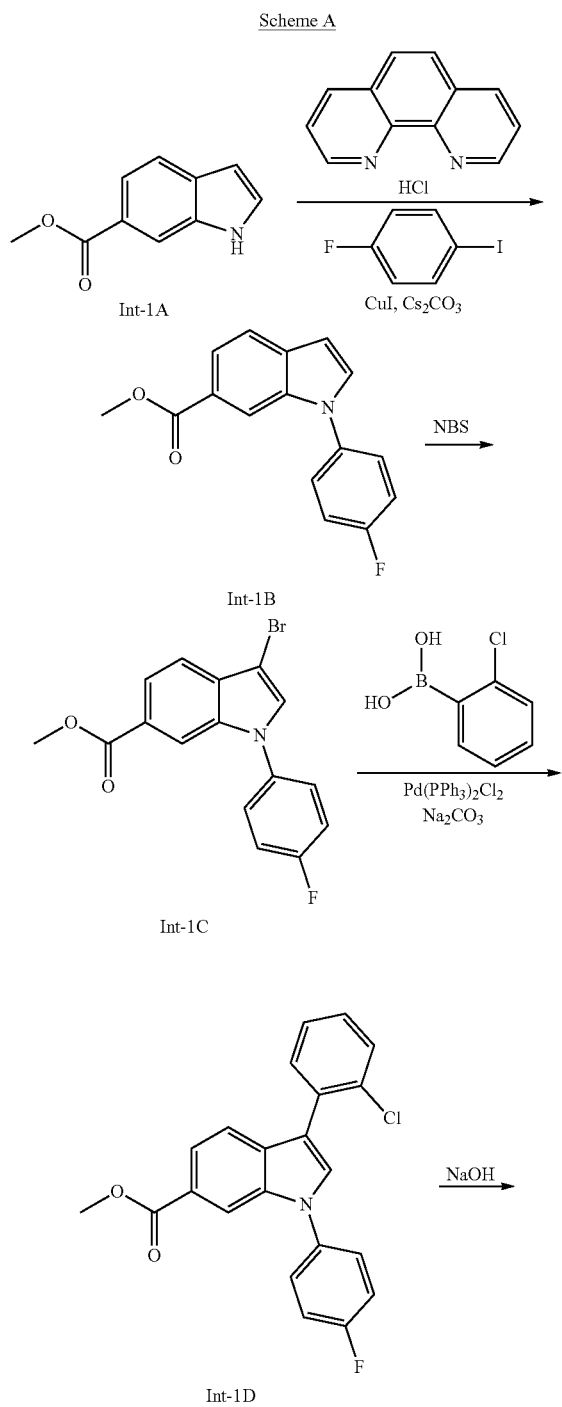

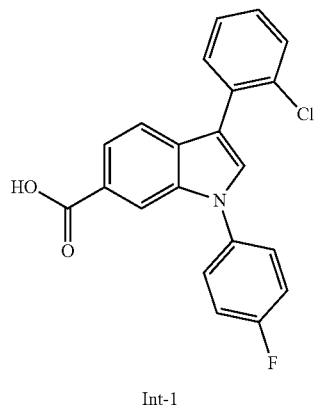

Int-1

Int-1 is prepared according to Scheme A starting with indole ester Int-1A which is N-arylated to give indole Int-1B. Bromination of Int-1B lead to Int-1C, the latter is used in a Suzuki coupling reaction to afford ester Int-1D. Hydrolysis of Int-1D provides Int-1.

Scheme B

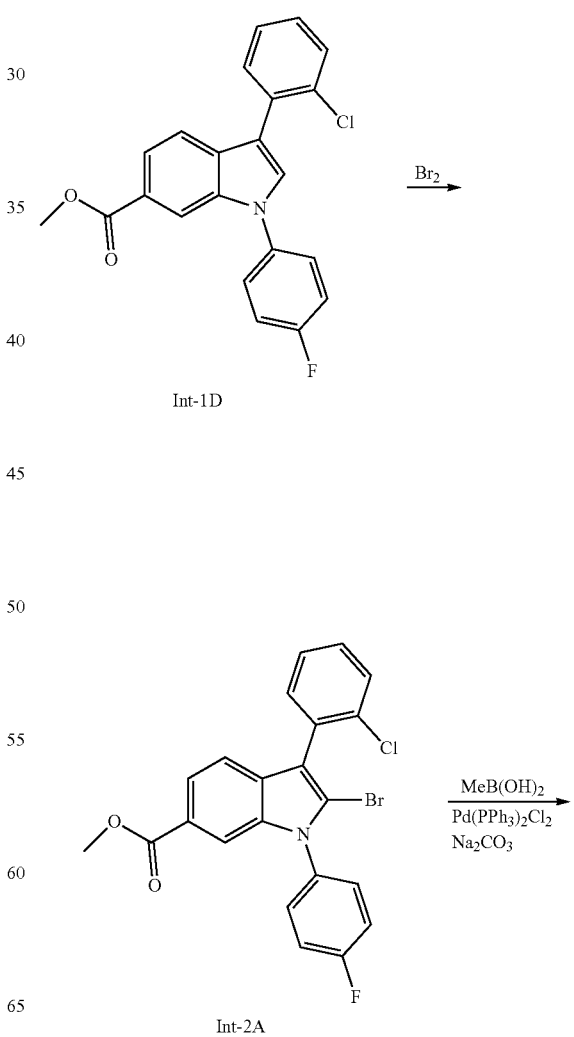

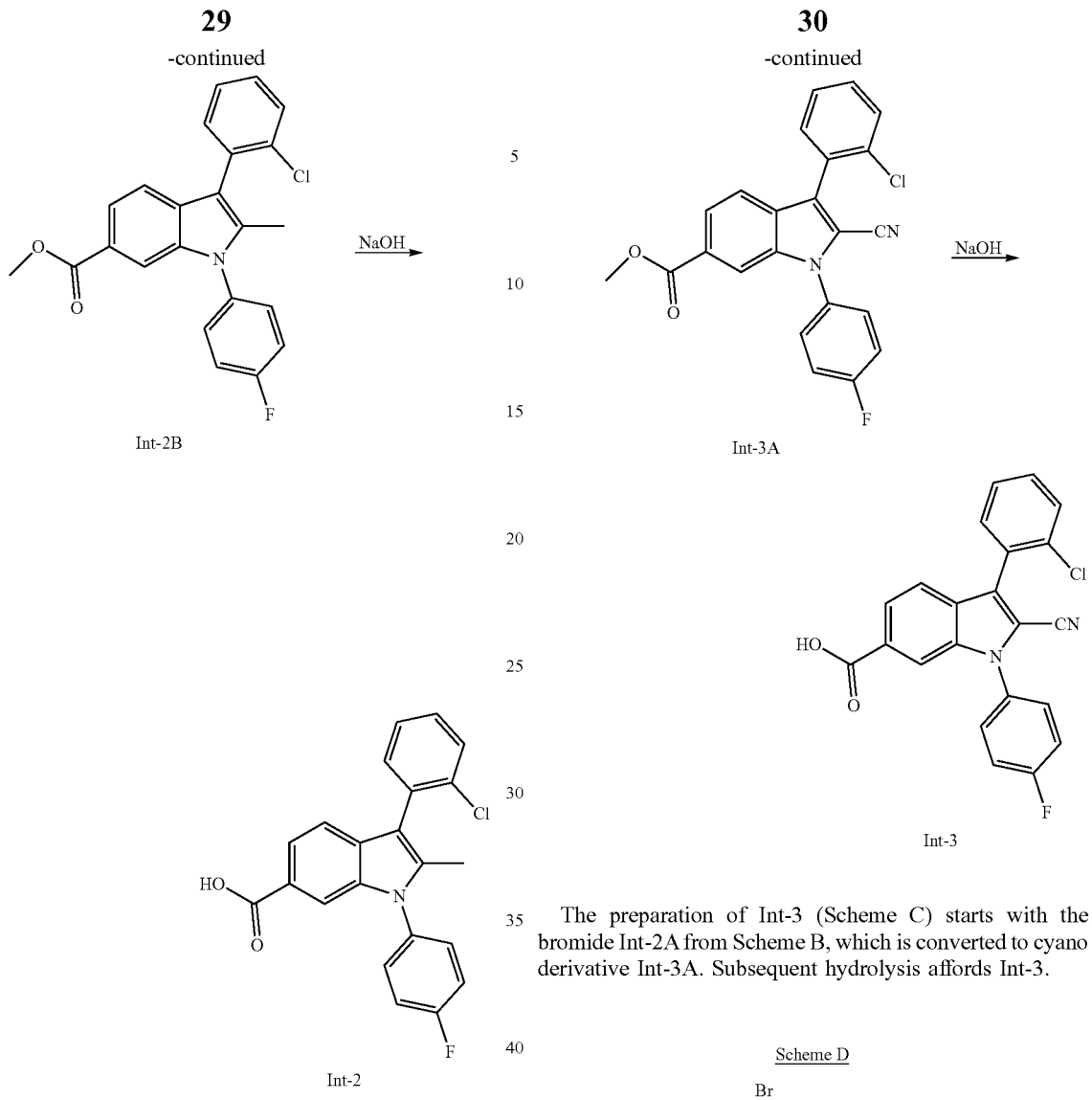
The preparation of Int-2 is shown in Scheme B. Indole Int-1D is brominated at the 2-position to give bromide Int-2A, which upon Suzuki coupling gives the 2-methyl indole Int-2B. Int-2B is hydrolyzed to provide Int-2.
The preparation of Int-3 (Scheme C) starts with the bromide Int-2A from Scheme B, which is converted to cyano derivative Int-3A. Subsequent hydrolysis affords Int-3.
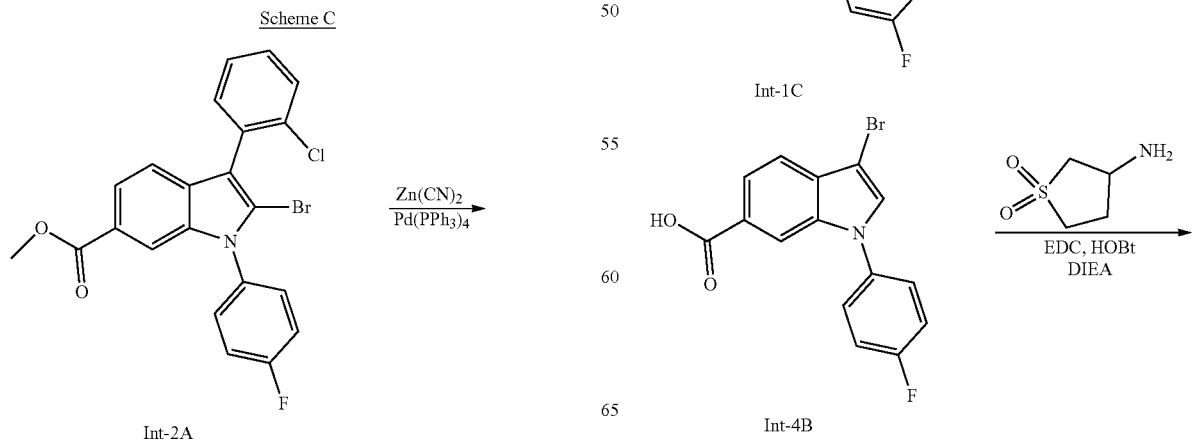

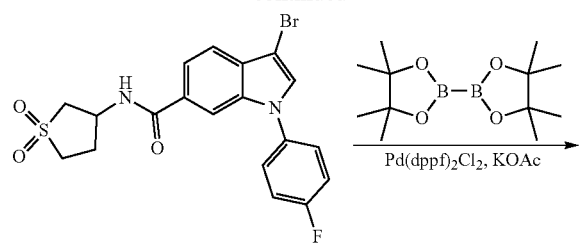

Int-4C

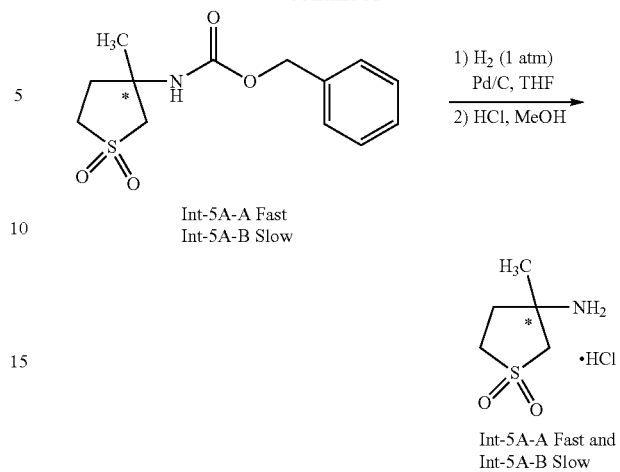

Int-5A-A Fast
Int-5A-B Slow

Int-5A-A Fast and
Int-5A-B Slow

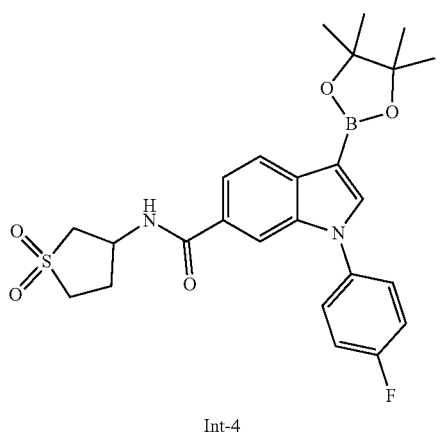

Int-4

In Scheme D, hydrolysis of ester Int-1C provides acid Int-4B, which is coupled with the racemic amine to give bromo amide Int-4C. The bromide Int-4C is converted to a boronic ester using standard procedures to afford Int-4.

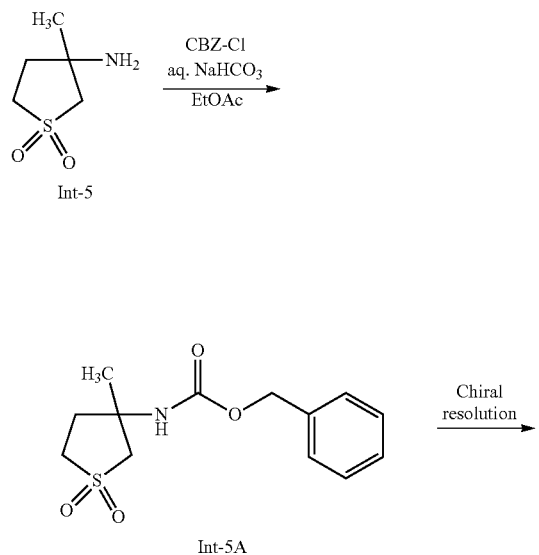

In Scheme E, racemic amine Int-5 was protected with CBZ to afford Int-5A, which was resolved to give two enantiomers, Int-5A-A (fast eluting) and Int-5A-B (slow-eluting). Each of these enantiomers was deprotected to give Int-5-A (fast-eluting) Int-5-B (slow-eluting). Throughout the synthetic schemes and examples, abbreviations and acronyms may be used with the following meanings unless otherwise indicated:

ACN, MeCN=acetonitrile; AcOH=acetic acid; Aq.=aqueous; CBZ-Cl=benzyl chloroformate; CELITE=diatomaceous earth; $CF_3$=trifluoromethyl; DCM=dichloromethane; DIEA=diisopropylethylamine or Hunig's base; DMF=N,N-dimethylformamide; DMSO=dimethylsulfoxide; dppf=1,1'-bis(diphenylphosphino)ferrocene; EDC=1-Ethyl-3-(3-dimethylaminopropyl) carbodiimide; Et=ethyl; $Et_3$N=triethylamine; EtOAc=ethyl acetate; EtOH=ethanol; g=gram; h, hr=hour; HATU=1-[bis(dimethylamino)methylene]-1H-1,2,3-triazolo[4,5-b]pyridinium 3-oxid hexafluorophosphate; HCl=hydrogen chloride; HOBt=Hydroxybenzotriazole; HPLC=High pressure liquid chromatography; Int.=intermediate; KOAc=potassium acetate; LCMS, LC/MS=liquid chromatography-mass spectrometry; min, min.=minute; M=Molar; Me=methyl; mmol=millimole or millimolar; ACN=acetonitrile; MeOH=methanol; μL=microliter; μmol=micromole; mL=milliliter; mp, m.p.=melting point; N=Normal; NBS=N-bromosuccinimide; NMR=nuclear magnetic resonance; Pd/C=palladium on carbon; $Pd(PPh_3)_4$=tetrakis(triphenylphosphine)palladium(0); $Pd(dppf)Cl_2$=dichloro((1,1'-bis(diphenylphosphino)ferrocene) palladium (II); $Pd(PPh_3)_2Cl_2$=dichlorobis(triphenylphosphine)palladium(II) or bis(triphenylphosphine) palladium (II) chloride; $Pd_2(dba)_3$=tris(dibenzylideneacetone)dipalladium (0); Ph=phenyl; PPA=polyphosphoric acid; Pr=propyl; RP-HPLC=reverse phase HPLC; rt, RT=room temperature; sat., sat'd=saturated; SFC=supercritical fluid chromatography; TFA=trifluoroacetic acid; THF=tetrahydrofuran.

The following examples are provided so that the invention might be more fully understood. They should not be construed as limiting the invention in any way. The preparation of Intermediates and examples is described below:

Intermediate 1

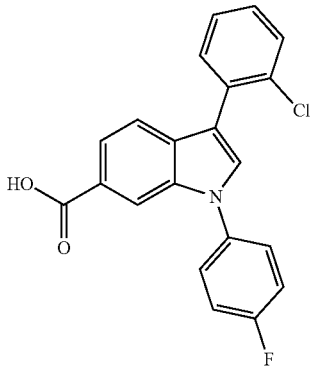

3-(2-Chlorophenyl)-1-(4-fluorophenyl)-1H-indole-6-carboxylic acid

Step A: Methyl 1-(4-fluorophenyl)-1H-indole-6-carboxylate

A mixture of methyl 1H-indole-6-carboxylate (1 g, 5.71 mmol), copper (I) iodide (0.109 g, 0.571 mmol), 1,10-phenanthroline hydrochloride (0.247 g, 1.142 mmol), 1-fluoro-4-iodobenzene (1.394 g, 6.28 mmol), and $Cs_2CO_3$ (4.65 g, 14.27 mmol) in toluene (35 ml) was heated at 110° C. for 20 h. After removing the volatiles, the residue was purified by silica gel chromatography (EtOAc/hexanes) to afford the title compound. m/z 270.0 (M+1).

Step B: Methyl 3-bromo-1-(4-fluorophenyl)-1H-indole-6-carboxylate

To a solution of methyl 1-(4-fluorophenyl)-1H-indole-6-carboxylate (334 mg, 1.240 mmol) in DCM (10 ml) was added NBS (265 mg, 1.488 mmol), and the resulting solution stirred at rt for 1 h. After concentrating, the residue was purified by silica gel chromatography (EtOAc/hexanes) to afford the title compound. m/z 347.9/349.9 (M+1).

Step C: Methyl 3-(2-chlorophenyl)-1-(4-fluorophenyl)-1H-indole-6-carboxylate A mixture of 2-chlorophenyl boronic acid (100 mg, 0.638 mmol), methyl 3-bromo-1-(4-fluorophenyl)-1H-indole-6-carboxylate (171 mg, 0.491 mmol), bis(triphenylphosphine) palladium (II) dichloride (34.5 mg, 0.049 mmol), and 1 M aq. $Na_2CO_3$ (1.965 ml, 1.965 mmol) in dioxane (10 mL) was heated at 150° C. in a microwave reactor for 30 min. After filtration, the filtrate was concentrated in vacuo, and the residue was purified by RP-HPLC using ACN/water (0.05% TFA) to give the title compound. m/z 380.0 (M+1).

Step D: 3-(2-chlorophenyl)-1-(4-fluorophenyl)-1H-indole-6-carboxylic acid

To a solution of methyl 3-(2-chlorophenyl)-1-(4-fluorophenyl)-1H-indole-6-carboxylate (1.09 g, 2.87 mmol) in a mixture of THF/MeOH/water (3:1:1, 10 mL) was added 5 N aq. NaOH (5.74 ml, 28.7 mmol), and the resulting solution was stirred at rt overnight. The reaction mixture was concentrated in vacuo, and the aqueous residue was acidified by 22 N HCl to pH 3. The mixture was extracted with EtOAc three times, and the combined organic phase was dried over anhydrous $Na_2SO_4$. The dried organic phase was concentrated in vacuo to give the title compound. m/z 366.0 (M+1).

Intermediate 2

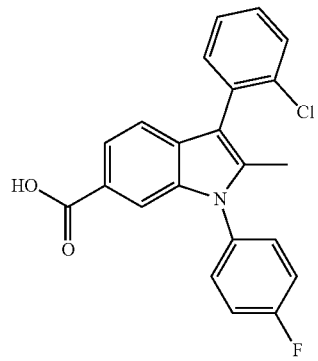 [SMILES: Cc1c(-c2ccccc2Cl)c2ccc(C(=O)O)cc2n1-c1ccc(F)cc1]

3-(2-Chlorophenyl)-1-(4-fluorophenyl)-2-methyl-1H-indole-6-carboxylic acid

Step A: Methyl 2-bromo-3-(2-chlorophenyl)-1-(4-fluorophenyl)-1H-indole-6-carboxylate To a solution of methyl 3-(2-chlorophenyl)-1-(4-fluorophenyl)-1H-indole-6-carboxylate (512 mg, 1.348 mmol) in AcOH (5 mL) was added bromine (72.9 μl, 1.415 mmol) in AcOH (20 mL). The resulting solution was stirred at rt for 1 h, then heated at 80° C. for 2 h. The reaction mixture was concentrated in vacuo, and the residue was treated with EtOAc. The solids were collected by filtration. Then the filtrate was washed with sat. $Na_2SO_3$, $NaHCO_3$, and dried over anhydrous $Na_2SO_4$. The filtrate was concentrated in vacuo and the resulting residue was combined with the previously collected solids to give the title compound. m/z 457.9/459.9 (M+1).

Step B: Methyl 3-(2-chlorophenyl)-1-(4-fluorophenyl)-2-methyl-1H-indole-6-carboxylate A solution of methyl 2-bromo-3-(2-chlorophenyl)-1-(4-fluorophenyl)-1H-indole-6-carboxylate (43 mg, 0.094 mmol), methylboronic acid (11.22 mg, 0.187 mmol), 1 N aq. $Na_2CO_3$ (469 μl, 0.469 mmol) in dioxane (2 mL) was flushed with $N_2$ followed by addition of bis(triphenylphosphine) palladium (II) dichloride (6.58 mg, 9.37 μmol). The resulting mixture was microwaved at 150° C. for 30 min. After filtration the filtrate was concentrated in vacuo, and the residue was purified by silica gel chromatography (EtOAc/hexanes) to give the title compound m/z 394.1 (M+1).

Step C: 3-(2-Chlorophenyl)-1-(4-fluorophenyl)-2-methyl-1H-indole-6-carboxylic acid To a solution of methyl 3-(2-chlorophenyl)-1-(4-fluorophenyl)-2-methyl-1H-indole-6-carboxylate (36 mg, 0.091 mmol) in a mixture of MeOH/THF/water (1:1:1, 3 mL) was added 5 N aq. NaOH (366 µl, 1.828 mmol), and the resulting solution was heated at 50° C. for 2 h. The reaction mixture was concentrated in vacuo to give an aqueous mixture. The aqueous mixture was acidified to pH 2 by 1N HCl, then extracted with DCM (3 times). The combined organic phase was dried over anhydrous Na$_2$SO$_4$ and concentrated in vacuo to give the title compound. m/z 380.1 (M+1).

Intermediate 3

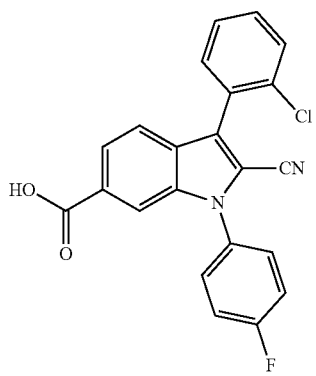 [SMILES: N#Cc1c(-c2ccccc2Cl)c2ccc(C(=O)O)cc2n1-c1ccc(F)cc1]

3-(2-Chlorophenyl)-2-cyano-1-(4-fluorophenyl)-1H-indole-6-carboxylic acid

Step A: Methyl 3-(2-chlorophenyl)-2-cyano-1-(4-fluorophenyl)-1H-indole-6-carboxylate A mixture of methyl 2-bromo-3-(2-chlorophenyl)-1-(4-fluorophenyl)-1H-indole-6-carboxylate (60 mg, 0.131 mmol) and Zn(CN)$_2$ (30.7 mg, 0.262 mmol) in DMF (6 mL) was flushed with N$_2$ followed by addition of tetrakis(triphenylphosphine) palladium (0) (15.12 mg, 0.013 mmol). The resulting mixture was microwaved at 150° C. for 30 min. The reaction mixture was filtered, and the filtrate was purified with a RP-HPLC using ACN/water (0.05% TFA) to give the title compound.

Step B: 3-(2-Chlorophenyl-2-cyano-1-(4-fluorophenyl)-1H-indole-6-carboxylic acid To a solution of methyl 3-(2-chlorophenyl)-2-cyano-1-(4-fluorophenyl)-1H-indole-6-carboxylate (42 mg, 0.104 mmol) in a mixture of THF/MeOH/water (3:1:1, 5 mL) was added 5 N aq. NaOH (2 mL, 10.00 mmol), and the resulting reaction mixture was stirred at rt for 2 h. The reaction mixture was concentrated in vacuo to give an aqueous mixture. The aqueous mixture was acidified to pH 2, then extracted with DCM three times. The combined DCM phase was dried over anhydrous Na$_2$SO$_4$ and concentrated in vacuo to give the title compound.

Intermediate 4

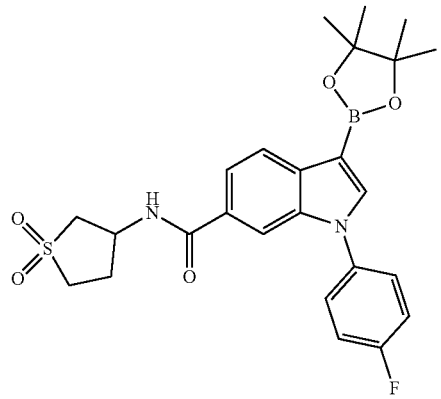 [SMILES: CC1(C)OB(c2cn(-c3ccc(F)cc3)c3cc(C(=O)NC4CCS(=O)(=O)C4)ccc23)OC1(C)C]

N-(1,1-Dioxidotetrahydrothiophen-3-yl)-1-(4-fluorophenyl)-3-(4,4,5,5-tetramethyl-1,3,2-dioxaborolan-2-yl)-1H-indole-6-carboxamide (racemic)

Step A:
3-Bromo-1-(4-fluorophenyl)-1H-indole-6-carboxylic acid

To a solution of methyl 3-bromo-1-(4-fluorophenyl)-1H-indole-6-carboxylate from Int-1, step 2 (3.77 g, 10.83 mmol) in a mixture of THF/MeOH/water (3:1:1, 100 mL) was added 5 N aq. sodium hydroxide (21.66 ml, 108 mmol) and the resulting solution was stirred at rt for 36 h. The reaction mixture was concentrated in vacuo to give an aqueous mixture. The aqueous mixture was acidified by addition of 5N HCl to pH 3. Then the aqueous mixture was extracted with EtOAc three times. The combined organic phase was washed with brine, dried over anhydrous Na$_2$SO$_4$, and concentrated in vacuo to give the title compound. m/z 333.8/335.8 (M+1).

Step B: 3-Bromo-N-(1,1-dioxidotetrahydrothiophen-3-yl-1-(4-fluorophenyl)-1H-indole-6-carboxamide (racemic)

A solution of 3-bromo-1-(4-fluorophenyl)-1H-indole-6-carboxylic acid (0.7 g, 2.095 mmol), HOBt (0.321 g, 2.095 mmol), and EDC (0.522 g, 2.72 mmol) in DCM (40 mL) was stirred at rt for 11 h before the addition of 3-aminotetrahydrothiophene-1,1-dioxide (racemic) (0.297 g, 2.200 mmol) and DIEA (1.098 ml, 6.28 mmol). The resulting solution was stirred at rt overnight, then diluted with DCM (100 mL). The organic phase was washed with 1N HCl and sat. NaHCO$_3$, and dried over Na$_2$SO$_4$. The dried organic phase was concentrated in vacuo give the title compound. m/z 451.0/453.0 (M+1).

Step C: N-(1,1-Dioxidotetrahydrothiophen-3-yl)-1-(4-fluorophenyl)-3-(4,4,5,5-tetramethyl-1,3,2-dioxaborolan-2-yl)-1H-indole-6-carboxamide (racemic)

A solution of 3-bromo-N-(1,1-dioxidotetrahydrothiophen-3-yl)-1-(4-fluorophenyl)-1H-indole-6-carboxamide (racemic) (0.62 g, 1.374 mmol), bis(pinacolato)diboron (1.744 g, 6.87 mmol), KOAc (0.404 g, 4.12 mmol) in DMSO (10 mL) was flushed with N$_2$ before the addition of Pd(dffp)$_2$Cl$_2$ (0.030 g, 0.041 mmol). The resulting mixture was heated at 100° C. for 6 h. The reaction mixture was partitioned between EtOAc and water, the organic phase was washed with water four times. The organic layer was dried over anhydrous Na$_2$SO$_4$, and concentrated in vacuo, and the residue was purified by silica gel chromatography (EtOAc/hexanes) to give the title compound. m/z 499 (M+1).

Intermediates 5, 5-A (Fast-Eluting) and 5-B (Slow-Eluting)

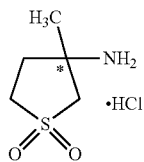

(3R)-3-Amino-3-methyltetrahydrothiophene-1,1-dioxide hydrogen chloride and (3S)-3-amino-3-methyltetrahydrothiophene-1,1-dioxide hydrogen chloride Step A: Benzyl (3-methyl-1,1-dioxidotetrahydrothiophen-3-yl)arbamate 3-Amino-3-methyltetrahydrothiophene-1,1-dioxide (5.018 g, 27.0 mmol) in EtOAc (25 ml) was treated with saturated aqueous NaHCO$_3$ (20 mL) and CBZ-Cl (4.63 ml, 32.4 mmol). The mixture was stirred at rt for 4 h. The organic portion was separated and washed with brine, dried with anhydrous sodium sulfate, filtered and the filtrate was concentrated. The residue was purified on silica gel (0 to 100% EtOAc/hexanes) to afford the title compound. $^1$H NMR (500 MHz, CD$_3$OD) δ 7.29-7.35 (m, 5H); 5.08 (s, 2H); 3.85 (s, 1H); 3.82 (s, 1H); 3.19-3.24 (m, 1H); 3.07 (d, J=13.8 Hz; 1H); 2.58 (br s, 1H); 2.20 (ddd, J=13.9, 10.54, 7.9 Hz; 1H); 1.53 (s, 3H). Chiral resolution using SFC conditions (15% 2:1 MeOH:ACN on an OD or IA column) afforded enantiomer A (fast-eluting) and enantiomer B (slow-eluting).

Step B: 3-Amino-3-methyltetrahydrothiophene-1,1-dioxide hydrogen chloride Int-5-A. (Fast-Eluting) and Int-5-B (Slow-Eluting)

A flask was charged with benzyl (3-methyl-1,1-dioxidotetrahydrothiophen-3-yl)carbamate (enantiomer A, fast-eluting on an OD or IA column) (6.52 g, 23.01 mmol), 10% Pd/C (1.20 g) and EtOAc (100 ml). The flask was purged with nitrogen and then hydrogen. The mixture was stirred under hydrogen (1 atm) for 24 h, filtered through CELITE and the filtrate was concentrated to an oil that was treated with 1.25 M HCl in MeOH (50 mL) and then concentrated to afford 3-amino-3-methyltetrahydrothiophene-1,1-dioxide hydrogen chloride Int-5-A (fast-eluting). $^1$H NMR (500 MHz, D$_2$O) δ 4.76 (s, 3H); 3.47-3.54 (m, 4H); 2.49 (t, J=7.7 Hz; 2H); 1.60 (s, 3H). LCMS m/z 150.0 (M+1). The procedure described above was adapted to prepare Int-5-B (slow-eluting). Note that the designation of fast- and slow-eluting isomers of Int-5-A and Int-5-B refer to the elution order for enantiomers of their benzyl carbamate precursors on the columns specified.

Intermediate 6

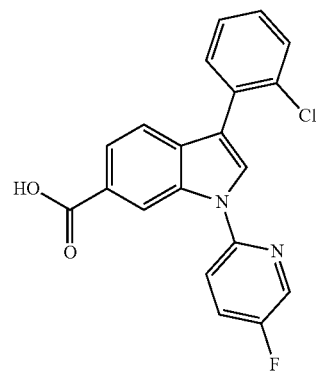 [SMILES: O=C(O)c1ccc2c(-c3ccccc3Cl)cn(-c3ccc(F)cn3)c2c1]

3-(2-Chlorophenyl)-1-(5-fluoropyridin-2-yl)-1H-indole-6-carboxylic acid

The title compound was synthesized by adapting the synthetic procedure used to synthesis Int-1 starting from 1H-indole-6-carboxylate and 2-bromo-5-fluoropyridine. m/z 367.1 (M+1).

Intermediate 7

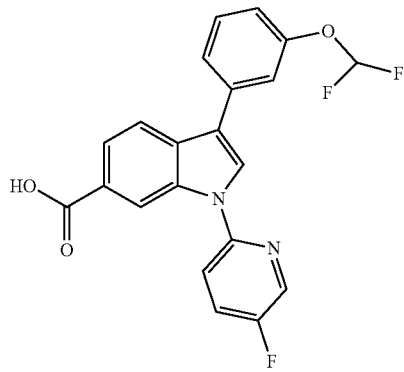 [SMILES: O=C(O)c1ccc2c(-c3cccc(OC(F)F)c3)cn(-c3ccc(F)cn3)c2c1]

3-(3-(Difluoromethoxy)phenyl)-1-(5-fluoropyridin-2-yl)-1H-indole-6-carboxylic acid The title compound was synthesized by adapting the synthetic procedure used to synthesize Int-1 using 2-bromo-5-fluoropyridine in step A and 3-difluoromethoxyphenylboronic acid in step C. m/z 399.0 (M+1).

Intermediate 8

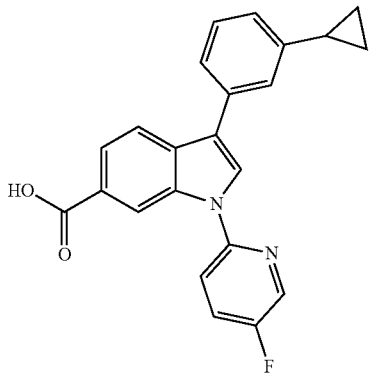 [SMILES: O=C(O)c1ccc2c(-c3cccc(C4CC4)c3)cn(-c3ccc(F)cn3)c2c1]

3-(3-Cyclopropylphenyl)-1-(5-fluoropyridin-2-yl)-1H-indole-6-carboxylic acid

The title compound was synthesized by adapting the synthetic procedure used to synthesize Int-1 using 2-bromo-5-fluoropyridine in step A and 3-cyclopropylphenylboronic acid in step C. m/z 373.2 (M+1).

Intermediate 9

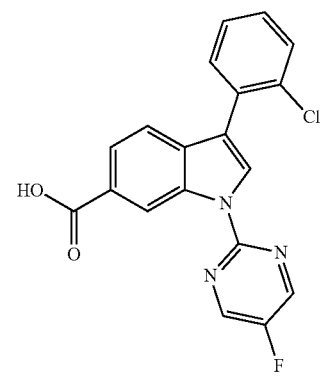

3-(2-Chlorophenyl)-1-(5-fluoropyrimidin-2-yl)-1H-indole-6-carboxylic acid

Step A. Methyl 3-(2-chlorophenyl)-1-(5-fluoropyrimidin-2-yl)-1H-indole-6-carboxylate The title compound was synthesized by adapting the synthetic procedure used to synthesize Int-1, step D starting from methyl 1H-indole-6-carboxylate and 2-chloro-5-fluoropyrimidine. m/z 382.0 (M+1).

Step B. 3-(2-Chlorophenyl)-1-(5-fluoropyrimidin-2-yl)-1H-indole-6-carboxylic acid To a solution of methyl 3-(2-chlorophenyl)-1-(5-fluoropyrimidin-2-yl)-1H-indole-6-carboxylate (130 mg, 0.341 mmol) in AcOH (4 mL) was added hydrochloric acid (37%, 2 mL), and the resulting solution was heated at 90° C. overnight. The residue mixture was concentrated in vacuo, and the residue was purified using RP-HPLC with ACN/water (0.05% TFA) to give the title compound. m/z 368.1 (M+1).

Intermediate 10

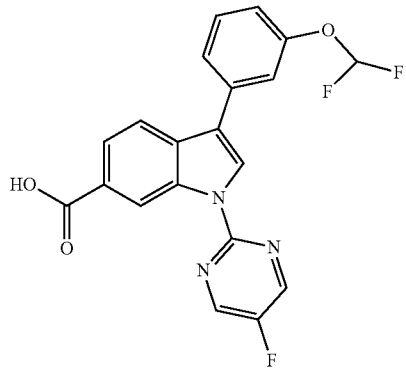 [SMILES: O=C(O)c1ccc2c(-c3cccc(OC(F)F)c3)cn(-c3ncc(F)cn3)c2c1]

3-(3-(Difluoromethoxy)phenyl)-1-(5-fluoropyrimidin-2-yl)-1H-indole-6-carboxylic acid The title compound was synthesized by adapting the synthetic procedure used to synthesize Int-1 using 2-chloro-5-fluoropyrimidine in step A and 3-difluoromethoxyphenylboronic acid in step C. m/z 400.0 (M+1).

Intermediate 11

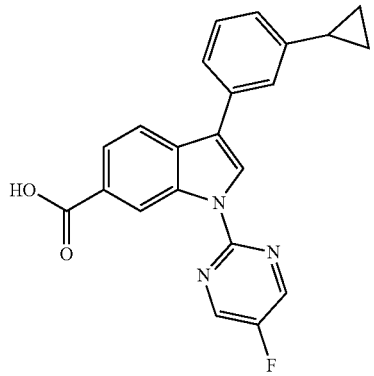 [SMILES: O=C(O)c1ccc2c(-c3cccc(C4CC4)c3)cn(-c3ncc(F)cn3)c2c1]

3-(3-Cyclopropylphenyl)-1-(5-fluoropyrimidin-2-yl)-1H-indole-6-carboxylic acid

The title compound was synthesized by adapting the synthetic procedure used to synthesize Int-1 using 2-chloro-5-fluoropyrimidine in step A and 3-cyclopropylphenylboronic acid in step C. m/z 374.1 (M+1).

Intermediate 12

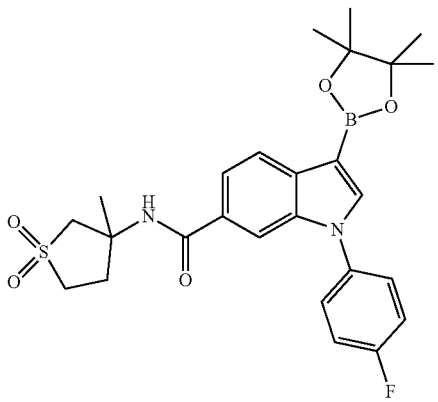 [SMILES: CC1(NC(=O)c2ccc3c(B4OC(C)(C)C(C)(C)O4)cn(-c4ccc(F)cc4)c3c2)CCS(=O)(=O)C1]

1-(4-Fluorophenyl)-N-(3-methyl-1,1-dioxidotetrahydrothiophen-3-yl)-3(4,4,5,5-tetramethyl-1,3,2-dioxaborolan-2-yl)-1H-indole-6-carboxamide (racemic)

The title compound was synthesized following similar procedures those for Int-4 using 3-amino-3-methyltetrahydrothiophene-1,1-dioxide (racemic) instead of 3-aminotetrahydrothiophene 1,1-dioxide (racemic) in Step B. m/z 513.1 (M+1).

Intermediate 13, 13-A (Fast-Eluting) and 13-B (Slow-Eluting)

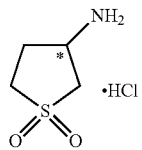

(3R)-3-Aminotetrahydrothiophene-1,1-dioxide hydrogen chloride and (3S)-3-aminotetrahydrothiophene-1,1-dioxide hydrogen chloride Step A: Benzyl (1,1-dioxidotetrahydrothiophen-3-yl)carbamate A flask was charged with 3-aminotetrahydrothiophene-1,1-dioxide hydrochloride (11.6 g, 67.8 mmol), EtOAc (100 ml) and sodium bicarbonate (21.63 g, 257 mmol). Water (100 ml) was added portion-wise over 10 min at rt. CBZ-Cl (14.70 ml, 103 mmol) was added at rt and the mixture was stirred at rt for 16 h. The aqueous layer was separated and discarded, and the organic layer was washed with brine, dried with anhydrous sodium sulfate, and filtered. Then the filtrate was concentrated in vacuo. The resulting residue was purified by silica gel chromatography (10 to 100% EtOAc/hexanes) to afford the title compound. $^1$H NMR (500 MHz, CDCl$_3$) δ 7.33-7.37 (m, 5H); 5.33 (s, 1H); 5.11 (s, 2H); 4.55 (s, 1H); 3.37 (dd, J=13.7 and 7.4 Hz; 1H); 3.20-3.26 (m, 1H); 3.06-3.12 (m; 1H); 3.00 (d, J=13.6 Hz; 1H); 2.51 (dq, J=13.7 and 7.1 Hz; 1H); 2.26 (br s, 1H). Chiral resolution using SFC conditions (25% 2:1 MeOH:MeCN in CO$_2$ on an OJ column) afforded enantiomer A (fast-eluting) and enantiomer B (slow-eluting).

Step B: 3-Aminotetrahydrothiophene-1,1-dioxide hydrochloride (Int-13-A (Fast-Eluting) Int-13-B (Slow-Eluting)

A solution of benzyl (1,1-dioxidotetrahydrothiophen-3-yl)carbamate (enantiomer A, fast eluting on OJ) (2.856 g, 10.60 mmol) in EtOAc (15 ml) was charged into a flask containing 10% Pd/C (300 mg) under N$_2$. The flask was purged with nitrogen and then hydrogen gas. The mixture was stirred under a hydrogen atmosphere (1 atm) for 48 h, and filtered through CELITE. The filtrate was concentrated in vacuo and the resulting material was treated with 1.25 M HCl in MeOH (50 mL), aged 10 min, and then the mixture concentrated in vacuo to afford 3-amino-tetrahydrothiophene-1,1-dioxide hydrogen chloride Int-13-A (fast-eluting). $^1$H NMR (500 MHz, D$_2$O) δ 4.76 (s; 3H); 4.27 (p; J=7.8 Hz; 1H); 3.75 (dd; J=14.4; 8.5 Hz; 1H); 3.49-3.54 (m; 1H); 3.32-3.38 (m; 2H); 2.75-2.82 (m; 1H); 2.32-2.40 (m; 1H). The procedure described above was adapted to prepare Int-13-B (slow-eluting) from benzyl (1,1-dioxidotetrahydrothiophen-3-yl)carbamate (enantiomer B, slow-eluting). Note that the designation of fast- and slow-eluting isomers of Int-13 refers to the elution order for enantiomers of their benzyl carbamate precursors on the OJ column.

Example 1

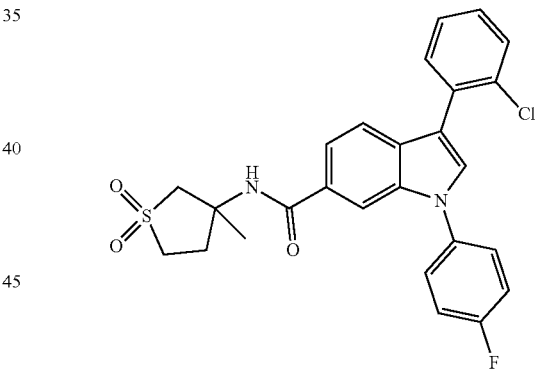

3-(2-chlorophenyl)-1-(4-fluorophenyl)-N-(3-methyl-1,1-dioxidotetrahydrothiophen-3-yl)-1H-indole-6-carboxamide A solution of 3-(2-chlorophenyl)-1-(4-fluorophenyl)-1H-indole-6-carboxylic acid (20 mg, 0.055 mmol), 3-amino-3-methyltetrahydrothiophene-1,1-dioxide (racemic, 12.18 mg, 0.066 mmol), and HATU (31.2 mg, 0.082 mmol) in DMF (1 mL) was stirred at rt for 0.5 h followed by addition of DIEA (47.7 µl, 0.273 mmol). The resulting solution was stirred at RT for 1 h, and then the reaction was quenched with water and purified on RP-HPLC using ACN/water (0.05% TFA) to give the title compound. m/z 496.9 (M+1). $^1$H NMR (500 MHz, CDCl$_3$): δ 7.80 (s, 1H), 7.70-7.67 (m, 2H), 7.57-7.54 (m, 4H), 7.52-7.47 (m, 1H), 7.40-7.37 (m, 1H), 7.35-7.33 (m, 1H), 7.31-7.26 (m, 1H), 6.73 (s, 1H), 3.74-3.71 (d, J=13.9 Hz, 1H), 3.46-3.40 (m, 1H), 3.26-3.24 (m, 1H), 3.16-3.13 (d, J=13.9 Hz, 1H), 3.09-3.05 (m, 1H), 2.29-2.23 (m, 1H), 1.76 (s, 3H).

For Table 1 below, Enantiomer A refers to the faster/earlier eluting enantiomer and Enantiomer B refers to the slower/later eluting enantiomers for the benzyl carbamate precursors of the amine coupling partners (see Int-5-A, Int-5-B, Int-13-A and Int-13-B) that are used for the amide formation reaction and the order of elution does not refer to the final amide products.

(R)- and (S)-3-(2-Chlorophenyl)-N-(1,1-dioxidotetrahydrothiophen-3-yl)-1-(4-fluorophenyl)-1H-indole-6-carboxamide 2,2-A (Fast-Eluting) and 2-B (Slow-Eluting)

Ex 2 (racemic) was synthesized by adapting the synthetic procedure used to synthesize Ex 1. Ex 2 was separated on chiral AD column using 50% MeOH/ACN(2:1)/$CO_2$ to give the two enantiomers, Ex-2-A and Ex-2-B.

3-(2-chlorophenyl)-N-(1,1-dioxidotetrahydrothiophen-3-yl)-1-(4-fluorophenyl)-1H-indole-6-carboxamide 2-A (Enantiomer A, fast-eluting). m/z 482.9 (M+1). $^1$H NMR (500

TABLE 1

| EX. # | Structure | Chemical Name | m/z (M + 1) |
|---|---|---|---|
| 1-A | 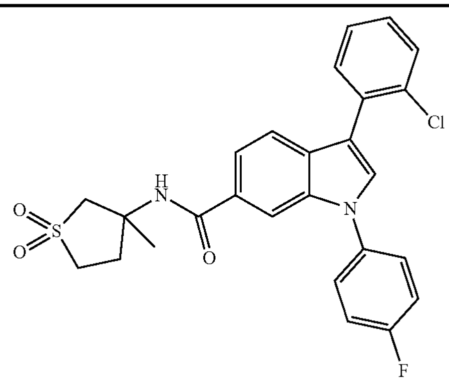 | 3-(2-chlorophenyl)-1-(4-fluorophenyl)-N-(3-methyl-1,1-dioxidotetrahydrothiophen-3-yl)-1H-indole-6-carboxamide (Enantiomer A, fast) | 496.9 |
| 1-B | 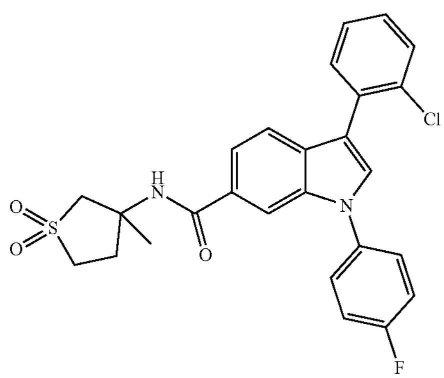 [SMILES: CC1(NC(=O)c2ccc3c(-c4ccccc4Cl)cn(-c4ccc(F)cc4)c3c2)CCS(=O)(=O)C1] | 3-(2-chlorophenyl)-1-(4-fluorophenyl)-N-(3-methyl-1,1-dioxidotetrahydrothiophen-3-yl)-1H-indole-6-carboxamide (Enantiomer B, slow) | 496.9 |

Examples 2, 2-A and 2-B

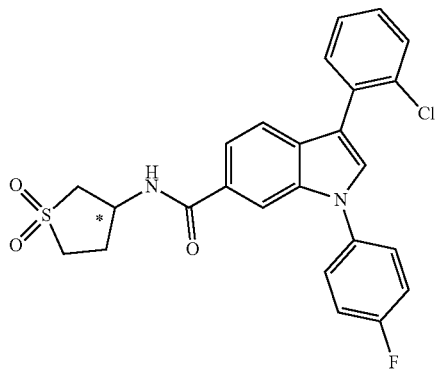 [SMILES: O=C(NC1CCS(=O)(=O)C1)c1ccc2c(-c3ccccc3Cl)cn(-c3ccc(F)cc3)c2c1]

MHz, $d_3$-acetonitrile): δ 8.08 (s, 1H), 7.73-7.72 (d, J=8.4 Hz, 1H), 7.68 (s, 1H), 7.62-7.50 (m, 5H), 7.43-7.39 (m, 1H), 7.37-7.33 (m, 1H), 7.31-7.29 (m, 2H), 6.93-6.91 (d, J=7.6 Hz, 1H), 5.05-5.02 (m, 1H), 3.50-3.47 (m, 1H), 3.34-3.28 (m, 1H), 3.23-3.13 (m, 2H), 2.67-2.61 (m, 1H), 2.49-2.42 (m, 1H).

3-(2-chlorophenyl)-N-(1,1-dioxidotetrahydrothiophen-3-yl)-1-(4-fluorophenyl)-1H-indole-6-carboxamide 2-B (Enantiomer B, slow-eluting). m/z 482.9 (M+1). $^1$H NMR (500 MHz, $d_3$-acetonitrile): δ 8.08 (s, 1H), 7.73-7.72 (d, J=8.4 Hz, 1H), 7.68 (s, 1H), 7.62-7.50 (m, 5H), 7.43-7.39 (m, 1H), 7.37-7.33 (m, 1H), 7.31-7.29 (m, 2H), 6.93-6.91 (d, J=7.6 Hz, 1H), 5.05-5.02 (m, 1H), 3.50-3.47 (m, 1H), 3.34-3.28 (m, 1H), 3.23-3.13 (m, 2H), 2.67-2.61 (m, 1H), 2.49-2.42 (m, 1H).

The examples in Table 2 were synthesized followed by adapting the synthetic procedure for the synthesis of Example 1 by starting with appropriate intermediate selected from Int 1-Int 13 and appropriate amine or aryl halide reaction partner. Enantiomer A or B or Fast or Slow enantiomers in this Table refer to the order of elution of the benzyl carbamate precursors of the amine coupling partners (see Int-5-A, Int-5-B, Int-13-A and Int-13-B) used for the amide formation reaction and do not refer to the final amide product.

TABLE 2

| EX. # | Structure | Chemical Name | m/z (M + 1) |
|---|---|---|---|
| 3 | 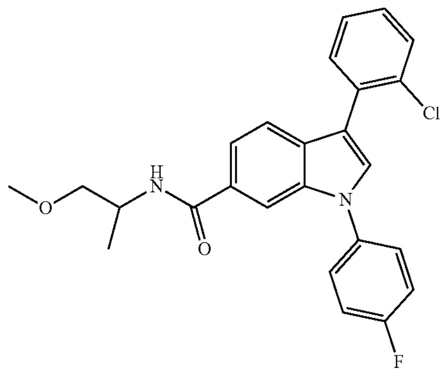 [SMILES: COCC(C)NC(=O)c1ccc2c(-c3ccccc3Cl)cn(-c3ccc(F)cc3)c2c1] | 3-(2-chlorophenyl)-1-(4-fluorophenyl)-N-(1-methoxypropan-2-yl)-1H-indole-6-carboxamide (racemic) | 437.0 |
| 4 | 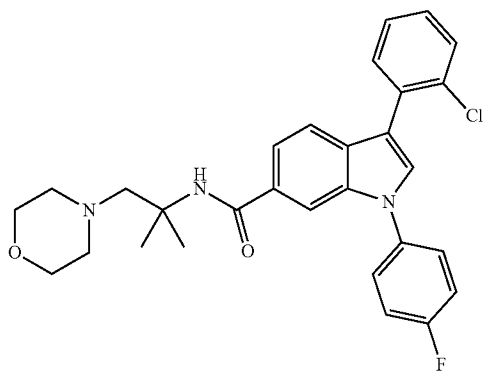 [SMILES: CC(C)(CN1CCOCC1)NC(=O)c1ccc2c(-c3ccccc3Cl)cn(-c3ccc(F)cc3)c2c1] | 3-(2-chlorophenyl)-1-(4-fluorophenyl)-N-(2-methyl-1-morpholinopropan-2-yl)-1H-indole-6-carboxamide | 506.0 |
| 5 | 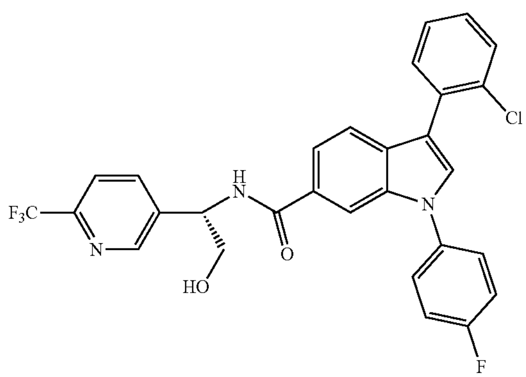 [SMILES: O=C(N[C@H](CO)c1ccc(C(F)(F)F)nc1)c1ccc2c(-c3ccccc3Cl)cn(-c3ccc(F)cc3)c2c1] | (S)-3-(2-chlorophenyl)-1-(4-fluorophenyl)-N-(2-hydroxy-1-(6-(trifluoromethyl)pyridin-3-yl)ethyl)-1H-indole-6-carboxamide | 554.0 |
| 6 | 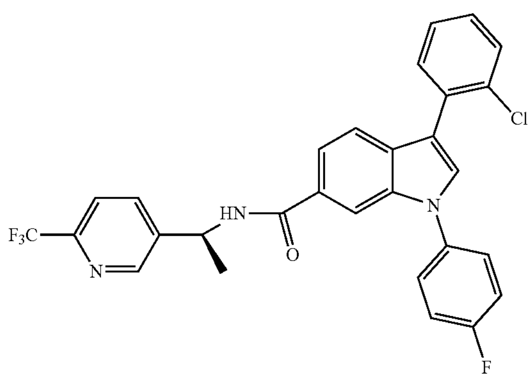 [SMILES: C[C@H](NC(=O)c1ccc2c(-c3ccccc3Cl)cn(-c3ccc(F)cc3)c2c1)c1ccc(C(F)(F)F)nc1] | (S)-3-(2-chlorophenyl)-1-(4-fluorophenyl)-N-(1-(6-(trifluoromethyl)pyridin-3-yl)ethyl)-1H-indole-6-carboxamide | 538.1 |

TABLE 2-continued

| EX. # | Structure | Chemical Name | m/z (M + 1) |
|---|---|---|---|
| 7 | 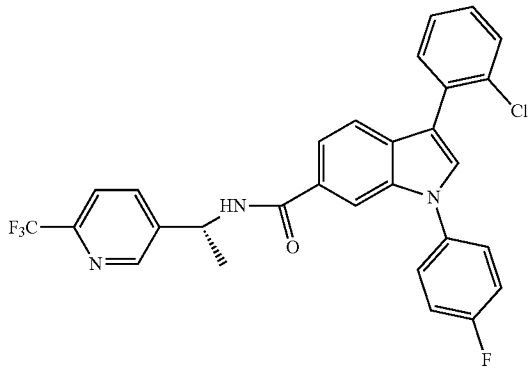 [SMILES: C[C@@H](NC(=O)c1ccc2c(-c3ccccc3Cl)cn(-c3ccc(F)cc3)c2c1)c1ccc(C(F)(F)F)nc1] | (R)-3-(2-chlorophenyl)-1-(4-fluorophenyl)-N-(1-(6-(trifluoromethyl)pyridin-3-yl)ethyl)-1H-indole-6-carboxamide | 538.1 |
| 8-A | 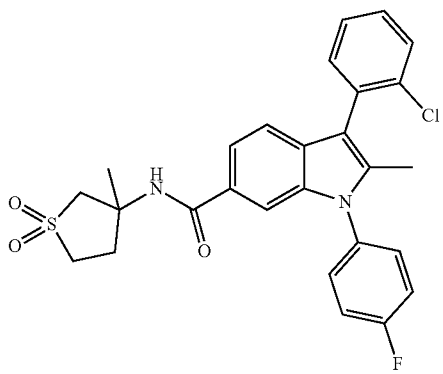 [SMILES: Cc1c(-c2ccccc2Cl)c2ccc(C(=O)NC3(C)CCS(=O)(=O)C3)cc2n1-c1ccc(F)cc1] | 3-(2-chlorophenyl)-1-(4-fluorophenyl)-2-methyl-N-(3-methyl-1,1-dioxidotetrahydrothiophen-3-yl)-1H-indole-6-carboxamide (Enantiomer A) | 511.1 |
| 8-B | 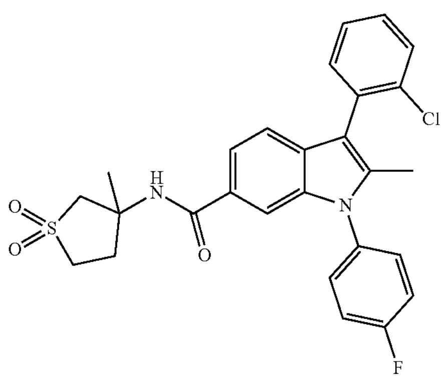 [SMILES: Cc1c(-c2ccccc2Cl)c2ccc(C(=O)NC3(C)CCS(=O)(=O)C3)cc2n1-c1ccc(F)cc1] | 3-(2-chlorophenyl)-1-(4-fluorophenyl)-2-methyl-N-(3-methyl-1,1-dioxidotetrahydrothiophen-3-yl)-1H-indole-6-carboxamide (Enantiomer B) | 511.1 |
| 9-A | 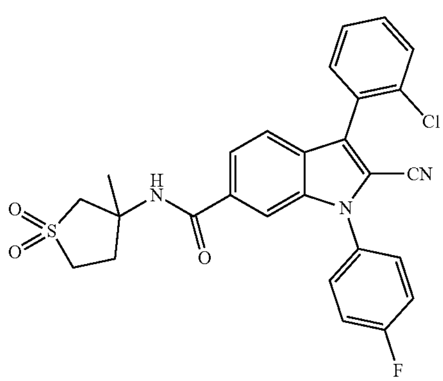 [SMILES: CC1(NC(=O)c2ccc3c(-c4ccccc4Cl)c(C#N)n(-c4ccc(F)cc4)c3c2)CCS(=O)(=O)C1] | 3-(2-chlorophenyl)-2-cyano-1-(4-fluorophenyl)-N-(3-methyl-1,1-dioxidotetrahydrothiophen-3-yl)-1H-indole-6-carboxamide (Enantiomer A) | 522.1 |

TABLE 2-continued

| EX. # | Structure | Chemical Name | m/z (M + 1) |
|---|---|---|---|
| 9-B | 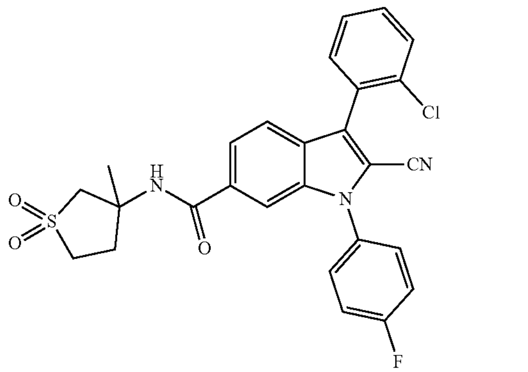 [SMILES: CC1(NC(=O)c2ccc3c(-c4ccccc4Cl)c(C#N)n(-c4ccc(F)cc4)c3c2)CCS(=O)(=O)C1] | 3-(2-chlorophenyl)-2-cyano-1-(4-fluorophenyl)-N-(3-methyl-1,1-dioxidotetrahydrothiophen-3-yl)-1H-indole-6-carboxamide (Enantiomer B) | 522.1 |
| 10-A | 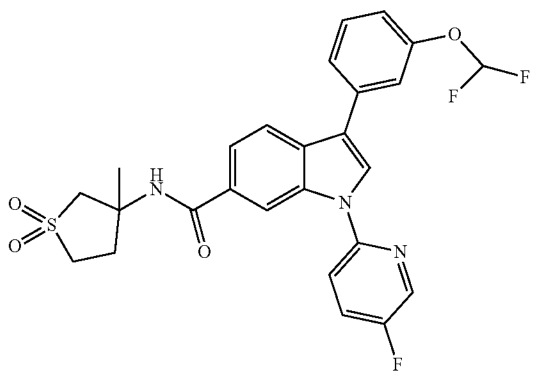 [SMILES: CC1(NC(=O)c2ccc3c(-c4cccc(OC(F)F)c4)cn(-c4ccc(F)cn4)c3c2)CCS(=O)(=O)C1] | 3-(3-(difluoromethoxy)phenyl)-1-(5-fluoropyridin-2-yl)-N-(3-methyl-1,1-dioxidotetrahydrothiophen-3-yl)-1H-indole-6-carboxamide (enantiomer A) | 530.1 |
| 10-B | 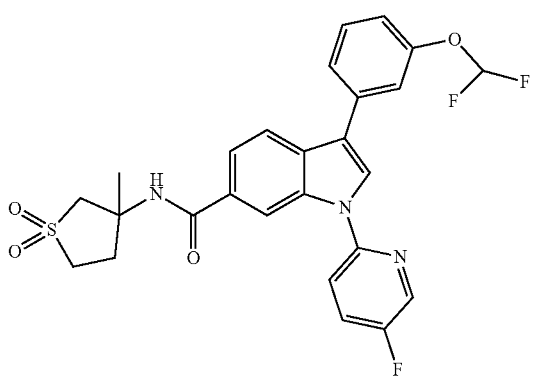 [SMILES: CC1(NC(=O)c2ccc3c(-c4cccc(OC(F)F)c4)cn(-c4ccc(F)cn4)c3c2)CCS(=O)(=O)C1] | 3-(3-(difluoromethoxy)phenyl)-1-(5-fluoropyridin-2-yl)-N-(3-methyl-1,1-dioxidotetrahydrothiophen-3-yl)-1H-indole-6-carboxamide (enantiomer B) | 530.1 |
| 11-A | 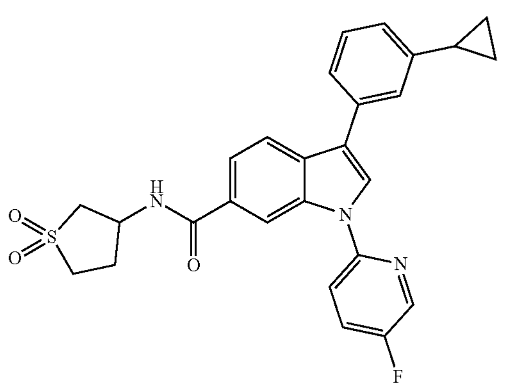 [SMILES: O=C(NC1CCS(=O)(=O)C1)c1ccc2c(-c3cccc(C4CC4)c3)cn(-c3ccc(F)cn3)c2c1] | 3-(3-cyclopropylphenyl)-N-(1,1-dioxidotetrahydrothiophen-3-yl)-1-(5-fluoropyridin-2-yl)-1H-indole-6-carboxamide (enantiomer A) | 490.2 |

TABLE 2-continued

| EX. # | Structure | Chemical Name | m/z (M + 1) |
|---|---|---|---|
| 12-A | 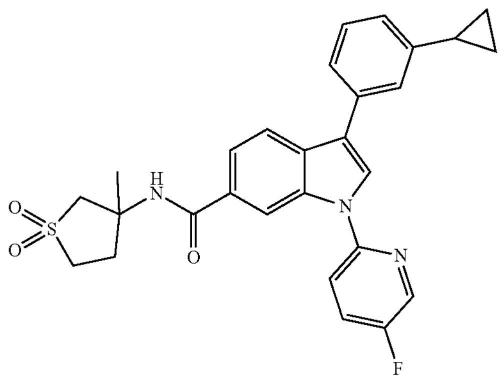 [SMILES: CC1(NC(=O)c2ccc3c(-c4cccc(C5CC5)c4)cn(-c4ccc(F)cn4)c3c2)CCS(=O)(=O)C1] | 3-(3-cyclopropylphenyl)-1-(5-fluoropyridin-2-yl)-N-(3-methyl-1,1-dioxidotetrahydrothiophen-3-yl)-1H-indole-6-carboxamide (enantiomer A) | 504.2 |
| 12-B | 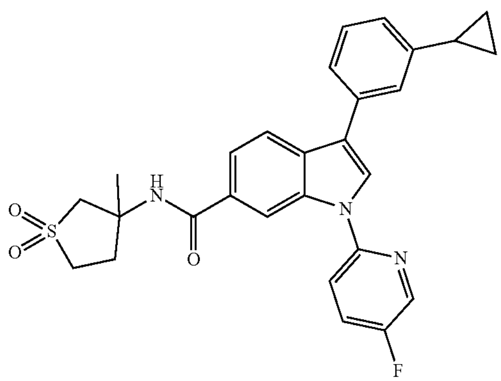 [SMILES: CC1(NC(=O)c2ccc3c(-c4cccc(C5CC5)c4)cn(-c4ccc(F)cn4)c3c2)CCS(=O)(=O)C1] | 3-(3-cyclopropylphenyl)-1-(5-fluoropyridin-2-yl)-N-(3-methyl-1,1-dioxidotetrahydrothiophen-3-yl)-1H-indole-6-carboxamide (enantiomer B) | 504.2 |
| 13-A | 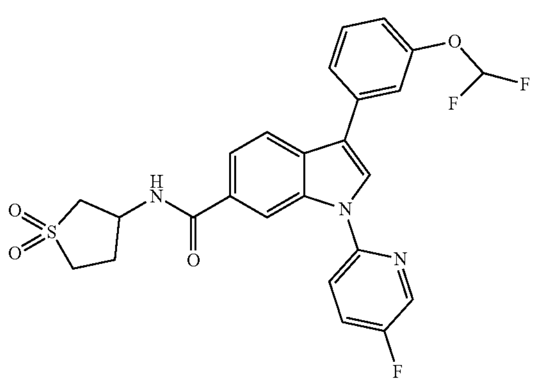 [SMILES: O=C(NC1CCS(=O)(=O)C1)c1ccc2c(-c3cccc(OC(F)F)c3)cn(-c3ccc(F)cn3)c2c1] | 3-(3-(difluoromethoxy)phenyl)-N-(1,1-dioxidotetrahydrothiophen-3-yl)-1-(5-fluoropyridin-2-yl)-1H-indole-6-carboxamide (enantiomer A) | 516.1 |
| 14-A | 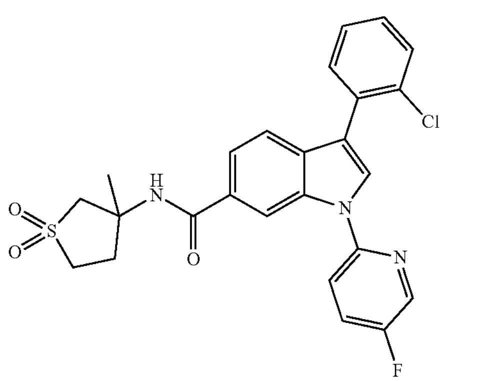 [SMILES: CC1(NC(=O)c2ccc3c(-c4ccccc4Cl)cn(-c4ccc(F)cn4)c3c2)CCS(=O)(=O)C1] | 3-(2-chlorophenyl)-1-(5-fluoropyridin-2-yl)-N-(3-methyl-1,1-dioxidotetrahydrothiophen-3-yl)-1H-indole-6-carboxamide (Enantiomer A, Fast) | 497.9 |

TABLE 2-continued

| EX. # | Structure | Chemical Name | m/z (M + 1) |
|---|---|---|---|
| 14-B | 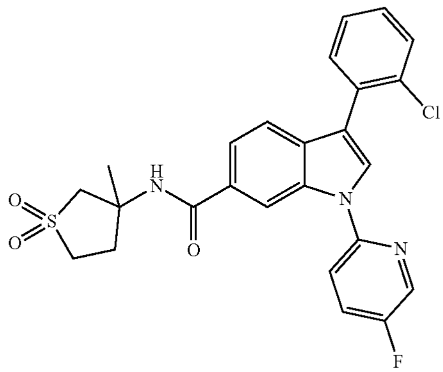 | 3-(2-chlorophenyl)-1-(5-fluoropyridin-2-yl)-N-(3-methyl-1,1-dioxidotetrahydrothiophen-3-yl)-1H-indole-6-carboxamide (Enantiomer B, Slow) | 497.9 |
| 15-A | 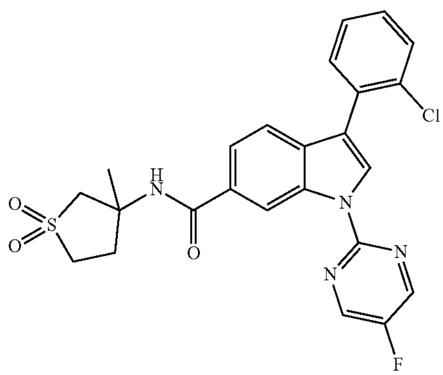 [SMILES: CC1(NC(=O)c2ccc3c(-c4ccccc4Cl)cn(-c4ncc(F)cn4)c3c2)CCS(=O)(=O)C1] | 3-(2-chlorophenyl)-1-(5-fluoropyrimidin-2-yl)-N-(3-methyl-1,1-dioxidotetrahydrothiophen-3-yl)-1H-indole-6-carboxamide (enantiomer A, fast) | 499.0 |
| 15-B | 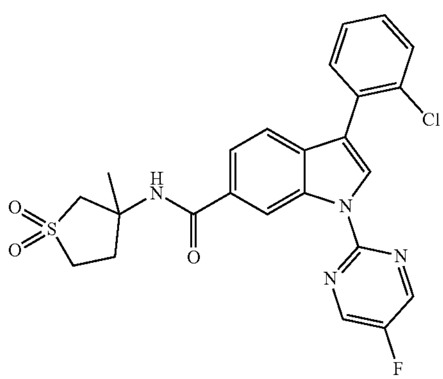 [SMILES: CC1(NC(=O)c2ccc3c(-c4ccccc4Cl)cn(-c4ncc(F)cn4)c3c2)CCS(=O)(=O)C1] | 3-(2-chlorophenyl)-1-(5-fluoropyrimidin-2-yl)-N-(3-methyl-1,1-dioxidotetrahydrothiophen-3-yl)-1H-indole-6-carboxamide (enantiomer B, slow) | 499.0 |
| 16-A | 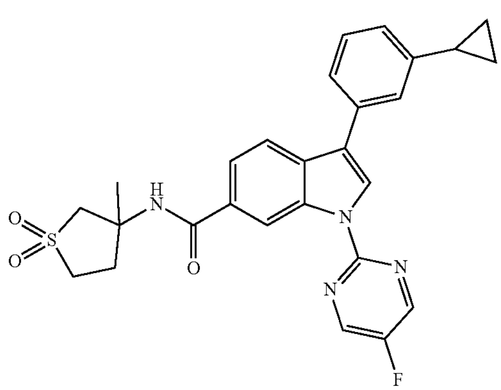 | 3-(3-cyclopropylphenyl)-1-(5-fluoropyrimidin-2-yl)-N-(3-methyl-1,1-dioxidotetrahydrothiophen-3-yl)-1H-indole-6-carboxamide (enantiomer A) | 505.2 |

TABLE 2-continued

| EX. # | Structure | Chemical Name | m/z (M + 1) |
|---|---|---|---|
| 17-A | 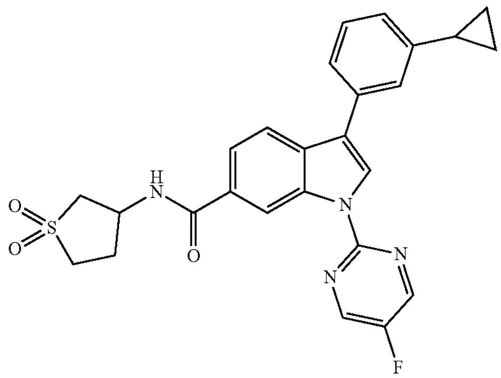 [SMILES: O=C(NC1CCS(=O)(=O)C1)c1ccc2c(-c3cccc(C4CC4)c3)cn(-c3ncc(F)cn3)c2c1] | 3-(3-cyclopropylphenyl)-N-(1,1-dioxidotetrahydrothiophen-3-yl)-1-(5-fluoropyrimidin-2-yl)-1H-indole-6-carboxamide (enantiomer A) | 491.1 |
| 18-A | 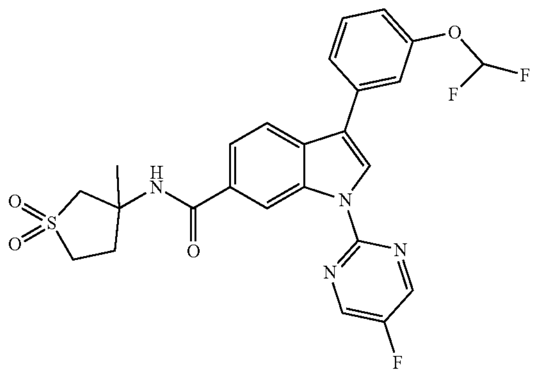 [SMILES: CC1(NC(=O)c2ccc3c(-c4cccc(OC(F)F)c4)cn(-c4ncc(F)cn4)c3c2)CCS(=O)(=O)C1] | 3-(3-(difluoromethoxy)phenyl)-1-(5-fluoropyrimidin-2-yl)-N-(3-methyl-1,1-dioxidotetrahydrothiophen-3-yl)-1H-indole-6-carboxamide (enantiomer A) | 531.0 |
| 18-B | 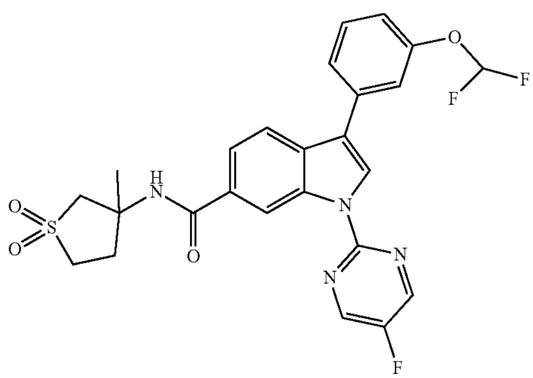 [SMILES: CC1(NC(=O)c2ccc3c(-c4cccc(OC(F)F)c4)cn(-c4ncc(F)cn4)c3c2)CCS(=O)(=O)C1] | 3-(3-(difluoromethoxy)phenyl)-1-(5-fluoropyrimidin-2-yl)-N-(3-methyl-1,1-dioxidotetrahydrothiophen-3-yl)-1H-indole-6-carboxamide (enantiomer B) | 531.0 |
| 19-A | 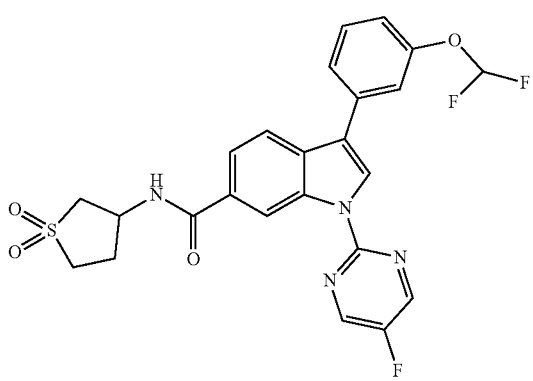 [SMILES: O=C(NC1CCS(=O)(=O)C1)c1ccc2c(-c3cccc(OC(F)F)c3)cn(-c3ncc(F)cn3)c2c1] | 3-(3-(difluoromethoxy)phenyl)-N-(1,1-dioxidotetrahydrothiophen-3-yl)-1-(5-fluoropyrimidin-2-yl)-1H-indole-6-carboxamide (enantiomer A) | 517.0 |

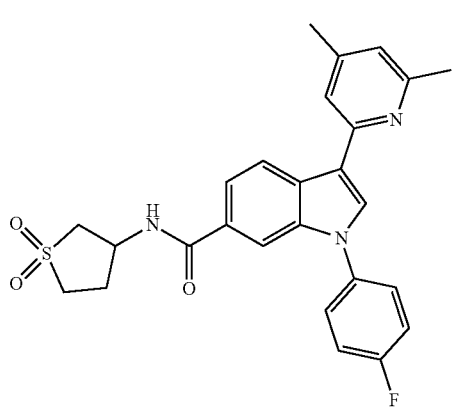 [SMILES: Cc1cc(C)nc(-c2cn(-c3ccc(F)cc3)c3cc(C(=O)NC4CCS(=O)(=O)C4)ccc23)c1]

3-(4,6-dimethylpyridin-2-yl)-N-(1,1-dioxidotetrahydrothiophen-3-yl)-1-(4-fluorophenyl)-1H-indole-6-carboxamide (racemic)

A solution of 2-bromo-4,6-dimethylpyridine (13.59 mg, 0.073 mmol), N-(1,1-dioxidotetrahydrothiophen-3-yl)-1-(4-fluorophenyl)-3-(4,4,5,5-tetramethyl-1,3,2-dioxaborolan-2-yl)-1H-indole-6-carboxamide (racemic, 26 mg, 0.052 mmol), and 1 M aq. $Na_2CO_3$ (157 µl, 0.157 mmol) in dioxane (1 mL) was flushed with $N_2$ before addition of and bis(triphenylphosphine)palladium(II)dichloride (3.66 mg, 5.22 µmol). The resulting mixture was heated in a microwave at 150° C. for 30 min. The mixture was then filtered, and the filtrate was concentrated in vacuo and purified on RP-HPLC using ACN/water (0.1% TFA) to afford the title compound. m/z 478.2 (M+1); $^1$H NMR (500 MHz, $d_3$-acetonitrile): δ 8.44 (s, 1H), 8.03-8.02 (d, J=8.5 Hz, 1H), 7.88 (s, 1H), 7.81 (s, 1H), 7.72-7.70 (d, J=8.6 Hz, 1H), 7.60-7.58 (m, 3H), 7.33-7.31 (m, 3H), 4.77-4.73 (m, 1H), 3.50-4.46 (m, 1H), 3.34-3.30 (m, 1H), 3.16-3.07 (m, 2H), 2.71 (s, 3H), 2.57 (s, 3H), 2.56-2.53 (m, 1H), 2.34-2.30 (m, 1H).

The examples in Table 3 were synthesized by adapting the synthetic procedure for the the the synthesis of Ex 20 starting from Int-4 or Int-12 and appropriate aryl bromides.

TABLE 3

| EX. # | Structure | Chemical Name | m/z (M + 1) |
|---|---|---|---|
| 21 | 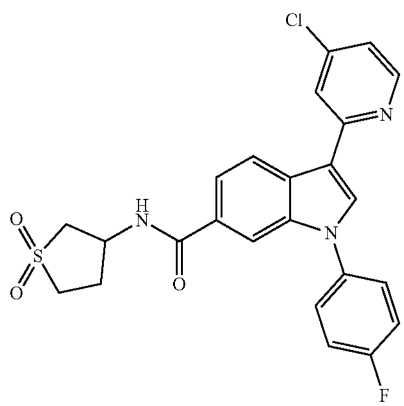 [SMILES: O=C(NC1CCS(=O)(=O)C1)c1ccc2c(-c3cc(Cl)ccn3)cn(-c3ccc(F)cc3)c2c1] | 3-(4-chloropyridin-2-yl)-N-(1,1-dioxidotetrahydrothiophen-3-yl)-1-(4-fluorophenyl)-1H-indole-6-carboxamide (racemic) | 484.1 |
| 22 | 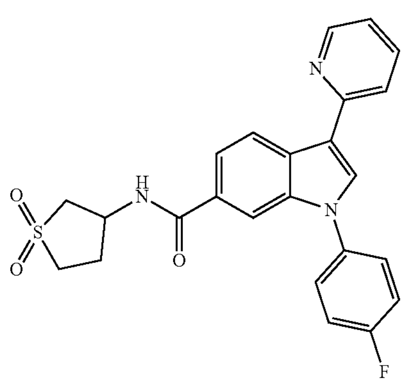 [SMILES: O=C(NC1CCS(=O)(=O)C1)c1ccc2c(-c3ccccn3)cn(-c3ccc(F)cc3)c2c1] | N-(1,1-dioxidotetrahydrothiophen-3-yl)-1-(4-fluorophenyl)-3-(pyridin-2-yl)-1H-indole-6-carboxamide (racemic) | 450.1 |

TABLE 3-continued

| EX. # | Structure | Chemical Name | m/z (M + 1) |
|---|---|---|---|
| 23 | 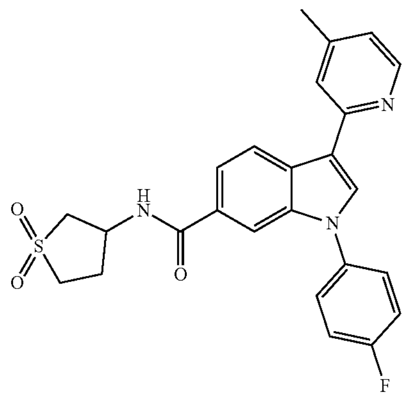 [SMILES: Cc1ccnc(-c2cn(-c3ccc(F)cc3)c3cc(C(=O)NC4CCS(=O)(=O)C4)ccc23)c1] | N-(1,1-dioxidotetrahydrothiophen-3-yl)-1-(4-fluorophenyl)-3-(4-methylpyridin-2-yl)-1H-indole-6-carboxamide (racemic) | 464.2 |
| 24 | 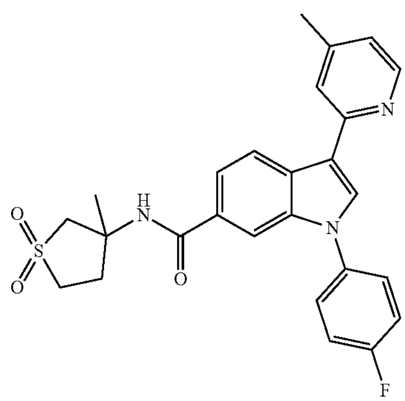 [SMILES: Cc1ccnc(-c2cn(-c3ccc(F)cc3)c3cc(C(=O)NC4(C)CCS(=O)(=O)C4)ccc23)c1] | 1-(4-fluorophenyl)-N-(3-methyl-1,1-dioxidotetrahydrothiophen-3-yl)-3-(4-methylpyridin-2-yl)-1H-indole-6-carboxamide (racemic) | 478.2 |
| 25 | 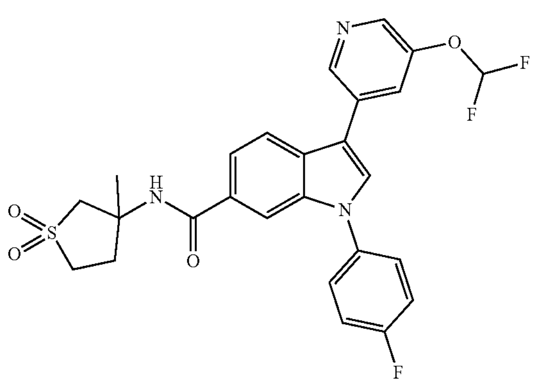 [SMILES: CC1(NC(=O)c2ccc3c(-c4cncc(OC(F)F)c4)cn(-c4ccc(F)cc4)c3c2)CCS(=O)(=O)C1] | 3-(5-(difluoromethoxy)pyridin-3-yl)-1-(4-fluorophenyl)-N-(3-methyl-1,1-dioxidotetrahydrothiophen-3-yl)-1H-indole-6-carboxamide (racemic) | 530.1 |

Example 26-A

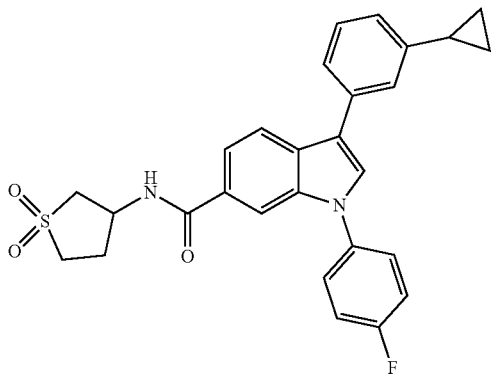 [SMILES: O=C(NC1CCS(=O)(=O)C1)c1ccc2c(-c3cccc(C4CC4)c3)cn(-c3ccc(F)cc3)c2c1]

3-(3-Cyclopropylphenyl)-N-(1,1-dioxidotetrahydro-thiophen-3-yl)-1-(4-fluorophenyl)-1H-indole-6-carboxamide (Enantiomer A)

Step A: 3-Bromo-N-(1,1-dioxidotetrahydrothiophen-3-yl)-1-(4-fluorophenyl)-1H-indole-6-carboxamide (enantiomer A)

A solution of HATU (683 mg, 1.796 mmol), 3-bromo-1-(4-fluorophenyl)-1H-indole-6-carboxylic acid (400 mg, 1.197 mmol), and 3-aminotetrahydrothiophene-1,1-dioxide (Enantiomer A, 247 mg, 1.437 mmol) in DMF (2 mL) was stirred at rt for 1 h before addition of DIEA (836 μl, 4.79 mmol). The resulting solution was stirred at rt for 2 h, and then purified on RP-HPLC ACN/water (0.05% TFA) to afford the title compound. m/z 451.0/453.0 (M+1).

Step B: 3-(3-Cyclopropylphenyl)-N-(1,1-dioxidotetrahydrothiophen-3-yl)-1-(4-fluorophenyl)-1H-indole-6-carboxamide (Enantiomer A)

3-Bromo-N-(1,1-dioxidotetrahydrothiophen-3-yl)-1-(4-fluorophenyl)-1H-indole-6-carboxamide (enantiomer A) (50 mg, 0.111 mmol), 2-(3-cyclopropylphenyl)-4,4,5,5-tetramethyl-1,3,2-dioxaborolane (32.5 mg, 0.133 mmol), Pd(PPh$_3$)$_4$(12.80 mg, 0.011 mmol), and 1 M aq. Na$_2$CO$_3$ (443 μl, 0.443 mmol) in dioxane (3 mL) was heated at 100° C. overnight. After filtration, the filtrate was concentrated and the residue was purified on RP-HPLC using ACN/water (0.1% TFA) to give the title compound. m/z 489.2 (M+1). $^1$H NMR (500 MHz, d$_6$-DMSO): δ 8.74-8.73 (m, 1H), 8.12 (s, 1H), 8.02 (s, 1H), 7.98-7.96 (m, 1H), 7.76-7.73 (m, 3H), 7.53-7.47 (m, 2H), 7.41 (s, 1H), 7.36-7.33 (m, 1H), 7.03-7.02 (m, 1H), 4.71-4.69 (m, 1H), 3.52-3.48 (m, 1H), 3.36-3.33 (m, 1H), 3.21-3.17 (m, 1H), 3.09-3.05 (m, 1H), 2.44-2.43 (m, 1H), 2.23-1.97 (m, 1H), 2.21-1.97 (m, 1H), 0.99-0.96 (m, 2H), 0.78-0.75 (m, 2H).

Example 27-A

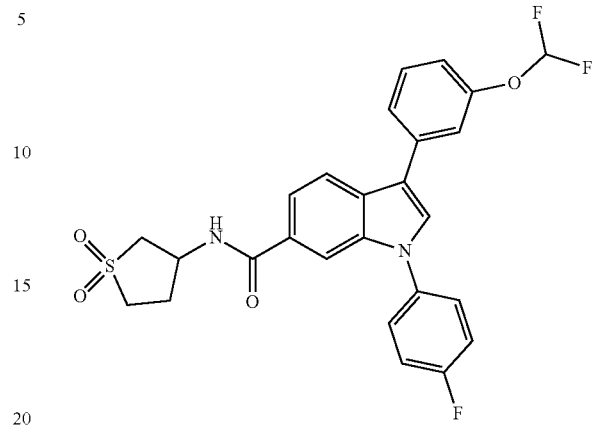

3-(3-(difluoromethoxy)phenyl)-N-(1,1-dioxidotetrahydrothiophen-3-yl)-1-(4-fluorophenyl)-1H-indole-6-carboxamide (enantiomer A)

3-(3-(difluoromethoxy)phenyl)-N-(1,1-dioxidotetrahydrothiophen-3-yl)-1-(4-fluorophenyl)-1H-indole-6-carboxamide (enantiomer A) was synthesized by adapting the synthetic procedure for the synthesis of Ex 26-A using 2-(3-(difluoromethoxy)phenyl)-4,4,5,5-tetramethyl-1,3,2-dioxaborolane as the coupling substrate. m/z 515.1 (M+1).

Example 28

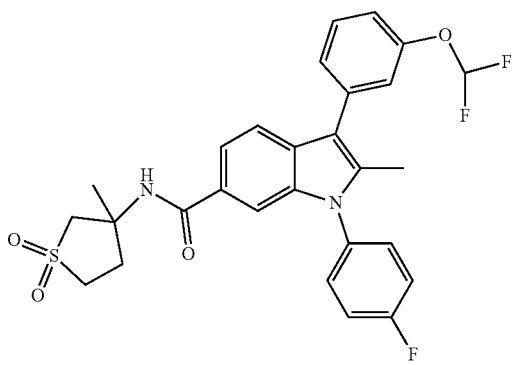 [SMILES: Cc1c(-c2cccc(OC(F)F)c2)c2ccc(C(=O)NC3(C)CCS(=O)(=O)C3)cc2n1-c1ccc(F)cc1]

3-(3-(difluoromethoxy)phenyl)-1-(4-fluorophenyl)-2-methyl-N-(3-methyl-1,1-dioxidotetrahydrothiophen-3-yl)-1H-indole-6-carboxamide (racemic)

Step A: 3-(3-(difluoromethoxy)phenyl)-1-(4-fluorophenyl)-N-(3-methyl-1,1-dioxidotetrahydrothiophen-3-yl)-1H-indole-6-carboxamide (racemic)

A solution of 2-(3-(difluoromethoxy)phenyl)-4,4,5,5-tetramethyl-1,3,2-dioxaborolane (348 mg, 1.289 mmol), 3-bromo-1-(4-fluorophenyl)-N-(3-methyl-1,1-dioxidotetrahydrothiophen-3-yl)-1H-indole-6-carboxamide (racemic, 500 mg, 1.074 mmol), Pd(PPh$_3$)$_4$(124 mg, 0.107 mmol), 1 M aq. Na$_2$CO$_3$ (3223 μl, 3.22 mmol) in dioxane (30 mL) was bubbled with $N_2$ for 20 min and then heated at 100° C. overnight. After filtration, the filtrate was concentrated in vacuo and the residue was purified by silica gel chromatography (EtOAc/hexanes) to afford the title compound. m/z 529.1 (M+1).

Step B: 2-Bromo-3-(3-(difluoromethoxy)phenyl)-1-(4-fluorophenyl)-N-(3-methyl-1,1-dioxidotetrahydrothiophen-3-yl)-1H-indole-6-carboxamide (racemic)

To a solution of 3-(3-(difluoromethoxy)phenyl)-1-(4-fluorophenyl)-N-(3-methyl-1,1-dioxidotetrahydrothiophen-3-yl)-1H-indole-6-carboxamide (racemic, 250 mg, 0.473 mmol) in AcOH (5 mL) was added bromine (25.6 µl, 0.497 mmol) in AcOH (20 mL). The resulting solution was stirred at rt for 1 h and then heated at 80° C. for 2 h. The reaction mixture was concentrated in vacuo, and the residue was treated with EtOAc. The mixture was filtered and the solids were collected, and the filtrate was washed with sat. $Na_2SO_3$ and $NaHCO_3$. The solution was dried over $Na_2SO_4$, concentrated in vacuo, and combined with the previous obtained solid to give the title compound. m/z 607.0/609.0 (M+1).

Step C: 3-(3-(Difluoromethoxy)phenyl)-1-(4-fluorophenyl)-2-methyl-N-(3-methyl-1,1-dioxidotetrahydrothiophen-3-yl)-1H-indole-6-carboxamide (racemic)

A solution of 2-bromo-3-(3-(difluoromethoxy)phenyl)-1-(4-fluorophenyl)-N-(3-methyl-1,1-dioxidotetrahydrothiophen-3-yl)-1H-indole-6-carboxamide (racemic, 22 mg, 0.036 mmol), methylboronic acid (4.34 mg, 0.072 mmol), and 1 M aq. $Na_2CO_3$ (109 µLµL, 0.109 mmol) in dioxane (2 mL) was flushed with $N_2$ before addition of bis(triphenylphosphine)palladium (II) dichloride (2.54 mg, 3.62 µmol), the resulting solution was microwaved at 150° C. for 60 min. After filtration, the filtrate was concentrated, and the residue was purified on RP-HPLC using ACN/water (0.1% TFA) to give the title compound. m/z 543.2 (M+1). $^1$H NMR (500 MHz, $d_6$-DMSO): δ 7.69-7.67 (d, J=8.4 Hz, 1H), 7.59-7.53 (m, 2H), 7.51-7.45 (m, 3H), 7.40-7.36 (t, J=8.3 Hz, 2H), 7.34 (s, 1H), 7.16-7.14 (m, 1H), 7.01 (s, 1H), 7.02-6.73 (t, J=74.4 Hz, 1H), 3.93-3.90 (d, J=13.8 Hz, 1H), 3.36-3.29 (m, 1H), 3.21-3.16 (m, 1H), 3.12-3.09 (d, J=13.7 Hz, 1H), 2.77-2.72 (m, 1H), 2.32 (s, 3H), 2.27-2.20 (m, 1H), 1.61 (s, 3H).

Example 29

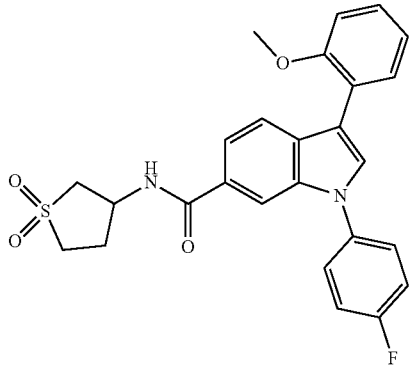 [SMILES: COc1ccccc1-c1cn(-c2ccc(F)cc2)c2cc(C(=O)NC3CCS(=O)(=O)C3)ccc12]

N-(1,1-dioxidotetrahydrothiophen-3-yl)-1-(4-fluorophenyl)-3-(2-methoxyphenyl)-1H-indole-6-carboxamide (racemic)

A mixture of (2-methoxyphenyl)boronic acid (15 mg, 0.09 mmol), 3-bromo-N-(1,1-dioxidotetrahydrothiophen-3-yl)-1-(4-fluorophenyl)-1H-indole-6-carboxamide (racemic) (30 mg, 0.067 mmol), bis(triphenylphosphine)palladium (II) dichloride (16 mg, 0.02 mmol), and $K_2CO_3$ (92 mg, 0.67 mmol) in toluene (0.5 ml) and EtOH (0.5 ml) was heated in microwave at 100° C. for 10 min. After filtration, the filtrate was concentrated and the residue dissolved in 1 mL DMSO and purified using RP-HPLC to give the title compound. LC/MS: 479 (M+1).

The examples in Table 4 below were prepared by adapting the synthetic procedures used for the synthesis of Ex 26-A, 27-A, 28, and 29 using the same racemic indole boronate.

TABLE 4

| Ex. # | Structure | Chemical Name | m/z (M + 1) |
|---|---|---|---|
| 30 | 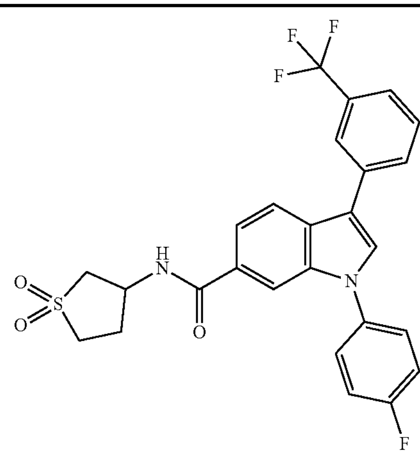 | N-(1,1-dioxidotetrahydrothiophen-3-yl)-1-(4-fluorophenyl)-3-[3-(trifluoromethyl)phenyl]-1H-indole-6-carboxamide (racemic) | 517 |

TABLE 4-continued

| Ex. # | Structure | Chemical Name | m/z (M + 1) |
|---|---|---|---|
| 31 | 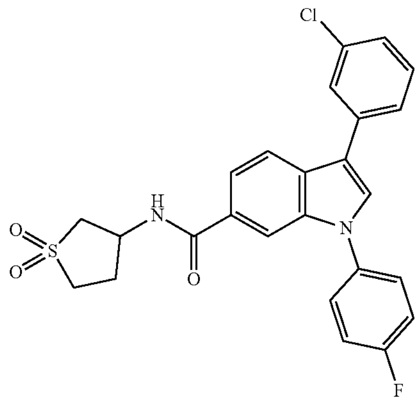 [SMILES: O=C(NC1CCS(=O)(=O)C1)c1ccc2c(-c3cccc(Cl)c3)cn(-c3ccc(F)cc3)c2c1] | 3-(3-chlorophenyl)-N-(1,1-dioxidotetrahydrothiophen-3-yl)-1-(4-fluorophenyl)-1H-indole-6-carboxamide (racemic) | 483 |
| 32 | 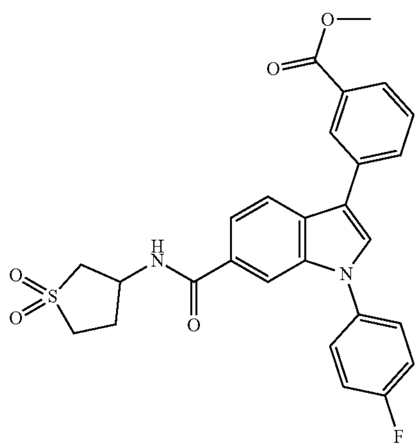 [SMILES: COC(=O)c1cccc(-c2cn(-c3ccc(F)cc3)c3cc(C(=O)NC4CCS(=O)(=O)C4)ccc23)c1] | methyl 3-{6-[(1,1-dioxidotetrahydrothiophen-3-yl)carbamoyl]-1-(4-fluorophenyl)-1H-indol-3-yl}benzoate (racemic) | 507 |
| 33 | 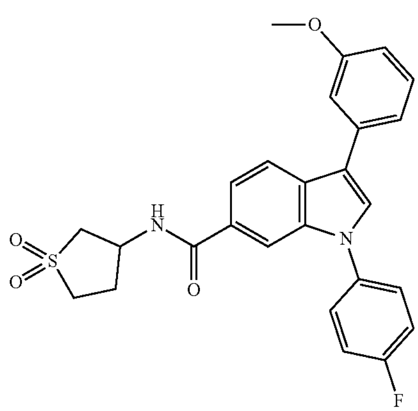 [SMILES: COc1cccc(-c2cn(-c3ccc(F)cc3)c3cc(C(=O)NC4CCS(=O)(=O)C4)ccc23)c1] | N-(1,1-dioxidotetrahydrothiophen-3-yl)-1-(4-fluorophenyl)-3-(3-methoxyphenyl)-1H-indole-6-carboxamide (racemic) | 479 |

TABLE 4-continued

| Ex. # | Structure | Chemical Name | m/z (M + 1) |
|---|---|---|---|
| 34 | 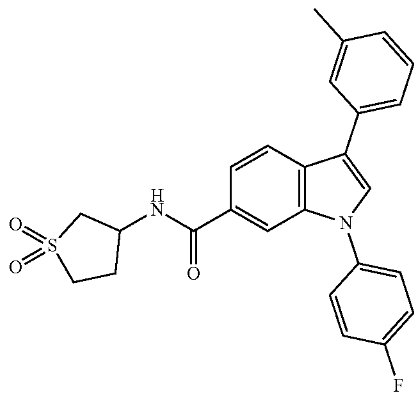 [SMILES: Cc1cccc(-c2cn(-c3ccc(F)cc3)c3cc(C(=O)NC4CCS(=O)(=O)C4)ccc23)c1] | N-(1,1-dioxidotetrahydrothiophen-3-yl)-1-(4-fluorophenyl)-3-(3-methylphenyl)-1H-indole-6-carboxamide (racemic) | 463 |
| 35 | 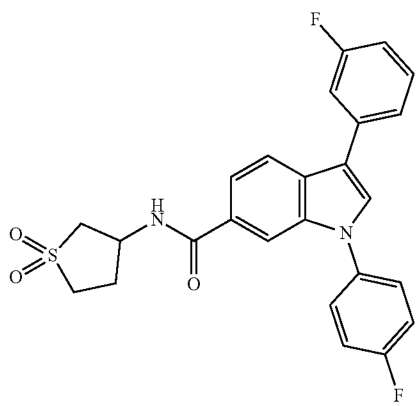 [SMILES: O=C(NC1CCS(=O)(=O)C1)c1ccc2c(-c3cccc(F)c3)cn(-c3ccc(F)cc3)c2c1] | N-(1,1-dioxidotetrahydrothiophen-3-yl)-3-(3-fluorophenyl)-1-(4-fluorophenyl)-1H-indole-6-carboxamide (racemic) | 467 |
| 36 | 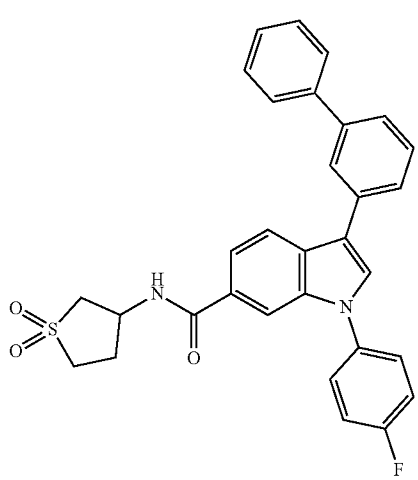 [SMILES: O=C(NC1CCS(=O)(=O)C1)c1ccc2c(-c3cccc(-c4ccccc4)c3)cn(-c3ccc(F)cc3)c2c1] | 3-biphenyl-3-yl-N-(1,1-dioxidotetrahydrothiophen-3-yl)-1-(4-fluorophenyl)-1H-indole-6-carboxamide (racemic) | 525 |

TABLE 4-continued

| Ex. # | Structure | Chemical Name | m/z (M + 1) |
|---|---|---|---|
| 37 | 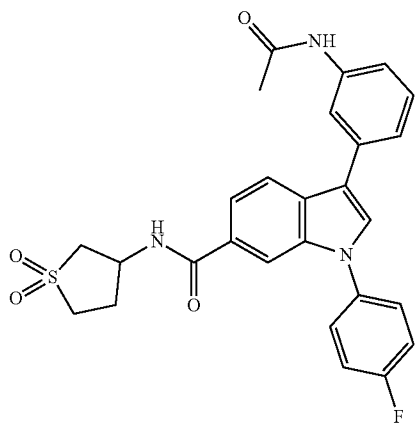 [SMILES: CC(=O)Nc1cccc(-c2cn(-c3ccc(F)cc3)c3cc(C(=O)NC4CCS(=O)(=O)C4)ccc23)c1] | 3-[3-(acetylamino)phenyl]-N-(1,1-dioxidotetrahydrothiophen-3-yl)-1-(4-fluorophenyl)-1H-indole-6-carboxamide (racemic) | 506 |
| 38 | 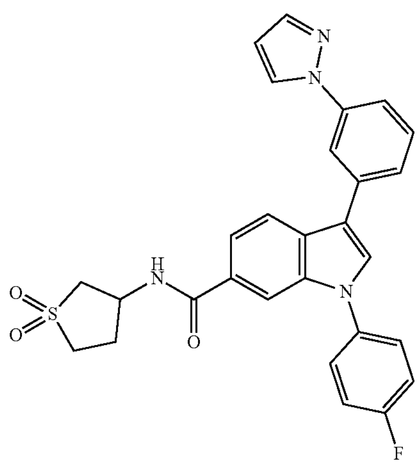 [SMILES: O=C(NC1CCS(=O)(=O)C1)c1ccc2c(-c3cccc(-n4cccn4)c3)cn(-c3ccc(F)cc3)c2c1] | N-(1,1-dioxidotetrahydrothiophen-3-yl)-1-(4-fluorophenyl)-3-[3-(1H-pyrazol-1-yl)phenyl]-1H-indole-6-carboxamide (racemic) | 515 |
| 39 | 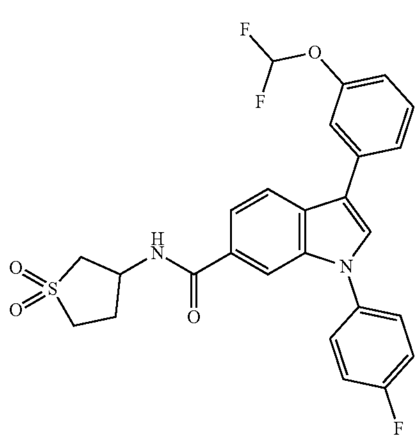 [SMILES: O=C(NC1CCS(=O)(=O)C1)c1ccc2c(-c3cccc(OC(F)F)c3)cn(-c3ccc(F)cc3)c2c1] | 3-[3-(difluoromethoxy)phenyl]-N-(1,1-dioxidotetrahydrothiophen-3-yl)-1-(4-fluorophenyl)-1H-indole-6-carboxamide (racemic) | 515 |

TABLE 4-continued

| Ex. # | Structure | Chemical Name | m/z (M + 1) |
|---|---|---|---|
| 40 | 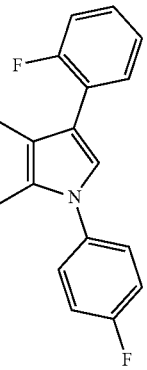 | N-(1,1-dioxidotetrahydrothiophen-3-yl)-3-(2-fluorophenyl)-1-(4-fluorophenyl)-1H-indole-6-carboxamide (racemic) | 467 |
| 41 | 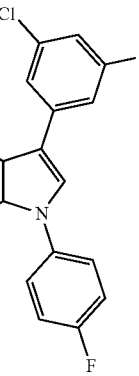 | 3-(3,5-dichlorophenyl)-N-(1,1-dioxidotetrahydrothiophen-3-yl)-1-(4-fluorophenyl)-1H-indole-6-carboxamide (racemic) | 517 |
| 42 | 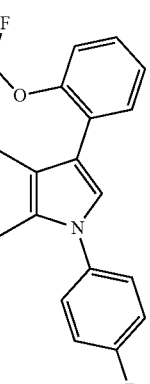 | 3-[2-(difluoromethoxy)phenyl]-N-(1,1-dioxidotetrahydrothiophen-3-yl)-1-(4-fluoropheny)-1H-indole-6-carboxamide (racemic) | 515 |
| 43 | 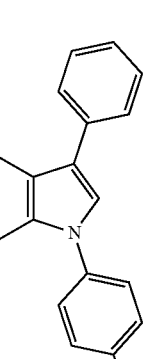 | N-(1,1-dioxidotetrahydrothiophen-3-yl)-1-(4-fluorophenyl)-3-phenyl-1H-indole-6-carboxamide (racemic) | 449 |

TABLE 4-continued

| Ex. # | Structure | Chemical Name | m/z (M + 1) |
|---|---|---|---|
| 44 | 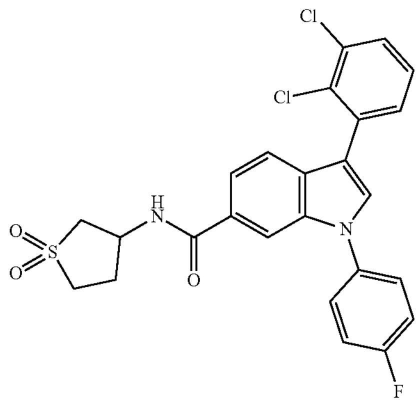 [SMILES: O=C(NC1CCS(=O)(=O)C1)c1ccc2c(-c3cccc(Cl)c3Cl)cn(-c3ccc(F)cc3)c2c1] | 3-(2,3-dichlorophenyl)-N-(1,1-dioxidotetrahydrothiophen-3-yl)-1-(4-fluorophenyl)-1H-indole-6-carboxamide (racemic) | 517 |
| 45 | 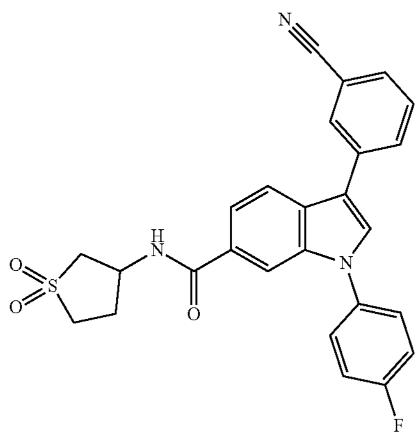 [SMILES: N#Cc1cccc(-c2cn(-c3ccc(F)cc3)c3cc(C(=O)NC4CCS(=O)(=O)C4)ccc23)c1] | 3-(3-cyanophenyl)-N-(1,1-dioxidotetrahydrothiophen-3-yl)-1-(4-fluorophenyl)-1H-indole-6-carboxamide (racemic) | 474 |
| 46 | 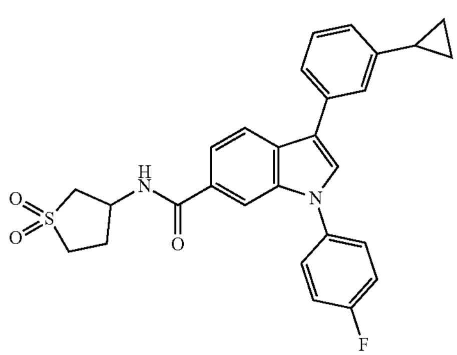 [SMILES: O=C(NC1CCS(=O)(=O)C1)c1ccc2c(-c3cccc(C4CC4)c3)cn(-c3ccc(F)cc3)c2c1] | 3-(3-cyclopropylphenyl)-N-(1,1-dioxidotetrahydrothiophen-3-yl)-1-(4-fluorophenyl)-1H-indole-6-carboxamide (racemic) | 489 |
| 47 | 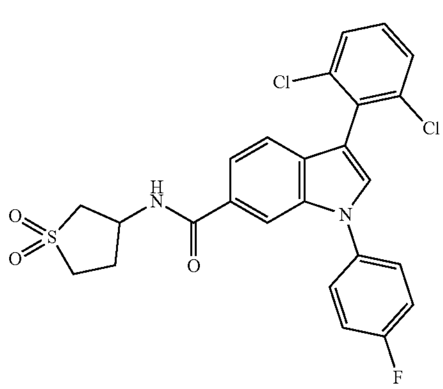 [SMILES: O=C(NC1CCS(=O)(=O)C1)c1ccc2c(-c3c(Cl)cccc3Cl)cn(-c3ccc(F)cc3)c2c1] | 3-(2,6-dichlorophenyl)-N-(1,1-dioxidotetrahydrothiophen-3-yl)-1-(4-fluorophenyl)-1H-indole-6-carboxamide (racemic) | 517 |

TABLE 4-continued

| Ex. # | Structure | Chemical Name | m/z (M + 1) |
|---|---|---|---|
| 48 | 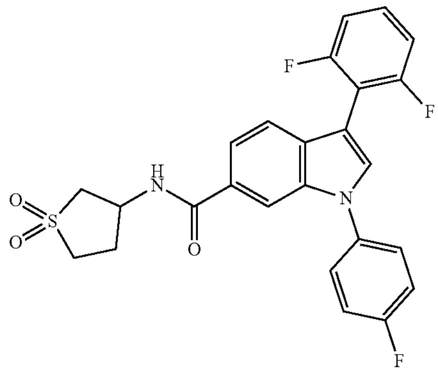 [SMILES: O=C(NC1CCS(=O)(=O)C1)c1ccc2c(-c3c(F)cccc3F)cn(-c3ccc(F)cc3)c2c1] | 3-(2,6-difluorophenyl)-N-(1,1-dioxidotetrahydrothiophen-3-yl)-1-(4-fluorophenyl)-1H-indole-6-carboxamide (racemic) | 485 |
| 49 | 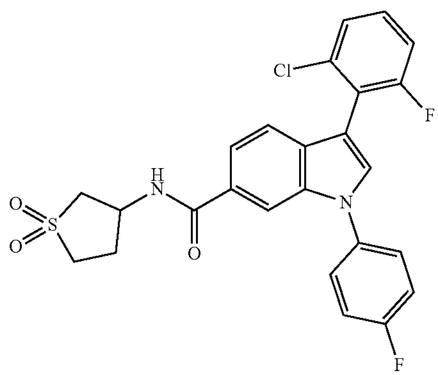 [SMILES: O=C(NC1CCS(=O)(=O)C1)c1ccc2c(-c3c(F)cccc3Cl)cn(-c3ccc(F)cc3)c2c1] | 3-(2-chloro-6-fluorophenyl)-N-(1,1-dioxidotetrahydrothiophen-3-yl)-1-(4-fluorophenyl)-1H-indole-6-carboxamide (racemic) | 501 |
| 50 | 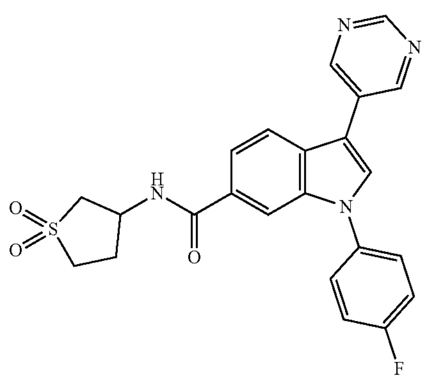 [SMILES: O=C(NC1CCS(=O)(=O)C1)c1ccc2c(-c3cncnc3)cn(-c3ccc(F)cc3)c2c1] | N-(1,1-dioxidotetrahydrothiophen-3-yl)-1-(4-fluorophenyl)-3-pyrimidin-5-yl-1H-indole-6-carboxamide (racemic) | 451 |
| 51 | 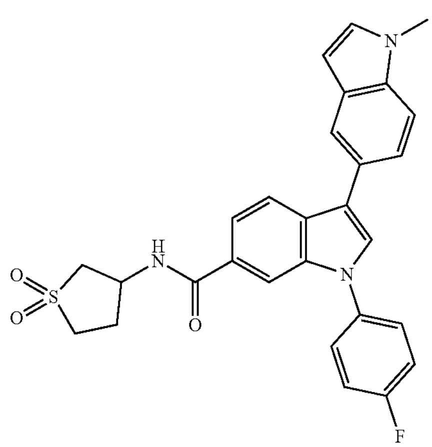 [SMILES: Cn1ccc2cc(-c3cn(-c4ccc(F)cc4)c4cc(C(=O)NC5CCS(=O)(=O)C5)ccc34)ccc21] | N-(1,1-dioxidotetrahydrothiophen-3-yl)-1-(4-fluorophenyl)-1'-methyl-1H,1'H-3,5'-biindole-6-carboxamide (racemic) | 502 |

TABLE 4-continued

| Ex. # | Structure | Chemical Name | m/z (M + 1) |
|---|---|---|---|
| 52 | 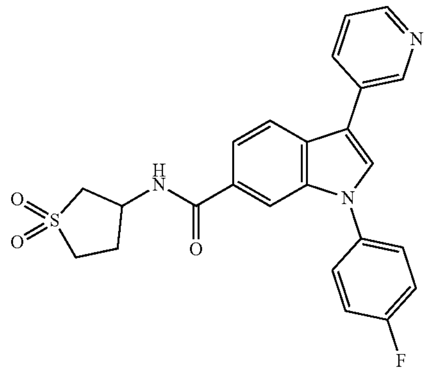 [SMILES: O=C(NC1CCS(=O)(=O)C1)c1ccc2c(-c3cccnc3)cn(-c3ccc(F)cc3)c2c1] | N-(1,1-dioxidotetrahydrothiophen-3-yl)-1-(4-fluorophenyl)-3-pyridin-3-yl-1H-indole-6-carboxamide (racemic) | 450 |
| 53 | 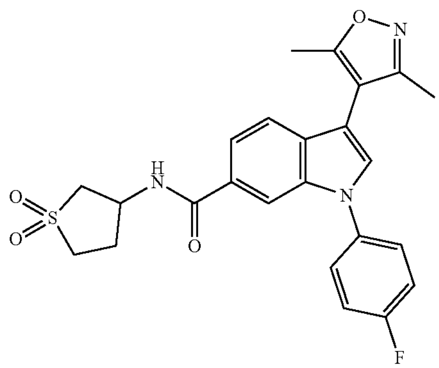 [SMILES: Cc1noc(C)c1-c1cn(-c2ccc(F)cc2)c2cc(C(=O)NC3CCS(=O)(=O)C3)ccc12] | 3-(3,5-dimethylisoxazol-4-yl)-N-(1,1-dioxidotetrahydrothiophen-3-yl)-1-(4-fluorophenyl)-1H-indole-6-carboxamide (racemic) | 468 |
| 54 | 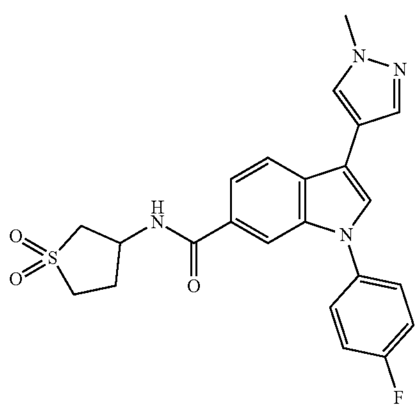 [SMILES: Cn1cc(-c2cn(-c3ccc(F)cc3)c3cc(C(=O)NC4CCS(=O)(=O)C4)ccc23)cn1] | N-(1,1-dioxidotetrahydrothiophen-3-yl)-1-(4-fluorophenyl)-3-(1-methyl-1H-pyrazol-4-yl)-1H-indole-6-carboxamide (racemic) | 453 |
| 55 | 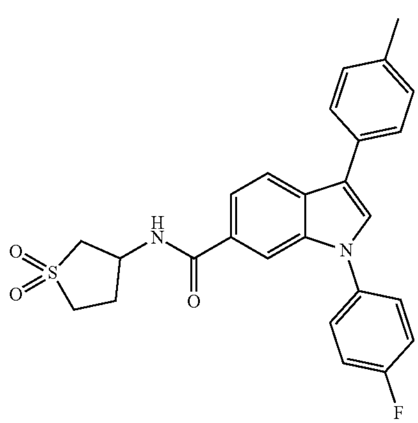 [SMILES: Cc1ccc(-c2cn(-c3ccc(F)cc3)c3cc(C(=O)NC4CCS(=O)(=O)C4)ccc23)cc1] | N-(1,1-dioxidotetrahydrothiophen-3-yl)-1-(4-fluorophenyl)-3-(4-methylphenyl)-1H-indole-6-carboxamide (racemic) | 463 |

TABLE 4-continued

| Ex. # | Structure | Chemical Name | m/z (M + 1) |
|---|---|---|---|
| 56 | 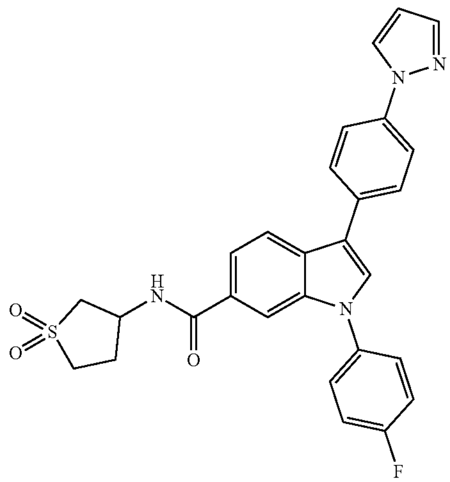 [SMILES: O=C(NC1CCS(=O)(=O)C1)c1ccc2c(-c3ccc(-n4cccn4)cc3)cn(-c3ccc(F)cc3)c2c1] | N-(1,1-dioxidotetrahydrothiophen-3-yl)-1-(4-fluorophenyl)-3-[4-(1H-pyrazol-1-yl)phenyl]-1H-indole-6-carboxamide (racemic) | 515 |
| 57 | 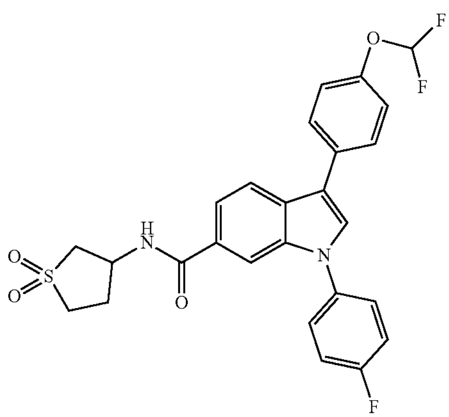 [SMILES: O=C(NC1CCS(=O)(=O)C1)c1ccc2c(-c3ccc(OC(F)F)cc3)cn(-c3ccc(F)cc3)c2c1] | 3-[4-(difluoromethoxy)phenyl]-N-(1,1-dioxidotetrahydrothiophen-3-yl)-1-(4-fluorophenyl)-1H-indole-6-carboxamide (racemic) | 515 |
| 58 | 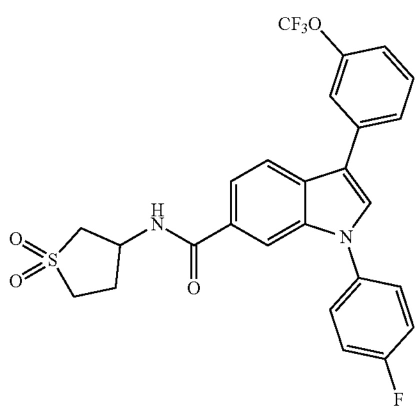 | N-(1,1-dioxidotetrahydrothiophen-3-yl)-1-(4-fluorophenyl)-3-[3-(trifluoromethoxy)phenyl]-1H-indole-6-carboxamide (racemic) | 533 |

TABLE 4-continued

| Ex. # | Structure | Chemical Name | m/z (M + 1) |
|---|---|---|---|
| 59 | 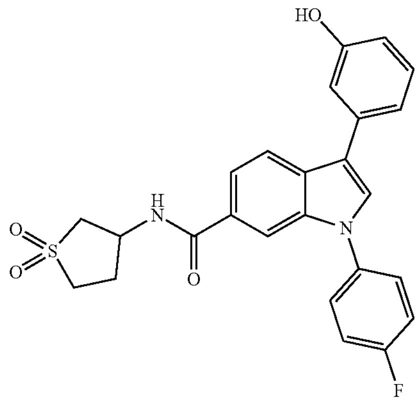 [SMILES: O=C(NC1CCS(=O)(=O)C1)c1ccc2c(-c3cccc(O)c3)cn(-c3ccc(F)cc3)c2c1] | N-(1,1-dioxidotetrahydrothiophen-3-yl)-1-(4-fluorophenyl)-3-(3-hydroxyphenyl)-1H-indole-6-carboxamide (racemic) | 465 |
| 60 | 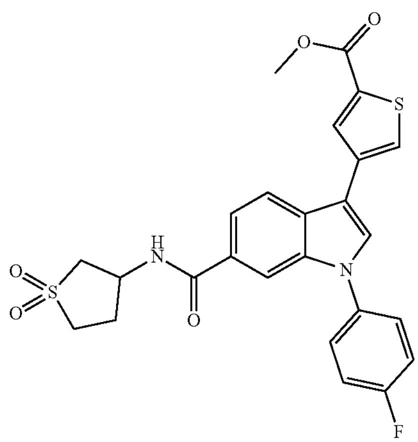 [SMILES: COC(=O)c1cc(-c2cn(-c3ccc(F)cc3)c3cc(C(=O)NC4CCS(=O)(=O)C4)ccc23)cs1] | methyl 4-{6-[(1,1-dioxidotetrahydrothiophen-3-yl)carbamoyl]-1-(4-fluorophenyl)-1H-indol-3-yl}thiophene-2-carboxylate (racemic) | 513 |
| 61 | 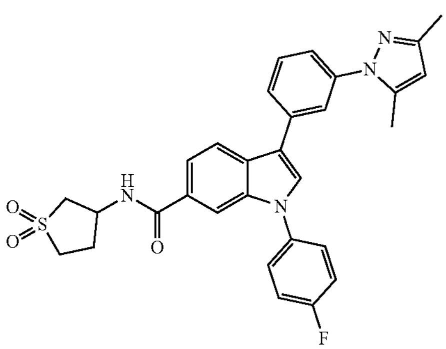 [SMILES: Cc1cc(C)n(-c2cccc(-c3cn(-c4ccc(F)cc4)c4cc(C(=O)NC5CCS(=O)(=O)C5)ccc34)c2)n1] | 3-[3-(3,5-dimethyl-1H-pyrazol-1-yl)phenyl]-N-(1,1-dioxidotetrahydrothiophen-3-yl)-1-(4-fluorophenyl)-1H-indole-6-carboxamide (racemic) | 543 |

Assays

Insect Cell Expression and Membrane Preparation

Sf-9 insect cells were maintained in Grace's insect cell culture medium with 10% heated-inactivated fetal bovine serum, 1% Pluronic F-68 and 0.14 µg/ml Kanamycine sulfate in Erlenmeyer flasks at 28° C. in a shaker incubator. After infection with untagged baculovirus expressing human DGAT2 (hDGAT2) at multiplicity of infection (MOI) 0.1 for 48 hours, cells were harvested. Cell pellets were suspended in buffer containing 10 mM Tris-HCl (pH 7.5), 1 mM EDTA (pH 8.0), 250 mM sucrose and Complete Protease Inhibitor Cocktail (Roche Diagnostics Corp., Indianapolis, Ill.), and sonicated on ice. Membrane fractions were isolated by ultracentrifugation (100,000×g pellet), resuspended in the same buffer, and frozen (−80° C.) for later use. The protein concentration was determined with the BCA Protein Assay kit (Pierce Biotechnology Inc., Rockford, Ill.). Expression of protein levels was analyzed by immunoblotting with goat polyclonal DGAT2 antibody C-15 and donkey anti-goat IgG HRP (Santa Cruz Biotechnology, Inc., Santa Cruz, Calif.) followed by detection with ECL reagent (GE Healthcare, Piscataway, N.J.).

LC/MS/MS Analysis Method

LC/MS/MS analyses were performed using Thermal Fisher's LX4-TSQ Vantage system. This system consists of an Agilent binary high-performance liquid chromatography (HPLC) pumps and a TSQ Vantage triple quadrupole MS/MS instrument. For each sample, 2 µL samples from the top organic layer of in-plate liquid-liquid extraction were injected onto a Thermo Betabasic C4 column (2.1 mm×20 mm, 5 μm particle size). The samples were then eluted using the following conditions; mobile phase: methanol/water with 0.1% ammonium format=92/8 (v/v), flow rate: 1 mL/min, temperature: 25 C. Data was acquired in positive mode using a heated electrospray ionization (HESI) interface. The operational parameters for the TSQ Vantage MS/MS instrument were a spray voltage of 3000 V, capillary temperature of 280° C., vaporizer temperature 400° C., shealth gas 60 arbitrary unit, Aux gas 40 arbitrary units, S-lens 113 and collision gas 0.16 Pascals. Standard reference material (SRM) chromatograms of triolein (Q1:902.9>Q3:602.3) and internal standard (Q1:902.9>Q3:602.3) were collected for 40 sec. The peak area was integrated by Xcalibur Quan software. The ratio between the triolein generated in the reaction and spiked in internal standard was used to generate percentage inhibition and $IC_{50}$ values. Compound percentage inhibition was calculated by the following formula: Inhibition %/=1−[(compound response−low control)/(high control−low control)]×100%. Potent compounds were titrated and $IC_{50}$ were calculated by 4 parameter sigmoidal curve fitting formula.

DGAT2 Enzymatic Activity Assay

DGAT2 activity was determined by measuring the amount of enzymatic product triolein (1,2,3-Tri(cis-9-octadecenoyl) glycerol) using the membrane prep mentioned above. The assay was carried out in deep well 384 plates in a final volume of 40 μL at rt. The assay mixture contained the following: assay buffer (100 mM Tris.Cl, pH 7.0, 20 mM $MgCl_2$, 5% ethanol), 25 μM of diolein, 10 μM of oleoyl-CoA and 10 ng/μL of DGAT2 membrane.

TABLE 5

| IC$_{50}$ values for inhibition of DGAT2 | |
| --- | --- |
| Ex. # | Human DGAT2 IC$_{50}$ (nM) |
| 1 | 8.8 |
| 1-A | 5.6 |
| 1-B | 6.6 |
| 2 | 66 |
| 2-A | 171 |
| 2-B | 30 |
| 3 | 344 |
| 4 | 629 |
| 5 | 190 |
| 6 | 476 |
| 7 | 671 |
| 8-A | 934 |
| 8-B | 692 |
| 9-A | 448 |
| 9-B | 235 |
| 10-A | 0.94 |
| 10-B | 1.0 |
| 11-A | 2.1 |
| 12-A | 0.79 |
| 12-B | 0.73 |
| 13-A | 1.8 |
| 14-A | 16 |
| 14-B | 9.8 |
| 15-A | 78 |
| 15-B | 28 |
| 16-A | 2.7 |
| 17-A | 3.3 |
| 18-A | 1.7 |
| 18-B | 0.91 |
| 19-A | 1.6 |
| 20 | 802 |
| 21 | 252 |
| 22 | 664 |
| 23 | 117 |
| 24 | 571 |
| 25 | 0.77 |
| 26-A | 2.9 |

TABLE 5-continued

| IC$_{50}$ values for inhibition of DGAT2 | |
| --- | --- |
| Ex. # | Human DGAT2 IC$_{50}$ (nM) |
| 27-A | 0.52 |
| 28 | 17 |
| 29 | 223 |
| 30 | 18 |
| 31 | 28 |
| 32 | 3.2 |
| 33 | 4.0 |
| 34 | 13 |
| 35 | 101 |
| 36 | 61 |
| 37 | 163 |
| 38 | 15 |
| 39 | 1.1 |
| 40 | 26 |
| 41 | 88 |
| 42 | 108 |
| 43 | 55 |
| 44 | 19 |
| 45 | 13 |
| 46 | 2.1 |
| 47 | 942 |
| 48 | 53 |
| 49 | 155 |
| 50 | 321 |
| 51 | 102 |
| 52 | 129 |
| 53 | 502 |
| 54 | 345 |
| 55 | 696 |
| 56 | 117 |
| 57 | 562 |
| 58 | 14 |
| 59 | 492 |
| 60 | 175 |
| 61 | 929 |

What is claimed is:

1. A compound having structural Formula I:

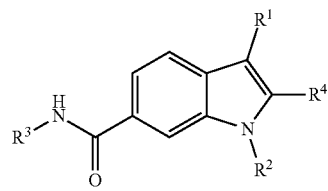

I or a pharmaceutically acceptable salt thereof wherein:

$R^1$ is (1) aryl unsubstituted or substituted by 1-3 $R^5$, or (2) 5- or 6-membered heteroaryl containing 1, 2, or 3 heteroatoms independently selected from N, O, and S, wherein the heteroaryl is unsubstituted or substituted by 1-3 $R^5$, or (3) 8- to 10-membered fused heteroaryl containing 1, 2, or 3 heteroatoms independently selected from N, O, and S, wherein the heteroaryl is unsubstituted or substituted by 1-3 $R^5$;

R² is

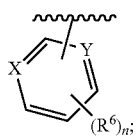

R³ is
(1) —(C₁₋₆)alkyl-O—(C₁₋₃)alkyl,
(2) 4- to 7-membered monocyclic or 6- to 10-membered bicyclic heterocyclyl containing 1 or 2 heteroatoms independently selected from N, O, and S, wherein the heterocyclyl is unsubstituted or substituted by 1-3 R⁷,
(3) —(C₁₋₆)alkyl-heterocyclyl containing 1 or 2 heteroatoms independently selected from N, O, and S, and wherein the heterocyclyl is a 5- to 7-membered ring, or
(4) —(C₁₋₆)alkyl-pyridinyl, wherein the pyridinyl is unsubstituted or substituted with (C₁₋₃)alkyl or halo (C₁₋₃)alkyl, and wherein the alkyl is unsubstituted or substituted with a hydroxy;
R⁴ is
(1) hydrogen,
(2) (C₁₋₃)alkyl, or
(3) CN;
each R⁵ is
(1) halo,
(2) (C₁₋₃)alkyl,
(3) halo(C₁₋₃)alkyl,
(4) (C₃₋₆)cycloalkyl,
(5) —C(O)NH₂,
(6) —C(O)O(C₁₋₃)alkyl,
(7) (C₁₋₃)alkoxy,
(8) halo(C₁₋₃)alkoxy,
(9) hydroxy,
(10) phenyl,
(11) —NHC(O)CH₃,
(12) 5- or 6-membered heteroaryl containing 1, 2, or 3 heteroatoms independently selected from N, O, and S, wherein the heteroaryl is unsubstituted or substituted by 1-2 (C₁₋₃)alkyl, or hydroxy,
(13) CN,
(14) hydroxy(C₁₋₃)alkyl, or
(15) (C₁₋₃)alkyl-heterocyclyl, wherein the heterocyclyl contains 1 or 2 heteroatoms independently selected from N, O, or S, and wherein the heterocyclyl is a 5- to 7-membered ring;
each R⁶ is
(1) hydrogen, or
(2) halo;
each R⁷ is
(1) oxo, or
(2) (C₁₋₃)alkyl;
X is CH or N;
Y is CH or N;
n is 1 or 2.

2. The compound of claim 1, wherein R³ is —(C₁₋₆)alkyl-O—(C₁₋₃)alkyl; a 5- to 7-membered heterocyclyl containing 1 or 2 heteroatoms independently selected from N, O, and S, wherein the heterocyclyl is unsubstituted or substituted by 1-3 R⁷; or —(C₁₋₆)alkyl-heterocyclyl containing 1 or 2 heteroatoms independently selected from N, O, and S, and wherein the heterocyclyl is a 5- to 7-membered ring, or a pharmaceutically acceptable salt thereof.

3. The compound of claim 2, wherein R² is

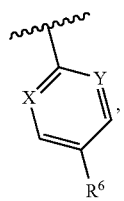

or a pharmaceutically acceptable salt thereof.

4. The compound of claim 2, wherein R³ is

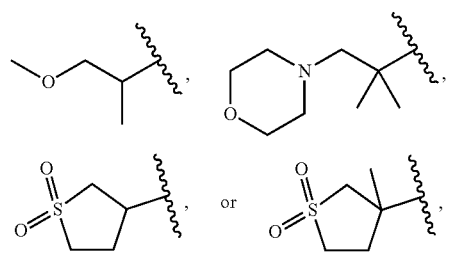

or a pharmaceutically acceptable salt thereof.

5. The compound of claim 4, wherein R² is

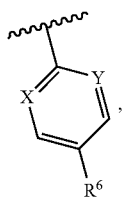

or a pharmaceutically acceptable salt thereof.

6. The compound of claim 4, wherein R³ is

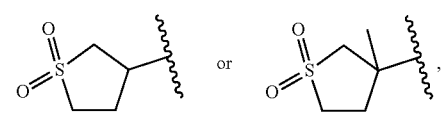

or a pharmaceutically acceptable salt thereof.

7. The compound of claim 6, wherein R² is

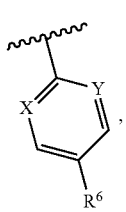

or a pharmaceutically acceptable salt thereof.

8. The compound claim 1, wherein R² is

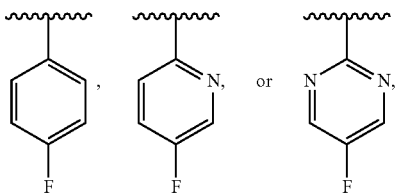

or a pharmaceutically acceptable salt thereof.

9. A compound of claim 1, selected from the group consisting of
(1) 3-(2-chlorophenyl)-1-(4-fluorophenyl)-N-(3-methyl-1,1-dioxidotetrahydrothiophen-3-yl)-1H-indole-6-carboxamide,
(2) 3-(2-Chlorophenyl)-N-(1,1-dioxidotetrahydrothiophen-3-yl)-1-(4-fluorophenyl)-1H-indole-6-carboxamide,
(3) 3-(2-chlorophenyl)-1-(4-fluorophenyl)-N-(1-methoxypropan-2-yl)-1H-indole-6-carboxamide,
(4) 3-(2-chlorophenyl)-1-(4-fluorophenyl)-N-(2-methyl-1-morpholinopropan-2-yl)-1H-indole-6-carboxamide,
(5) (S)-3-(2-chlorophenyl)-1-(4-fluorophenyl)-N-(2-hydroxy-1-(6-(trifluoromethyl)pyridin-3-yl)ethyl)-1H-indole-6-carboxamide,
(6) (S)-3-(2-chlorophenyl)-1-(4-fluorophenyl)-N-(1-(6-(trifluoromethyl)pyridin-3-yl)ethyl)-1H-indole-6-carboxamide
(7) (R)-3-(2-chlorophenyl)-1-(4-fluorophenyl)-N-(1-(6-(trifluoromethyl)pyridin-3-yl)ethyl)-1H-indole-6-carboxamide,
(8) 3-(2-chlorophenyl)-1-(4-fluorophenyl)-2-methyl-N-(3-methyl-1,1-dioxidotetrahydrothiophen-3-yl)-1H-indole-6-carboxamide,
(9) 3-(2-chlorophenyl)-2-cyano-1-(4-fluorophenyl)-N-(3-methyl-1,1-dioxidotetrahydrothiophen-3-yl)-1H-indole-6-carboxamide,
(10) 3-(3-(difluoromethoxy)phenyl)-1-(5-fluoropyridin-2-yl)-N-(3-methyl-1,1-dioxidotetrahydrothiophen-3-yl)-1H-indole-6-carboxamide,
(11) 3-(3-cyclopropylphenyl)-N-(1,1-dioxidotetrahydrothiophen-3-yl)-1-(5-fluoropyridin-2-yl)-1H-indole-6-carboxamide,
(12) 3-(3-cyclopropylphenyl)-1-(5-fluoropyridin-2-yl)-N-(3-methyl-1,1-dioxidotetrahydrothiophen-3-yl)-1H-indole-6-carboxamide,
(13) 3-(3-(difluoromethoxy)phenyl)-N-(1,1-dioxidotetrahydrothiophen-3-yl)-1-(5-fluoropyridin-2-yl)-1H-indole-6-carboxamide,
(14) 3-(2-chlorophenyl)-1-(5-fluoropyridin-2-yl)-N-(3-methyl-1,1-dioxidotetrahydrothiophen-3-yl)-1H-indole-6-carboxamide,
(15) 3-(2-chlorophenyl)-1-(5-fluoropyrimidin-2-yl)-N-(3-methyl-1,1-dioxidotetrahydrothiophen-3-yl)-1H-indole-6-carboxamide,
(16) 3-(3-cyclopropylphenyl)-1-(5-fluoropyrimidin-2-yl)-N-(3-methyl-1,1-dioxidotetrahydrothiophen-3-yl)-1H-indole-6-carboxamide,
(17) 3-(3-cyclopropylphenyl)-N-(1,1-dioxidotetrahydrothiophen-3-yl)-1-(5-fluoropyrimidin-2-yl)-1H-indole-6-carboxamide,
(18) 3-(3-(difluoromethoxy)phenyl)-1-(5-fluoropyrimidin-2-yl)-N-(3-methyl-1,1-dioxidotetrahydrothiophen-3-yl)-1H-indole-6-carboxamide,
(19) 3-(3-(difluoromethoxy)phenyl)-N-(1,1-dioxidotetrahydrothiophen-3-yl)-1-(5-fluoropyrimidin-2-yl)-1H-indole-6-carboxamide,
(20) 3-(4,6-dimethylpyridin-2-yl)-N-(1,1-dioxidotetrahydrothiophen-3-yl)-1-(4-fluorophenyl)-1H-indole-6-carboxamide,
(21) 3-(4-chloropyridin-2-yl)-N-(1,1-dioxidotetrahydrothiophen-3-yl)-1-(4-fluorophenyl)-1H-indole-6-carboxamide,
(22) N-(1,1-dioxidotetrahydrothiophen-3-yl)-1-(4-fluorophenyl)-3-(pyridin-2-yl)-1H-indole-6-carboxamide,
(23) N-(1,1-dioxidotetrahydrothiophen-3-yl)-1-(4-fluorophenyl)-3-(4-methylpyridin-2-yl)-1H-indole-6-carboxamide,
(24) 1-(4-fluorophenyl)-N-(3-methyl-1,1-dioxidotetrahydrothiophen-3-yl)-3-(4-methylpyridin-2-yl)-1H-indole-6-carboxamide,
(25) 3-(5-(difluoromethoxy)pyridin-3-yl)-1-(4-fluorophenyl)-N-(3-methyl-1,1-dioxidotetrahydrothiophen-3-yl)-1H-indole-6-carboxamide,
(26) 3-(3-Cyclopropylphenyl)-N-(1,1-dioxidotetrahydrothiophen-3-yl)-1-(4-fluorophenyl)-1H-indole-6-carboxamide,
(27) 3-(3-(difluoromethoxy)phenyl)-N-(1,1-dioxidotetrahydrothiophen-3-yl)-1-(4-fluorophenyl)-1H-indole-6-carboxamide,
(28) 3-(3-(difluoromethoxy)phenyl)-1-(4-fluorophenyl)-2-methyl-N-(3-methyl-1,1-dioxidotetrahydrothiophen-3-yl)-1H-indole-6-carboxamide,
(29) N-(1,1-dioxidotetrahydrothiophen-3-yl)-1-(4-fluorophenyl)-3-(2-methoxyphenyl)-1H-indole-6-carboxamide,
(30) N-(1,1-dioxidotetrahydrothiophen-3-yl)-1-(4-fluorophenyl)-3-[3-(trifluoromethyl)phenyl]-1H-indole-6-carboxamide,
(31) 3-(3-chlorophenyl)-N-(1,1-dioxidotetrahydrothiophen-3-yl)-1-(4-fluorophenyl)-1H-indole-6-carboxamide,
(32) methyl 3-{6-[(1,1-dioxidotetrahydrothiophen-3-yl)carbamoyl]-1-(4-fluorophenyl)-1H-indol-3-yl}benzoate,
(33) N-(1,1-dioxidotetrahydrothiophen-3-yl)-1-(4-fluorophenyl)-3-(3-methoxyphenyl)-1H-indole-6-carboxamide,
(34) N-(1,1-dioxidotetrahydrothiophen-3-yl)-1-(4-fluorophenyl)-3-(3-methylphenyl)-1H-indole-6-carboxamide,
(35) N-(1,1-dioxidotetrahydrothiophen-3-yl)-3-(3-fluorophenyl)-1-(4-fluorophenyl)-1H-indole-6-carboxamide,
(36) 3-biphenyl-3-yl-N-(1,1-dioxidotetrahydrothiophen-3-yl)-1-(4-fluorophenyl)-1H-indole-6-carboxamide,
(37) 3-[3-(acetylamino)phenyl]-N-(1,1-dioxidotetrahydrothiophen-3-yl)-1-(4-fluorophenyl)-1H-indole-6-carboxamide,
(38) N-(1,1-dioxidotetrahydrothiophen-3-yl)-1-(4-fluorophenyl)-3-[3-(1H-pyrazol-1-yl)phenyl]-1H-indole-6-carboxamide,
(39) 3-[3-(difluoromethoxy)phenyl]-N-(1,1-dioxidotetrahydrothiophen-3-yl)-1-(4-fluorophenyl)-1H-indole-6-carboxamide,
(40) N-(1,1-dioxidotetrahydrothiophen-3-yl)-3-(2-fluorophenyl)-1-(4-fluorophenyl)-1H-indole-6-carboxamide,
(41) 3-(3,5-dichlorophenyl)-N-(1,1-dioxidotetrahydrothiophen-3-yl)-1-(4-fluorophenyl)-1H-indole-6-carboxamide,

(42) 3-[2-(difluoromethoxy)phenyl]-N-(1,1-dioxidotetrahydrothiophen-3-yl)-1-(4-fluorophenyl)-1H-indole-6-carboxamide,
(43) N-(1,1-dioxidotetrahydrothiophen-3-yl)-1-(4-fluorophenyl)-3-phenyl-1H-indole-6-carboxamide,
(44) 3-(2,3-dichlorophenyl)-N-(1,1-dioxidotetrahydrothiophen-3-yl)-1-(4-fluorophenyl)-1H-indole-6-carboxamide,
(45) 3-(3-cyanophenyl)-N-(1,1-dioxidotetrahydrothiophen-3-yl)-1-(4-fluorophenyl)-1H-indole-6-carboxamide,
(46) 3-(3-cyclopropylphenyl)-N-(1,1-dioxidotetrahydrothiophen-3-yl)-1-(4-fluorophenyl)-1H-indole-6-carboxamide,
(47) 3-(2,6-dichlorophenyl)-N-(1,1-dioxidotetrahydrothiophen-3-yl)-1-(4-fluorophenyl)-1H-indole-6-carboxamide,
(48) 3-(2,6-difluorophenyl)-N-(1,1-dioxidotetrahydrothiophen-3-yl)-1-(4-fluorophenyl)-1H-indole-6-carboxamide,
(49) 3-(2-chloro-6-fluorophenyl)-N-(1,1-dioxidotetrahydrothiophen-3-yl)-1-(4-fluorophenyl)-1H-indole-6-carboxamide,
(50) N-(1,1-dioxidotetrahydrothiophen-3-yl)-1-(4-fluorophenyl)-3-pyrimidin-5-yl-1H-indole-6-carboxamide,
(51) N-(1,1-dioxidotetrahydrothiophen-3-yl)-1-(4-fluorophenyl)-1'-methyl-1H,1'H-3,5'-biindole-6-carboxamide,
(52) N-(1,1-dioxidotetrahydrothiophen-3-yl)-1-(4-fluorophenyl)-3-pyridin-3-yl-1H-indole-6-carboxamide,
(53) 3-(3,5-dimethylisoxazol-4-yl)-N-(1,1-dioxidotetrahydrothiophen-3-yl)-1-(4-fluorophenyl)-1H-indole-6-carboxamide,
(54) N-(1,1-dioxidotetrahydrothiophen-3-yl)-1-(4-fluorophenyl)-3-(1-methyl-1H-pyrazol-4-yl)-1H-indole-6-carboxamide,
(55) N-(1,1-dioxidotetrahydrothiophen-3-yl)-1-(4-fluorophenyl)-3-(4-methylphenyl)-1H-indole-6-carboxamide,
(56) N-(1,1-dioxidotetrahydrothiophen-3-yl)-1-(4-fluorophenyl)-3-[4-(1H-pyrazol-1-yl)phenyl]-1H-indole-6-carboxamide,
(57) 3-[4-(difluoromethoxy)phenyl]-N-(1,1-dioxidotetrahydrothiophen-3-yl)-1-(4-fluorophenyl)-1H-indole-6-carboxamide,
(58) N-(1,1-dioxidotetrahydrothiophen-3-yl)-1-(4-fluorophenyl)-3-[3-(trifluoromethoxy)phenyl]-1H-indole-6-carboxamide,
(59) N-(1,1-dioxidotetrahydrothiophen-3-yl)-1-(4-fluorophenyl)-3-(3-hydroxyphenyl)-1H-indole-6-carboxamide,
(60) methyl 4-{6-[(1,1-dioxidotetrahydrothiophen-3-yl)carbamoyl]-1-(4-fluorophenyl)-1H-indol-3-yl}thiophene-2-carboxylate, and
(61) 3-[3-(3,5-dimethyl-1H-pyrazol-1-yl)phenyl]-N-(1,1-dioxidotetrahydrothiophen-3-yl)-1-(4-fluorophenyl)-1H-indole-6-carboxamide;

or a pharmaceutically acceptable salt thereof.

10. A pharmaceutical composition comprising of the compound of claim 1, or a pharmaceutically acceptable salt thereof, and a pharmaceutically acceptable carrier.

11. A method of treating atherosclerosis, hepatic steatosis, atherosclerosis, type-2 diabetes mellitus, obesity, hyperlipidemia, non-alcoholic steatohepatitis or hypercholesterolemia in a patient in need of treatment comprising the administration to the patient of a therapeutically effective amount of a compound of claim 1.

12. The method according to claim 11 for treating atherosclerosis.

13. The method according to claim 11 for treating non-alcoholic steatohepatitis.

* * * * *